(12) United States Patent
Raghavan

(10) Patent No.: US 9,006,292 B2
(45) Date of Patent: Apr. 14, 2015

(54) METADICHOL® LIQUID AND GEL NANOPARTICLE FORMULATIONS

(71) Applicant: NanoRx, Inc., Chappaqua, NY (US)

(72) Inventor: Palayakotai R. Raghavan, Chappaqua, NY (US)

(73) Assignee: NanoRx, Inc., Chappaqua, NY (US)

( * ) Notice: Subject to any disclaimer, the term of this patent is extended or adjusted under 35 U.S.C. 154(b) by 29 days.

(21) Appl. No.: 14/205,243

(22) Filed: Mar. 11, 2014

(65) Prior Publication Data

US 2014/0275285 A1   Sep. 18, 2014

Related U.S. Application Data

(60) Provisional application No. 61/794,490, filed on Mar. 15, 2013.

(51) Int. Cl.
| | |
|---|---|
| *A61K 31/045* | (2006.01) |
| *B82Y 30/00* | (2011.01) |
| *A61K 9/14* | (2006.01) |
| *A61K 47/32* | (2006.01) |

(52) U.S. Cl.
CPC ............... *A61K 31/045* (2013.01); *A61K 9/14* (2013.01); *A61K 47/32* (2013.01); *B82Y 30/00* (2013.01); *Y10S 977/773* (2013.01)

(58) Field of Classification Search
CPC .............................. A61K 31/045; B82Y 30/00
USPC .......................................... 514/724; 977/773
See application file for complete search history.

(56) References Cited

U.S. PATENT DOCUMENTS

| | | |
|---|---|---|
| 4,670,471 A | 6/1987 | Clark |
| 2003/0198616 A1 | 10/2003 | Howard |
| 2005/0074443 A1 | 4/2005 | Treadwell |
| 2007/0196507 A1 | 8/2007 | Majeed et al. |
| 2009/0191288 A1 | 7/2009 | Squires |
| 2010/0215752 A1 | 8/2010 | Raghavan |
| 2013/0045179 A1 | 2/2013 | Ciustea et al. |

*Primary Examiner* — Raymond Henley, III
(74) *Attorney, Agent, or Firm* — Morgan, Lewis & Bockius LLP

(57) ABSTRACT

The present invention provides methods of regulating physiological and metabolic parameters and of treating diseases by administering metadichol to a subject in need of such regulation and/or treatment. Metadichol can be administered as a liquid or gel formulation.

12 Claims, 15 Drawing Sheets

| Compound | IC 50 (nm) |
|---|---|
| Metadichol | 509 |

Reference compounds
chloroquine 4.3 nm
Artesunate 1.7 nm

METADICHOL® LIQUID AND GEL NANOPARTICLE FORMULATIONS

PRIORITY CLAIM

This application claims priority to U.S. Patent Application No. 61/794,490, filed Mar. 15, 2013, the contents of which are incorporated by reference in their entirety for all purposes.

FIELD OF THE INVENTION

The present invention relates to a novel formulation of Metadichol® a Nano particulate in liquid oral and in polymeric Nano gel formulation. The Metadichol® formulation (previously described in US patent application (Ser. No. 12/691,706)) behaves as an inverse agonist against the Vitamin D receptor (VDR). This application relates to methods of treating, and preventing diseases and extends the therapeutic effects beyond what is observed with 1,25 dihydroxy Vitamin $D_3$ (Calcitriol) the active form of Vitamin D in the human body.

BACKGROUND OF THE INVENTION

Vitamin D, acquired either from dietary sources or via ultraviolet irradiation of 7-dehydrocholesterol in the epidermis, is metabolized to its hormonal form. The keratinocytes of the skin are unique in being not only the primary source of vitamin D for the body, but also possessing the enzymatic machinery to metabolize vitamin D to active metabolites. Many functions of the skin are regulated by vitamin D and/or its receptor: these include inhibition of proliferation, stimulation of differentiation including formation of the permeability barrier, promotion of innate immunity, regulation of the hair follicle cycle, and suppression of tumors.

When exposed to ultraviolet radiation, cells in the epidermis convert a cholesterol related steroid to vitamin D or cholecalciferol. Vitamin D is essential for proper development of the bones. The ultraviolet radiation necessary for vitamin D synthesis (specifically, UV-B) only reaches the Earth's surface in much abundance for a few hours a day when the sun is high. Much less of it reaches the Earth's surface at high latitudes than at low latitudes, and very little reaches the Earth's surface on cloudy days or during the winter. Even so, the average fair-skinned person can make and store several days' worth of vitamin D with just one hour's exposure to the midday sun. Dark-skinned people living at high latitudes are much more likely to suffer from vitamin D deficiency than are light-skinned people.

The most important source of Vitamin D is through the action of sun on cholesterol on the skin. Vitamin D modulates T-cell responses and has anti-inflammatory properties, and boosts innate immune responses by induction of the human gene for cathelicidin. Cathelicidin's and defensins are small peptides with amphipathic structures that allow them to disrupt the integrity of the pathogen cell membrane, resulting in its death. Most immune cells or those epithelial cells that are in contact with the environment express these proteins. Deficiency in these peptides results in increased susceptibility to infection.

Vitamin D enters the circulation and is transported to the liver, where it is hydroxylated to form 25-hydroxyvitamin $D_3$ (calcidiol; the major circulating form of vitamin D). In the kidneys, the 25-hydroxyvitamin $D_3$-1-hydroxylase enzyme catalyzes a second hydroxylation of 25-hydroxyvitamin D, resulting in the formation of 1,25-dihydroxyvitamin $D_3$ (calcitriol, 1alpha, 25-dihydroxyvitamin D]—the most potent form of vitamin D. Most of the physiological effects of vitamin D in the body are related to the activity of 1,25-dihydroxyvitamin D. Keratinocytes in the epidermis possess hydroxylase enzymes that locally convert vitamin D to 1,25 dihydroxyvitamin $D_3$, (Bikle, et al. 1986, Biochemistry. 25 (7): 1545-15480) the form that regulates epidermal proliferation and differentiation. In skin, the vitamin D receptor (VDR) appears to have other roles that are independent of its association with 1,25 dihydroxyvitamin D3. For instance, the VDR is important in regulating the growth cycle of mature hair follicles. (Bikle, et al., *J. Bone. Miner. Metab*, (2010) 28:117-130). Certain mutations in the VDR lead to misregulated gene expression resulting in aberrant hair follicle cycling and alopecia (hair loss) in mice (28, 29) and in humans (30). The VDR also functions as a tumor suppressor in skin. The VDR is one of several factors that control these two diverse roles. Moreover, 1,25-dihydroxyvitamin $D_3$ is a potent immune modulator in skin.

Functions in Healthy Skin

Photo protection photo damage refers to skin damage induced by ultraviolet (UV) light. Depending on the dose, UV light can lead to DNA damage, inflammatory responses, skin cell apoptosis (programmed cell death), skin aging, and skin cancer. Some studies, mainly in vitro (cell culture) studies (Dixon, K M, et al. 2005, *J Steroid Biochem Mol Biol*, 97(1-2):137-143) and mouse studies where 1,25-dihydroxyvitamin $D_3$ was topically applied to skin before or immediately following irradiation, have found that vitamin D exhibits photo protective effects (Gupta, et al., 2007, *J Invest Dermatol*. 127(3):707-715). Documented effects in skin cells include decreased DNA damage, reduced apoptosis, increased cell survival, and decreased erythema. The mechanisms for such effects are not known, but one mouse study found that 1,25-dihydroxyvitamin $D_3$ induced expression of metallothionein (a protein that protects against free radicals and oxidative damage) in the stratum basale. It has also been postulated that nongenomic actions of vitamin D contribute to the photo protection; such effects of vitamin D involve cell-signaling cascades that open calcium channels. 1,25-dihydroxyvitamin $D_3$ regulates the expression of cathelicidin (LL-37/hCAP18) (40, 41), an antimicrobial protein that appears to mediate innate immunity in skin by promoting wound healing and tissue repair. One human study found that cathelicidin expression is up regulated during early stages of normal wound healing (Gombart A F, *Faseb J.*, 2005, 19(9): 1067-1077). Other studies have shown that cathelicidin modulates inflammation in skin Kratz, G, et al., 2003, *J Invest Dermatol*. 120(3):379-389), induces angiogenesis (Kupatt C, et al., *J Clin Invest.*, 2003, 111(11):1665-1672), and improves re-epithelialization (the process of restoring the epidermal barrier to re-establish a functional barrier that protects underlying cells from environmental exposures). The active form of vitamin D and its analogs have been shown to up regulate cathelicidin expression in cultured keratinocytes (Sthale M, 2005, *J Invest Dermatol.*, 124(5):1080-1082).

Diseases such as rosacea may require lower levels of vitamin D or even locally active serine proteases inhibitors and vitamin D antagonists to prevent harm. In rosacea, patients might benefit from therapies blocking cathelicidin expression and processing. Polymorphisms in the vitamin D receptor gene have been described in patients with severe rosacea indicating that vitamin D3 signaling is involved in pathogenesis (Jansen T, et. al, J Dermatol 2004; 31:244-246.). Blocking cathelicidin expression by targeting the vitamin D3 pathway might represent a novel therapeutic approach in rosacea. As an example, vitamin D3 analogues without intrinsic activity at the vitamin D receptor have been shown to inhibit 1,25D3-induced cathelicidin in keratinocytes in vitro (Liu P. T, et. al, Science 2006; 311:1770-1773).

In psoriasis, blocking cathelicidin peptide could break the vicious cycle of increased LL-37 expression, dendritic cell activation and cutaneous inflammation. Again strategies to decrease cathelicidin in keratinocytes could target vitamin D3 signaling. Paradoxically, for a long time vitamin D3 analogues have been used in the therapy of psoriasis. Vitamin D3 analogues bind to and activate the vitamin D receptor and should therefore increase cathelicidin in keratinocytes presumably worsening inflammation in psoriasis. However, the opposite is true: vitamin D analogues resemble one of the pillars of topical psoriasis treatment. They ameliorate cutaneous inflammation and reverse morphological changes within skin lesions. (Lebwohl M, et. al, J Am Acad Dermatol 2004; 50:416-430). Understanding the molecular effects of vitamin D3 analogues on cutaneous innate immune function will eventually also lead to better treatment. In summary, influencing cathelicidin expression via vita-min D3 signaling might offer a new treatment angle in the therapy of very common skin diseases. However, until the 'sunshine vitamin' can be targeted additional experimental work and clinical studies have to be performed to prove its safety and benefits. Overall, current data overwhelmingly support the importance of AMPs to healthy human skin but the key steps to put this information to therapeutic use remain to be done.

Eczema (Bjorn Hartmann, et. al, Journal of Investigative Dermatology (2012), Volume 132) is a chronic inflammatory skin disease that has reached nearly epidemic proportions in childhood. Moreover, it is a difficult disease to control and, with its onset in childhood, is often the first manifestation of atrophy. The clinical features of eczema include itchy red skin accompanied by dryness and lichenification. In the past, treatment options consisted primarily of avoidance of soap and water. These options have considerably improved with both non-pharmacologic and pharmacologic approaches. However, eczema is still a treatment challenge. Part of the problem in developing new treatment options has been the relative failure in translating basic science information into clinical application. It is hoped that the newer biologics will help bridge this gap and lead to greater success rates.

Atopic dermatitis (AD) is a common chronic inflammatory skin disease that has increased in prevalence over the last several decades in industrialized countries. AD is a multifactorial, heterogeneous disease with a variety of defects in the immune system, in antimicrobial defense mechanisms and epidermal barrier integrity, which collectively contribute to the risk and severity of AD development. (J Innate Immun 2011; 3:131-141).

Topical corticosteroids have been the gold standard for the treatment of atopic dermatitis for many decades. The emergence of the immuno-modulatory drugs Tacrolimus and Picrolimus represented the first major advance in the treatment of this disease in 40 years. Numerous other therapeutic modalities have been studied and whereas some have been found to have beneficial effects, none have exceeded the efficacy of topical corticosteroids. Less severe forms of eczema are generally treated successfully with topical steroids or immuno-modulatory drugs, however, Steroid-resistant eczema presents a problem because most of the other adjunctive treatments do not completely resolve the condition.

Warts are a benign proliferation of the skin and mucosa caused by infection with human papillomavirus (HPV). HPV is ubiquitous, and renal transplant recipients (RTRs) may never totally clear HPV infections, which are the most frequently recurring infections. This infection is important because of its link to the development of certain skin cancers, in particular, squamous cell carcinoma. Regular surveillance, sun avoidance, and patient education are important aspects of the management strategy. Warts are usually treated by traditional destructive modalities such as cryotherapy with liquid nitrogen, local injection of bleomycin, electrocoagulation, topical application of glutaraldehyde, and local and systemic interferon-β therapy [S. Gibbs, et. al, British Medical Journal, vol. 325, no. 7362, pp. 461-464, 2002. However, the tolerance of patients to these treatment modalities is poor, because they often cause pain, especially in children, and sometimes scarring or pigmentation after treatment. No treatment has been uniformly effective, and warts are often refractory, especially in immuno-compromised patients where their quality of life is threatened. Researchers have reported an RTR with a right index finger wart, which was successfully treated with a topical activated vitamin D. (Luciano Moscarelli, et. al, Case Reports in Transplantation Volume 2011, Article ID 368623).

Hair loss (alopecia) is a much-feared side effect of many chemotherapy protocols and is one of the most psychological devastating aspects of cancer therapy. So far, no satisfactory strategy for suppressing chemotherapy-induced alopecia is at hand. During the last decade, some progress in understanding molecular mechanisms of chemotherapy-induced hair loss has been achieved using rodent models. However, the pathobiology of the response of human hair follicle to chemotherapy remains largely unknown. (Vladimir A Botchkarev, Journal of Investigative Dermatology Symposium Proceedings (2003) 8, 72-75).

Androgenetic alopecia is the most common hair loss disorder in men and is largely determined by genetic factors and the peripheral action of androgens. Others mechanisms such as chronic inflammation and several hormones or vitamins like aldosterone, insulin or vitamin D have been implicated in the pathogenesis of Androgenetic alopecia. The diagnosis of Androgenetic alopecia is made by clinical history and clinical examination. Minoxidil and finasteride are the main drugs approved for the treatment of Androgenetic alopecia. Androgenetic alopecia has been associated with cardiovascular risk factors and benign prostatic hyperplasia. Alopecia is a feature of vitamin D receptor (VDR) mutations in humans and in VDR null mice. This alopecia results from an inability to initiate the anagen phase of the hair cycle after follicle morphogenesis is complete.

Thus, once the initial hair is shed it does not regrow. VDR expression in the epidermal component of the hair follicle, the keratinocyte, is critical for maintenance of the hair cycle. To determine which functional domains of the VDR are required for hair cycling, mutant VDR transgenes were targeted to the keratinocytes of VDR null mice. Keratinocyte-specific expression of a VDR transgene with a mutation in the hormone binding domain that abolishes ligand binding restores normal hair cycling in VDR null mice, whereas a VDR transgene with a mutation in the activation function 2 domain that impairs nuclear receptor co-activator recruitment results in a partial rescue. Mutations in the nuclear receptor co-repressor Hairless are also associated with alopecia in humans and mice. Hairless binds the VDR, resulting in transcriptional repression. Neither VDR mutation affects Hairless interactions or its ability to repress transcription. These studies demonstrate that the effects of the VDR on the hair follicle are ligand independent and point to novel molecular and cellular actions of this nuclear receptor (Kristi Skorija, et. al, Molecular Endocrinology 19: 855-862, 2005).

Previous reports have described the effects of vitamin D on hair follicles. Topical pretreatment of VD3 enhanced hair regrowth in a mouse model of chemotherapy-induced alopecia [Paus R, et. al, Cancer Res 1996; 56:4438-4443). Nuclear vitamin D receptor (VDR)-null-mutant mice were reported to develop alopecia and poor whiskers, although they had normal hair until weaning after birth [Li Y C, et. al, Proc Natl Accad Sci USA 1997; 94: 9831-9835). This suggests that such mice can develop a normal first coat of hair but cannot regulate postnatal hair cycles. In humans, mutations in the VDR coding gene are known to cause hereditary vitamin D resistant rickets with alopecia [Miller J, et. al, J Invest Dermatol 2001; 117:612-617: Zhou Y, et. al, J Bone Miner Res 2009; 24: 643-651]. Furthermore, it has been shown that VDR maintains hair follicle homeostasis that is ligand-independent and suggest that recruitment of novel nuclear receptor co-modulators by the VDR is required for maintenance of hair follicle homeostasis (K. Skorija, et. al, Mol. Endocrinol. 19 (4) (2005) 855-862).

A phase I trial of 14 patients failed to show efficacy for topical calcitriol in the prevention of chemotherapy-induced alopecia (Hidalgo M, et. al, et. al: Anticancer Drugs 10:393-395, 1999 A Phase I trial of topical topitriol (calcitriol, 1, 25-dihydroxyvitamin D3) to prevent chemotherapy-induced alopecia. It has been suggested vitamin $D_3$ resistance may also play a role in alopecia. (Hochberg Z, et. al, Am J Med 77:805-811, 1984).

The Global Burden of Disease (GBD) Study 2010 ((Roderick J Hay, ET. AL, Journal of Investigative Dermatology (28 Oct. 2013) estimated the GBD attributable to 15 categories of skin disease from 1990 to 2010 for 187 countries. At the global level, skin conditions were the fourth leading cause of nonfatal disease burden. Using more data than has been used previously, the burden due to these diseases is enormous in both high- and low-income countries. These results argue strongly to include skin disease prevention and treatment in future global health strategies as a matter of urgency.

Circulating 1,25 dihydroxy D3, bound by DBP (D binding protein), can be delivered systemically to vitamin D target cells that retain the hormone through expression of the nuclear vitamin D receptor (VDR). Intestinal epithelial cells and osteoblasts represent primary sites of VDR (Vitamin D Receptor) expression, where the receptor mediates the actions of 1,25 dihydroxy D3 to promote intestinal calcium and phosphate absorption, and to remodel skeletal mineral, respectively (Haussler, et al. 2013, *Calcif Tissue Int*, 92:77-98). When occupied by 1,25D, VDR interacts with the retinoid X receptor (RXR) to form a hetero dimer that binds to vitamin D responsive elements in the region of genes directly controlled by 1,25D. By recruiting complexes of either co-activators or co-repressors, ligand-activated VDR-RXR modulates the transcription of genes encoding proteins that promulgate the traditional functions of vitamin D, including signaling intestinal calcium and phosphate absorption to effect skeletal and calcium homeostasis. The disease targets, envisioned for vitamin D analogs, appropriately, include osteoporosis by bone-mineral mobilization, secondary hyperparathyroidism to reduce PTH gene transcription and blocking chief cell hyperplasia, autoimmune diseases such as psoriasis and asthma, organ-transplant rejection, benign prostate hyperplasia, involuntary bladder control, blood pressure control by suppressing renin biosynthesis, type 1 diabetes and insulin secretion by affecting pancreatic cell function, anti-inflammatory events via cyclooxygenase-2 (COX-2) inhibition, and cancer via the established anti proliferative and pro differentiating effects on a variety of cell lines, such as breast, prostate and colon. (Pike, et al., 2012, *Rev Endocr Metab Disord*, 13:45-55).

In this fashion, 1,25 dihydroxy D3 elicits its two major functions of preventing rickets in children and osteomalacia in adults, as well as strengthening bone via remodeling. Thus, although vitamin D has no direct role in bone calcification it is responsible for supplying adequate amounts of calcium and phosphorus minerals.

Extra renal 1,25 dihydroxy Vitamin $D_3$ can also be produced locally in a number of cell types that express VDR, notably skin, cells of the immune system, colon, pancreas, and the vasculature. The significance of local effects of 1,25 dihydroxy $D_3$-VDR is not defined fully, but it appears that vitamin D, likely cooperating with other regulators, exerts immuno regulation, antimicrobial defense, xenobiotic detoxification, anti-cancer actions, control of insulin secretion and cardiovascular benefits. (Hussler, et al. 2013, *Calcif Tissue Int*, 92:77-98).

1,25-dihydroxycholecalciferol, i.e., calcitriol, the biologically active form of vitamin D is a secosteroid that acts through binding to the VDR inside cells. VDRs have been suggested to reside in the cytoplasm and in the nucleus without hormone in an unbound state. The VDR binds several forms of cholecalciferol; however, its affinity for 1,25-dihydroxycholecalciferol is roughly 1,000 times that of 25-hydroxycholecalciferol. (Hewisson, et al., 2012, *Plos One, Volume* 7, Issue 1, e30773).

Calcitriol, the active hormonal form of vitamin D, also acts through the VDR to regulate important functions, such as cellular proliferation and differentiation and immune functions. Calcitriol has biphasic effects on cell growth, where physiological doses stimulate cell proliferation, and high pharmacological doses inhibit cell growth. Calcitriol and its derivatives are thought to have utility in the treatment of cancers by retarding tumor growth, inducing apoptosis, and stimulating the differentiation of malignant cells. Current calcitriol derivatives are administered in large dosages to inhibit cancer growth. Unfortunately, such large dosages result in toxic levels of serum calcium.

Further, the therapeutic possibilities of 1,25-dihydroxycholecalciferol are severely limited by the potent effect of this hormone on calcium metabolism, since serious side effects due to hypercalcemia will result from the high doses necessary to obtain a therapeutic effect on, for example, psoriasis, cancer or immunological disorders. To inhibit cell growth, current methodologies utilize combinations of vitamin D derivatives and therapies that specifically alleviate calcemic toxicities incurred by such high pharmacological dosages.

Vitamin D and its analogues, while potentially useful in retarding abnormal cellular proliferation or tumor growth, have the disadvantage of being potent calcemic agents that cause elevated blood calcium levels by stimulating intestinal calcium absorption and bone calcium resorption. Accordingly there is a need for a selective molecular modifications of vitamin D to balance the potential function as a nuclear receptor agonist, antagonist or reverse agonist, and at the same time maintain tissue specificity and sufficient metabolic stability with a constant look out for hypercalcemia and hypophoosphatemia. Therefore, the current focus is directed toward new vitamin D derivatives or analogs with weak calcemic effects and a wide therapeutic window. This and other objects and advantages, as well as additional inventive features, will be apparent from the detailed description provided herein to one of skill in the art.

Compounds which have VDR like activity are known in the art, and are described in numerous United States patents and in scientific publications as agonists and as antagonists; Cited patents include as Agonist (U.S. Pat. No. 6,689,922, U.S. Pat. No. 7,101,865, U.S. Pat. No. 7,595,345, U.S. Pat. No. 7,566,803, U.S. Pat. No. 7,659,296, U.S. Pat. No. 7,750,184) and as Antagonists U.S. patent application Ser. No. 10/481,052, U.S. Pat. No. 7,361,664, U.S. Pat. No. 7,915,242, U.S. patent application Ser. No. 12/266,513, U.S. patent application Ser. No. 10/774,843). It is generally known and accepted in the art that VDR like activity is useful for treating mammals, including humans, to cure or alleviate the symptoms associated with numerous diseases and conditions.

VDR ligands (vitamin D and its derivatives) are known to have broad activities, including effects on cell proliferation and differentiation, in a variety of biological systems. This activity has made Vitamin D derivatives useful in the treatment of a variety of diseases, including dermatological disorders and cancers. The prior art has developed a large number of chemical compounds that have Vitamin D-like biological activity, and voluminous patent and chemical literature exists describing such compounds. (Schrager, et al. 2009, *JABFM*, 9, Vol. 22, No. 6).

The importance of VDR has been shown by Ramagopalan et al. (2010: *Genome Research*, 20:1351) by isolating fragments of genomic DNA bound to the VDR before and after treatment of cells with calcitriol, and then sequenced the DNA fragments. By mapping the sequences back to the genome, they identified more than 2,700 sites of VDR binding, a number that shows just how important vitamin D is to humans, and the wide variety of biological pathways that vitamin D plays a role in.

While the discovery of agonist or even "super agonist" activity is known, ligands that selectively stabilize an antagonistic conformation of the VDR LBD within the VDR-RXR-DVRE construct, to prevent induction of transactivation, are also of potential therapeutic value. The degree of affinity of a vitamin-D analog to the VDR appears to be of lesser importance than its alignment with specific contact sites in the ligand binding domain to produce different VDR conformations with modified transcriptional consequences. There are a reported 3000 vitamin D related compounds that have already been synthesized, with the goal to minimize or eliminate hyper calcemic side effects while maintaining sustained plasma levels, the desired transactivation potencies and cell specificities. Many vitamin D analogs that circumscribe the binding affinity and determine its function as agonist or antagonist, the disease modifying potential and, eventually, the inherent clinical value.

Unfortunately, compounds having Vitamin D like activity (e.g.; calcitriol) also cause a number of undesired side effects at therapeutic dose levels, including hypercalcemia. These side effects limit the acceptability and utility of vitamin D for treating diseases. There are no known inverse agonists of VDR and Metadichol® is the first of its kind.

SUMMARY OF THE INVENTION

The compounds of the present invention are useful for preventing certain undesired side effects of Vitamin D which are administered for the treatment or prevention of certain diseases or conditions.

The present invention additionally relates to the use of vitamin D receptor (VDR) inverse agonists in binding to receptor sites in biological systems, including mammals, to maintain a basal level of activity on said receptor sites.

In one particular aspect of the present invention, there is provided a method of treating a pathological condition in humans. The conditions treated are associated with a VDR receptor activity. This method involves administering to humans a VDR inverse agonist capable of binding to a VDR receptor or its subtypes: The inverse agonist is administered in an amount pharmaceutically effective to provide a therapeutic benefit against the pathological condition in the mammal.

The VDR inverse agonist can be administered to humans internally, i.e., Intra-gastric intubation or food or water admixture, or parentally, e.g., intra-peritoneal, intra-muscularly, subcutaneously, and in addition as a gel which can be applied topically to treat various skin ailments and diseases.

In one particular aspect of the invention for topical applications a clear gel was made by treating Metadichol® with any one of one of the commercial available like, Carbopol® Polymer (Registered trade mark of Lubrizol) polyethylene oxide (PEO) (polyvinyl pyrollidone (PVP)), polylactic acid (PLA) (, polyacrylic acid (PAA) polymethacrylate (PMA) polyethylene glycol (PEG) or natural biopolymers, such as alginate, chitosan, carrageenan, hyaluronan, and carboxymethyl cellulose (CMC).

The gel in this example and its applications was made by rapid stirring and mixing at 30-35 C, 0.5%-1% of the liquid Nano particle described earlier (U.S. patent application Ser. No. 12/691,706) with 0.5% to 1% by weight of Carbopol® a (Lubrizol Corporation Pharmaceutical bulletin 22 Edition: May 31, 2011) and resulted in a clear gel containing 0.5-1% of active Nano particle ingredient ready for topical use.

The only requirement for the route of administration is that it must allow delivery of the agonist to the target tissue through Oral or topically using the gel. The VDR inverse agonist is formulated in combination with excipients.

DETAILED DESCRIPTION OF THE INVENTION AND THE PREFERRED EMBODIMENTS

Introduction

Figure 1:
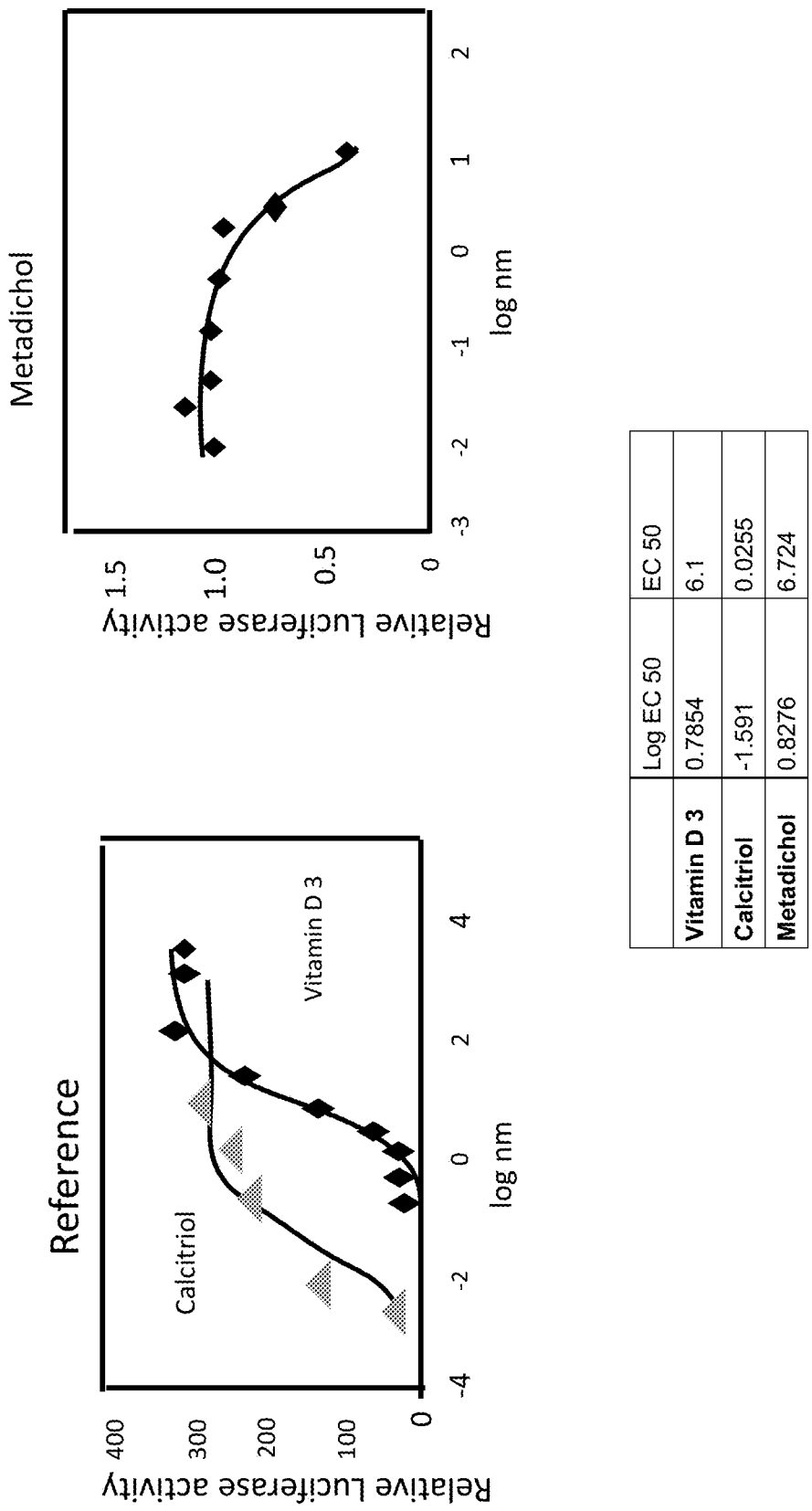
FIG. 1 shows the results of the VDR transactivation assay of the test compound relative to all 1,25, dihydroxy vitamin $D_3$ (the natural agonist) and Vitamin D for certain exemplary compound of the invention.

The present invention provides Metadichol® a novel VDR inverse agonist. This type of receptor is one of the most important targets of the pharmaceutical industry, and many of the drugs with significant therapeutic action have been shown to be inverse agonists. The VDR inverse agonists provided herein have been demonstrated to bind to VDRs with good affinity. Further, the inverse agonists can, by binding with Vitamin D receptor, regulate gene transcription and cell growth.

Metadichol® is more likely based on the results that we describe as a protean agonist. The word protean is derived from the Proteas the Greek who could change shape. This concept was proposed by Kenakin, et. al, (FASEB J. 2001, March: 15(3): 598-611) and was demonstrated by Gbahou. et. al, (Proc. Natl. Acad. Sci. (USA) 2003, 100, 11086-11091) with $H_3$ histaminic receptors. According to this concept GPCRs are allosteric Proteins that adopt inactive and active conformations. In equilibrium the active form of receptor can occur spontaneously leading to constitutive activity. An agonist may also promote it. Inverse agonists promote inactive form of receptors and decrease constitutive activity. The rationale behind protean agonism is that if an agonist produces an active state of lower efficacy than the constitutively formed one, the ligand would act as an inverse agonist. However, in the absence of constitutive activity, the ligand would be converted to an agonist.

In the unbound state a receptor is functionally silent, and this is true in most cases. However, some receptor systems display constitutive activity, either experimentally as a result of over expression or as a result of mutation. These receptors are active in absence of agonist. An inverse agonist would inhibit this constitutive activity. Recent studies have demonstrated intriguing actions of inverse agonists. (IJzerman, et al., 2000, *British Journal of Pharmacology*, 130:1-12). They have been shown not only to block constitutive responses of receptors but also to activate and regulate seven-trans membrane receptor signaling and trafficking. (Dupré, et al., 2004, *Biochem. Cell Biol.*, 82(6):676-680. A receptor is said to be constitutive active, if the receptor activates and functions by itself without a ligand.

Basal receptor signaling denotes a state of constant low-level activity of a receptor. It is mainly seen in case of receptors that enable survival. For example, growth hormone receptor has a basal level of activity that depends on the presence of a low level of ligand, like the growth hormone and insulin like growth hormone, in the blood. The removal of this activity causes cell death. Thus there should be a basal level of receptor activity for the cells to survive. The advantage of basal receptor activity and constitutive activity is that the control of cell having such receptors can be more precise.

For example, if the function of a cell has to be decreased, the body can secrete an inverse agonist, in case of constitutively active receptor, or decrease the production of the ligand for basally active receptors. Because the receptors are basally active, the control can be either negative and/or positive i.e. in both directions. (Ijzerman, 2006, Trends Pharmacol Sci, 27:92-6).

These inverse agonists can be used for the treatment of abnormal cell growth, such as cancer, and the prevention of recurrent cancers. One preferred embodiment of the invention utilizes the VDR inverse agonist for the therapeutic treatment of elevated PSA levels, in reducing ferritin levels, in reducing RDW red cell distribution width, in increasing Apo (a) and reducing APO (b) protein levels in hyperlipidemia, treating MDS (myelodysplacia syndrome) patients, increasing Hemoglobin and platelet counts and normalizing Neutrophils, lymphocytes, and monocytes, and in reducing uric acid and Lipoprotein (a) levels, and reducing TSH levels (thyroid stimulating hormone) (and thyroid globulin antibody (TgAb) and thyroid peroxidase antibody (TPOAb) levels that are seen in Graves and Hashimoto diseases and other autoimmune diseases) and in high reducing high levels of bilirubin and in regulating parathyroid hormone and normalizing Calcium and Phosphorus and Potassium levels in kidney patients. The VDR inverse agonists of the invention can also be used for the therapeutic treatment and/or prophylactic prevention of other types of conditions or diseases, such as, but not limited to, rheumatoid arthritis, bone marrow disease, prostate cancer, colorectal cancer, leukemia, brain cancer, primary or metastatic melanoma, glioma, primary hyperparathyroidism, psoriasis, kidney stones, and infections diseases (e.g., malaria). Furthermore, since these derivatives inhibit parathyroid hormone secretion, they are contemplated to be effective for the treatment of secondary hyperparathyroidism that causes bone disease and vascular calcification in patients suffering from renal failure.

DEFINITIONS

Unless defined otherwise, all technical and scientific terms used herein generally have the same meaning as commonly understood by one of ordinary skill in the art to which this invention belongs.

The methods and formulations may be used for prophylactic or therapeutic purposes. In some embodiments, the terms "treating" or "treatment" of any disease or disorder refers to ameliorating the disease or disorder (i.e., arresting or reducing the development of the disease or at least one of the clinical symptoms thereof). In other embodiments, "treating" or "treatment" refers to ameliorating at least one physical parameter, which may not be discernible by the subject. In yet other embodiments, "treating" or "treatment" refers to inhibiting the disease or disorder, either physically, (e.g., stabilization or eradication of a discernible symptom), physiologically, (e.g., stabilization or eradication of a physical parameter) or both. In still other embodiments, "treating" or "treatment" refers to delaying the onset of the disease or disorder.

Therapeutically effective amount" is used interchangeably herein with "an amount effective to," when referring to a method of the invention. When used in reference to a Metadichol® dosage, these terms refer to a dosage that provides the specific pharmacological response for which the policosanol is administered in a significant number of subjects in need of such treatment. It is emphasized that "therapeutically effective amount," administered to a particular subject in a particular instance may not be effective for 100% of patients treated for a specific disease, and will not always be effective in treating the diseases described herein, even though such dosage is deemed a "therapeutically effective amount" by those skilled in the art. It is to be further understood that policosanol dosages are, in particular instances, measured as oral dosages, or with reference to drug levels as measured in blood. As used herein, the terms "individual," "subject," and "patient," is used interchangeably to refer to an animal, e.g. a mammal, e.g., a human.

The Compositions
Metadichol® Nano Gel

An aging population in the developing world has led to an increase in musculoskeletal diseases such as osteoporosis and bone metastases. Left untreated, many bone diseases cause debilitating pain and in the case of cancer, death. Many potential drugs are effective in treating diseases but result in side effects preventing their efficacy in the clinic. Bone, and skin however, provides a unique environment of inorganic solids, which can be exploited to effectively target drugs to diseased tissue. By integration of bone targeting moieties to drug-carrying water-soluble polymers, the payload to diseased area can be increased while side effects decreased.

Nanometer-sized polymeric hydrogels, Nano gels, or hydrogel Nano particles (NPs; size from 1 to 1000 nm) are swollen networks composed of amphiphilic or hydrophilic poly ionic polymers, either natural or synthetic. Nano gels are promising multifunctional polymeric NPs with potential as delivery systems because of their unique properties. These include tunable chemical and physical structures, flexible Nano size, large surface area for multivalent conjugation, high water content, biocompatibility, loading capacity, stability, ability to target specific cells and specific cell compartments, immune modulatory properties, and responsiveness to environmental factors. (Oh J K, et al., *Prog Polym Sci,* 2009, 34:1261-82; Oh J K., et al. 2010, *Can J Chem,* 88:173-84; Hubbell J A, et al., *Nature,* 2009, 462:449-60).

As Nano carriers must be delivered to specific sites upon injection into body fluids, the possibility of modulating the chemical and physical properties of NPs could be most helpful in overcoming major biological barriers such as the reticuloendothelial system, clearance through kidney glomeruli, and nonspecific accumulation in different organs. Nano gels are still a new and rapidly developing group of materials, gaining wide application in many fields, especially pharmacy, medicine and agriculture. An exemplary hydrogel is a material made when a water-insoluble polymer absorbs a large amount of water, or it is simply a water-swollen polymer network.

The terms gels and hydrogels are used interchangeably by food and biomaterials scientists to describe polymeric cross-linked network structures. Although the water content in hydrogels may be as little as a few percent to over 99%, hydrogels retain the properties of solids (Truong N., et al., 2002, *Biomaterials,* 23:4307, Glyn O Phillips, et al., 2011, Hydrogels: Methods of Preparation, Characterization and Applications, Progress in Molecular and Environmental Bioengineering—From Analysis and Modeling to Technology Applications, *Angelo Carpi (Ed.),* ISBN: 978-953-307-268-5, InTech).

Due to their high water absorption capacity and biocompatibility these gels have been used in wound dressing, drug delivery, agriculture, sanitary pads as well as trans-dermal systems, dental materials, implants, injectable polymeric systems, ophthalmic applications, hybrid-type organs (encapsulated living cells (Table 1 below) They are used in wound care, in drug delivery, dental materials, tissue engineering implants and injectable polymeric systems to name a few. (Vinogradov S V, et al., 2009, *Angew. Chem. Intern. Ed.,* 48:5418-5429).

TABLE 1

| Therapeutic Moieties | Polymer |
| --- | --- |
| Insulin | Tri polymer of N-vinyl pyrrolidone methacrylamide and itaconic acid |

TABLE 1-continued

| Therapeutic Moieties | Polymer |
| --- | --- |
| Caffeine | Poly dimethyaminoethylmethyacrylate |
| Camptothecin | polyethylene glycol |
| Calcitonin | copolymer of polymethylacrylic acid and polyethylene glycol |
| Ketoprofen | Copolymer of cationic guar gum and acrylic acid polymer |
| Human Growth Hormone | Poly organophosphazene with alpha-amino omega methyl polyethylene glycol |
| Adenochrome (Blood coagulating agent) | Copolymer of poly-PNIPA and poly PNIPA-Co-AA |
| Proteins and peptide | Polyepsilon caprolactone-co-lactide-polyethylene glycol: Chitosan |
| 5-Fluouracil | Co-polymer of poly-PNIPA and poly-PNIPA-Co-AA |
| Insulin | NIPAAm-Co-AAm |
| Vaginal Microbicide | NIPAAm-Co-AAm |

Nano gels have found applications in several fields such as sensing diagnostics and bioengineering, but its greatest impact has been in the area of drug delivery. Nano gels and other Nano-sized drug delivery systems have several advantages over macro-sized ones. Nano gels can also be inherently useful in systems that require a burst release. Nano systems, unlike bulk drug delivery systems, can enter cells to deliver drugs and can be designed to respond to intracellular cues. (S. Thayumanavan, et al. 2912, Advanced Drug Delivery Reviews, 64, 836-851).

The tables below show some applications of hydrogel in therapeutics. (Kohli, et al., *Scientific Research and Essay,* 2009, 3(11):1175-1183).

Dispersed in aqueous media, swollen Nano gel networks are soft and can encapsulate a considerable volume of water. Biological agents and drugs can be loaded into Nano gels via a spontaneous process including interactions between the agent and the polymer matrix, forming hydrophilic particles with high dispersion stability. Nano gels are able to physically protect biological molecules from degradation in vivo and have been pre-clinically investigated for many types of active molecules, ranging from small drugs to bio-macromolecules. The water holding capacity and permeability are the most important characteristic features of a hydrogel (S. Vinogradov, et al., *Nanomedicine,* 2010, 166, 5(2)).

Accordingly, the present invention provides a compound or formula as described in U.S. patent application Ser. No. 12/691,706 published Aug. 26, 2010 and as a polymeric hydrogel formulation for skin and topical applications. Described herein are compositions and methods for preventing and/or treating skin diseases including, but not limited to, psoriasis MRSA infections, and atopic dermatitis as well as providing anti-aging benefits which results in reduced appearance of wrinkles and aged skin, improved skin color, treatment of photo damaged skin, growing hair, improvement in skin's radiance and clarity and finish, and an overall healthy and youthful appearance of the skin, involving aberrant angiogenesis and hyperplasia employing the said formulation.

Biological Activity, Modes of Administration

As noted above, the compounds of the present invention are inverse agonists of the VDR receptor. This means that the compounds of the invention bind to the same site as the natural receptor 1,25 dihydroxy vitamin $D_3$. Depending on the site and nature of undesirable side effects, which are ideally suppressed or ameliorated, compounds used in accordance with the invention may be inverse agonists of VDR receptor.

A compound should not cause significant activation of a reporter gene through a VDR receptor in the transactivation assay in order to qualify as a VDR inverse agonist with utility in the present invention. Last, but not least, a compound should bind to VDR receptor subtypes in the ligand binding assay in order to be capable of functioning as an inverse agonist of the bound receptor subtype, provided the same receptor is not significantly activated by the compound.

VDR Transactivation Assay

The VDR assay was carried out as described in the VDR assay kit supplied by Indigo Biosciences Inc. College Town Pa.). All appropriate controls and standards as specified by the manufacturer's kit were used. The procedures are described by Vanden Heuve, et al., *PPAR Res,* 2006, 69612; Vanden Heuve, *Toxicol Sci,* 92:476-489.

The Antimalarial activity was carried using an adaptation of the procedures described by Desjardins et al. (Antimicrob. Agents Chemother. 16, 710-718, 1979); Matile and Pink (In: Lefkovits, I. and Pernis, B. (Eds.) Immunological Methods Vol. IV, Academic Press, San Diego, pp. 221-234, 1990).

Figure 2:
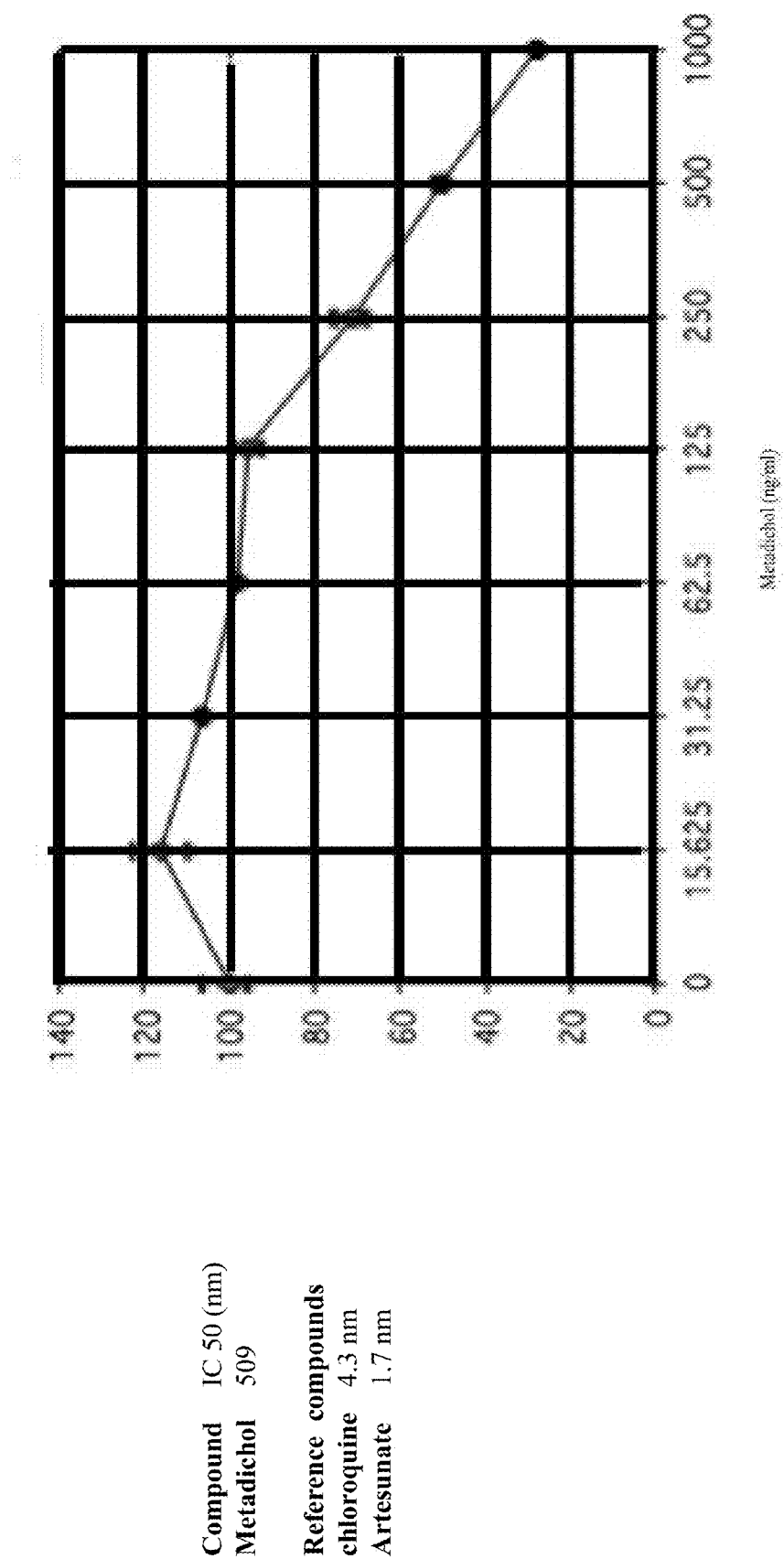
FIG. 2 shows results of the malaria assay.

FIG. 1 shows the results of the VDR transactivation assay of the test compound relative to all 1,25 dihydroxy vitamin D3 (the natural agonist) and Vitamin D for certain exemplary compound of the invention. FIG. 2 shows the results of in vitro assay of Metadichol® against A strain of *P. falciparum* used in this experiment is the drug-sensitive NF54 (an airport strain of unknown origin) VDR transactivation assay.

Procedure

Plasmids. The ligand-binding domain of the nuclear receptors was fused to the DNA-binding domain of the yeast transcription factor Gal4 under the control of the SV40 promoter. A reporter plasmid encodes the firefly luciferase gene under the control of the Gal4 DNA response element (UAS). A transfection efficiency control vector is included in most assays (pRL-luciferase, Promega, Madison, Wis.). All plasmids were verified by sequencing and through examination of positive controls. (Tien, et al., 2006; Vanden Heuvel, et al., 2006) Full.

Length System. The full-length cDNA of the nuclear receptor is under the control of the SV40 promoter. A reporter plasmid encodes the luciferase reporter under the control of the MMTV response element. All plasmids were verified by sequencing and through examination of positive controls.

Cell Culture and Transactivation Assays

HEK 293-T fibroblasts (ATCC, Manassas, Va.) were cultured in high glucose Dulbecco's Minimal Essential Medium (DMEM) supplemented with 10% fetal bovine serum (FBS, Sigma), 0.2 mg/ml streptomycin and 200 U/ml penicillin (Gibco, Grand Island, N.Y.). For transient transfection reporter assays, HEK 293-T ells were transfected with plasmid DNA using Lipofectamine reagent (Invitrogen, Carlsbad, Calif.) and following the manufacturer's recommended procedures, using HEK 293-T cells at approximately 80% confluence in 10 cm culture dishes. After 6 h, the DNA-Lipofectamine complex was removed Following overnight culture, the media was replaced 4 h after repeating with DMEM (10% FBS) containing test compounds in DMSO (0.1% final concentration). Concentrations of the chemicals are given in the figure legends. Sixteen hours after treatment, the cells were lysed with passive lysis buffer (Promega, Madison, Wis.) for 30 min; luciferase activity was measured using the Luciferase dual reporter assay kit (Promega, Madison, Wis.) and a Tecan GeniosPro (Research Triangle Park, N.C.) and manufacturer's recommended procedures. The fold induction of normalized luciferase activity was calculated relative to vehicle-treated cells, and represents the mean of three independent samples per treatment group.

Malaria: In Vitro Screening Procedure

Parasite cultures; A strain of *P. falciparum* used in this experiment is the drug-sensitive NF54 (an airport strain of unknown origin) The strains are maintained in RPMI 1640 medium with 0.36 mM hypoxanthine, supplemented with 25 mM N-2-hydroxyethylpiperazine-N'-2-ethane-sulphonic acid (HEPES), 25 mM $NaHCO_3$, neomycin (100 U/ml) and 5 g/l of Albumax® II (lipid-rich bovine serum albumin, GIBCO, Grand Island, N.Y., USA), together with 5% washed human A+ erythrocytes. All cultures and assays are conducted at 37° C. under an atmosphere of 4% $CO_2$, 3% $O_2$ and 93% $N_2$. Cultures are kept in incubation chambers filled with the gas mixture. Subcultures are diluted to a parasitemia of between 0.1 and 0.5% and the medium is changed daily.

Drug Sensitivity Assays

Antimalarial activity is assessed using an adaptation of the procedures described by Desjardins et al. (Antimicrob. Agents Chemother. 16, 710-718, 1979), and Matile and Pink (In: Lefkovits, I. and Pernis, B. (Eds.) Immunological Methods Vol. IV, Academic Press, San Diego, pp. 221-234, 1990).

Stock drug solutions are prepared in 100% dimethyl-sulfoxide (DMSO) (unless otherwise suggested by the supplier) at 10 mg/ml, and heated or sonicated if necessary to dissolve the sample. After use the stocks are kept at −20° C. For the assays, the compound is further diluted in serum-free culture medium and finally to the appropriate concentration in complete medium without hypoxanthine. The DMSO concentration in the wells with the highest drug concentration does not exceed 1%.

Assays are performed in sterile 96-well micro titer plates, each well containing 200 µl of parasite culture (0.15% parasitemia, 2.5% hematocrit) with or without serial drug solutions. Seven 2-fold dilutions are used, covering a range from 5 µg/ml to 0.078 µg/ml. For active compounds the highest concentration is lowered (e.g. to 100 ng/ml); for plant extracts the highest concentration is increased to 50 µg/ml. Each drug is tested in duplicate and the assay is repeated for active compounds showing an $IC_{50}$ below 1.0 µg/ml. After 48 hours of incubation at 37° C., 0.5 µCi·$^3$H-hypoxanthine is added to each well. Cultures are incubated for a further 24 h before being harvested onto glass-fiber filters and washed with distilled water. The radioactivity is counted using a Betaplate™ liquid scintillation counter (Wallac, Zürich, Switzerland). The results are recorded as counts per minute per well at each drug concentration and expressed as percentage of the untreated controls. $IC_{50}$ values are calculated from the sigmoidal inhibition curves using Microsoft EXCEL).

The Compositions

In various embodiments, the invention provides Metadichol® as a liquid or as gel which is a Nano formulation of Policosanol described in U.S. patent application Ser. No. 12/691,706.

Composition of Gel

The polymer used is derived from one of the following: Carbopol® Polymer (Registered trade mark of Lubrizol) polyethylene oxide (PEO) (polyvinyl pyrollidone (PVP)), polylactic acid (PLA) (polyacrylic acid (PAA) polymethacrylate (PMA) polyethylene glycol (PEG) (Singh et al.), or natural biopolymers, such as alginate, agar, chitosan, carrageenan, hyaluronan, and carboxymethyl cellulose (CMC).

In an exemplary embodiment, the unit dosage gel formulation is a formulation of Nano particleNano particles containing Metadichol® and a stabilizer fraction and the unit dosage formulation includes from about 10 mg to about 100 mg, for example from about 1 mg to about 20 mg per mL or from about 10 mg to about 30 mg per mL. In various embodiments, the unit dosage is a daily dosage. One of ordinary skill will appreciate that therapeutically effective amounts of Metadichol® gel can be determined empirically and can be employed in pure form or, where such forms exist, in pharmaceutically acceptable salt, ester, or pro-drug form. Actual dosage levels of Metadichol® in the Nano particulate compositions of the invention may be varied to obtain an amount of Metadichol® that is effective to obtain a desired therapeutic response for a particular composition and method of administration. The selected dosage level therefore depends upon the desired therapeutic effect, the route of administration, the potency of the administered policosanol, the desired duration of treatment, and other factors.

Dosage unit compositions may contain such amounts of such submultiples thereof as may be used to make up the daily dose. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex, and diet of the patient; the time of administration, route of administration, and rate of excretion of the agent; the duration of the treatment; drugs used in combination or coincidental with the specific agent; and like factors well known in the medical arts.

The Methods

The present invention provides methods of using these Nano particles of Metadichol® in liquid or gel form and prevent disease and to regulate metabolism. In various embodiments, the Nano particleNano particles of the invention in liquid form are of use to regulating, Lp (a), Apo (a) and Apo (b) protein levels, Uric acid, Parathyroid hormone levels, decreasing bun ratios in kidney patients, Regulating Phosphorous and Calcium levels, Potassium levels in hypertension patients, Ferritin levels, TSH levels, neutropenia, modulating aspartate aminotransferase (AST) or serum glutamic-oxaloacetic transaminase [SGOT]), alanine aminotransferase (ALT) or serum glutamate pyruvate transaminase [SGPT]), levels, modulating absolute neutrophil and Lymphocyte ratios and modulating albumin in hyperlipidemia patients.

The Metadichol® gel formulations is topically used in treating various skin diseases like acne, MRSA infection, Eczema, Psoriasis, and preventing and/or treating skin diseases including, but not limited to, psoriasis and atopic dermatitis as well as providing anti-aging benefits which results in reduced appearance of wrinkles and aged skin, improved skin color, treatment of photo damaged skin, improvement in skin's radiance and clarity and finish, and an overall healthy and youthful appearance of the skin, involving aberrant angiogenesis and hyperplasia.

In an exemplary embodiment, the formulations are administered in a therapeutically effective amount to a subject to treat a particular disease or disorder and wherein the subject is not otherwise in need of treatment with Metadichol®. In various embodiments, the Metadichol® is administered to treat a single disease or regulate a single metabolic factor. Thus, in an exemplary embodiment, the invention provides a method to treat Lipoprotein (a) in a subject not in need of treatment for hyperlipidemia, hypercholesterolemia, hypertension, etc. In an exemplary embodiment, the invention provides a method of regulating parathyroid hormones levels in a subject not in need of treatment for kidney disease, hyperlipidemia, hypercholesterolemia, etc. In various embodiments, the invention provides a method of treating Potassium levels in a subject not in need of treatment for hypertension, diabetes etc. In various embodiments, the invention provides a method to decrease or prevent neutropenia in a subject who is not in need of treatment for kidney diseases, Inflammation etc., In an exemplary embodiment, the invention provides a method of increasing Apo Protein (a) levels in a subject not in need of treatment for hyperlipidemia, hypercholesterolemia, etc. In other embodiments, the invention provides a method of modulating AST and ALT levels in a subject not in need of treatment for hyperlipidemia, hypercholesterolemia, etc.

In various embodiments, the Metadichol® gel is used in Eczema, Psoriasis, Lipoma tumors on removing wrinkles and warts and in MRSA and other skin infections.

Non-limiting examples of methods of the invention are set forth below:

Uric Acid

The invention provides a method of decreasing Uric acid levels in a subject and, therefore, reducing the deleterious consequences of this oxidation. The method includes administering to a subject a therapeutically effective amount of Metadichol® to decrease protein oxidation in a subject.

Uric acid is present in small amounts in everyone's bodies and is made from the breakdown of purines, which are released as part of the body's normal functioning and can be absorbed by the body from certain types of food (such as meat or seafood). In addition a number of epidemiological studies have reported a relation between serum uric acid levels and a wide variety of cardiovascular conditions, including hypertension, (Acosta, et al. 2005, *J Am Soc Nephrol*, 16,909-1919; Heinig M, et al. 2006, *Cleveland Clinic Journal of Medicine*, 73(12):1059-64).

Uric acid may play a role in the metabolic syndrome. Historically, the elevated level of uric acid observed in the metabolic syndrome has been attributed to hyperinsulinemia, since insulin reduces renal excretion of uric acid. Hyperuricemia, however, often precedes the development of hyperinsulinemia, obesity, and diabetes. Hyperuricemia may also be present in the metabolic syndrome in people who are not overweight or obese. (Tyagi, et al., *Nutrition & Metabolism*, 2004, 1:10). Hyperuricemia is strongly associated with peripheral, carotid, and coronary vascular disease, with the development of stroke, with preeclampsia, and with vascular dementia. The relationship of uric acid with cardiovascular events is particularly strong, especially in patients at high risk for heart disease and in women. In coronary artery disease, (Viazzi, et al., 2006, *The Journal of Clinical Hypertension*, 8(7):510).

Serum uric acid is a strong predictor of stroke in patients with non-insulin dependent diabetes mellitus ND cerebrovascular disease, (Puig, et. al., 2007, *Nutrition, Metabolism & Cardiovascular Diseases*, 17, 409e414).

Gout is a type of arthritis caused by uric acid build-up in the joints (the places where two or more bones come together). When uric acid levels in the body are high (known as hyperuricemia), uric acid crystals can form in the fluid around the joints. If there is too much uric acid around the joints, inflammation (a condition in which a part of your body can become red, swollen, and painful) can occur, which may lead to a gout attack (Tausche A K, et al., 2006, *Der Internist*, 47(5):509-20).

Lesch-Nyhan Syndrome

Lesch-Nyhan syndrome, an extremely rare inherited disorder, is also associated with very high serum uric acid levels. Spasticity, involuntary movement and cognitive retardation as well as manifestations of gout are seen in cases of this syndrome. (Nyhan W. L, 2005, *Journal of the History of the Neurosciences*, 14(1):1-10).

Uric Acid Stone Formation

Saturation levels of uric acid in blood may result in one form of kidney stones when the urate crystallizes in the kidney. Uric acid stones, which form in the absence of secondary causes such as chronic diarrhea, vigorous exercise, dehydration, and animal protein loading, are felt to be secondary to obesity and insulin resistance seen in metabolic syndrome. Increased dietary acid leads to increased endogenous acid production in the liver and muscles, which in turn leads to an increased acid load to the kidneys. This load is handled more poorly because of renal fat infiltration and insulin resistance, which are felt to impair ammonia excretion (a buffer). The urine is therefore quite acidic, and uric acid becomes insoluble, crystallizes and stones form. In addition, naturally present promoter and inhibitor factors may be affected. This explains the high prevalence of uric stones and unusually acidic urine seen in patients with type 2 diabetes. Uric acid crystals can also promote the formation of calcium oxalate stones, acting as "seed crystals" (heterogeneous nucleation). (Pak C. Y, et al. 2008; *The Journal of Urology,* 180(3):813-9).

Hyperuricemia has been shown to be associated with histological liver damage in patients with non-alcoholic fatty liver disease (NAFLD). Its clinical relevance arises from the fact that a considerable proportion of subjects (20-30%) develop a condition namely non-alcoholic steatoheppatitis (NASH) that is a potentially progressive hepatic disorder leading to end-stage liver disease and hepatocellular carcinoma. In addition NAFLD is considered the hepatic manifestation of insulin resistance (IR), and is therefore strongly associated with metabolic syndrome, obesity, type II diabetes, dyslipidemia and hypertension, also representing, together with the above cited conditions, an independent cardiovascular risk factor. In these patients. (Non-alcoholic fatty liver disease (NAFLD) is a leading cause of chronic liver disease worldwide. (S. Petta, et al., *Aliment Pharmacol Ther,* 2011, 34:757-766).

Uric Acid and Parkinson's Disease (PD)

PD is the second most common age related neurodegenerative condition in the US, affecting approximately one percent of the population over the age of 65 in North America and Europe. The symptoms of PD are characterized by loss of dopaminergic neurons in the substantia nigra. While the cause of this loss is thought to be multifactorial, there is evidence to support oxidative stress as a factor in neurodegeneration. Researchers have proposed that elevated levels of uric acid yield a protective effect against the development and progression of PD on the basis of these principles. There is also evidence to support the association between high dietary urate and a decreased incidence of PD. It should be noted that there are numerous risks associated with hyperuricemia diets, such as gout, stroke and hypertension. At this point, the data we have suggests an association, but not a causal relationship between low serum urate and the incidence of PD. This association is intriguing as there is the potential that in the future physicians could modify a patient's risk for PD by suggesting dietary changes or using pharmacological supplement. Overall, recent research supports an inverse relationship between serum urate levels and the incidence of PD in men. (Mandel, et al., 2009, *Practical Neurology,* p 21).

Ferritin

Ferritin is a ubiquitous and specialized protein involved in the intracellular storage of iron; it is also present in serum and other biological fluids, although its secretion processes are still unclear. Ferritin is nature's unique and conserved approach to controlled, safe use of iron and oxygen, with protein synthesis in animals adjusted by dual, genetic DNA and mRNA sequences that selectively respond to iron or oxidant signals and link ferritin to proteins of iron, oxygen and antioxidant metabolism. (Cairo, et al. 2008, *Journal of Autoimmunity* 30, 84-89).

Ferritin is a key protein of iron metabolism that is capable of sequestering large amounts of iron, and thus serves the dual function of iron detoxification and iron storage. The importance of these functions is underlined by its ubiquitous distribution in many living species. The structural properties of the ferritins are largely conserved from bacteria to man, although their role in the regulation of iron trafficking varies substantially.

Ferritin synthesis is regulated by cytokines (TNFα and IL-1α) at various levels (transcriptional, post-transcriptional, and translational) during development, cellular differentiation, proliferation, and inflammation. The cellular response by cytokines to infection stimulates the expression of ferritin genes. (Hintze K J, et al., 2006, *Cell Mol Life Sci;* 63:591-600).

Ferritin has been reported to exhibit different immunological activities including binding to T lymphocytes, suppression of the delayed type of hypersensitivity, suppression of antibody production by B lymphocytes, and decreased phagocytosis of granulocytes (Marikina, K, et al., 999, *Blood,* 4 83:737-43).

Ferritin and iron homeostasis have been implicated in the pathogenesis of many diseases, including diseases involved in iron acquisition, transport and storage (primary hemochromatosis) as well as in atherosclerosis, Parkinson's disease, Alzheimer disease, and restless leg syndrome. (Zandman, et al., 2007, *Autoimmunity Reviews,* 6:457-463).

Mutations in the ferritin gene cause the hereditary hyperferritinemia-cataract syndrome and neuroferritinopathy. Hyperferritinemia is associated with inflammation, infections, and malignancies. Thyroid hormone, insulin and insulin growth factor-1 have also been implicated in regulation of ferritin at the mRNA level (Beaumont C, et al., 1995, *Nat Genet,* 11:444-6; Nishiya K, et al., 1997, *Clin Exp Rheumatol,* 15:39-44).

Some evidence points to the importance of hyperferritinemia in RA, MS, and thyroiditis, Ferritin and iron homeostasis have been implicated in the pathogenesis of many diseases, including diseases involved in iron acquisition, transport and storage (primary hemochromatosis) as well as in atherosclerosis (You S. A, et al., 2005, *Clin Chim Acta,* 357:1-16). Genetic mutations of the ferritin IRE region as well as coding regions of ferritin cause some hereditary human diseases. Ferritin IRE mutations cause the hereditary hyperferritinemia-cataract syndrome (Beaumont C, et al., 1997; *Nat Genet,* 11:444-446) which is an autosomal dominant disease characterized by elevated ferritin levels and early-onset bilateral cataracts.

Neuroferritinopathy, a dominantly inherited movement disorder characterized by decreased levels of ferritin and abnormal deposition of ferritin and iron in the brain, is caused by a mutation in the C-terminus of the ferritin L gene (Curtis A R J, et al., 2001, *Nat Genet,* 28:350-4). It has been shown that Serum ferritin concentration was found to be related with dyslipidemia, hypertension and abdominal adiposity. Ferritin is also known to be a marker of inflammation and increases in cardiovascular disease and it has been suggested that serum ferritin levels can be used as a risk marker for atherosclerotic disease (Faruk, et al. 2006; *Endocrine Abstracts,* 11 P323).

Thalassemia will remain to be the one of the major health problem for at least the next few decades, particularly in developing countries. Although the survival of thalassaemics is steadily increasing, the prevalence of complications due to Serum ferritin being high. This overload is the life limiting complication commonly found in thalassaemics (Wangruangsattit S, et al., 1999, *J Med Assoc That,* 82(1):74-76). The iron that exceeds the iron binding capacity of transferrin appears in the plasma as non-transferrin bound iron, which is highly toxic to tissues. The accumulation of iron results in progressive dysfunction of the heart, liver and endocrine glands (Hathirat P., et al., 1001, *Hematol,* 2001, 38:360-366).

Ferritin may act as an immune regulator by binding to subsets of lymphocytes and myeloid cells contrasts with its well-known function as an intracellular iron storage protein. Ferritin, which may therefore not only be the major iron storage protein, but also an important regulator of the immune system playing a possible role in autoimmune diseases. (Recalcati, et al., 2008, *Journal of Autoimmunity,* 30:84-89).

Ferritin has been suggested to be a circulating tumor-associated antigen in Hodgkin's disease, Bieber, C. P., et al., 1973, *Nat. Cancer Inst. Monogr.,* 36:147-157; Jones, P. A, et al. (1973, Brit. J. Cancer 27, 212-217).

Although ferritin occurs intracellularly in a wide variety of tissues and its level in the serum of healthy humans is low, it was found in elevated amounts in the serum of patients with Hodgkin's disease as well as in other malignancies and diseases with liver involvement (Aungst, C. W., 1968, *J. Lab. Clin. Med.,* 71:517-522; Reissman, K. R., 1956, *J. Clin. Invest.,* 35:588-595).

Antigens which exist in high frequency in tumor tissues of patients with Hodgkin's disease have been obtained in relatively concentrated form by gel chromatography procedures. Further purification and analysis of these antigens (Eshhar, et al., 1974, *Proc. Nat. Acad. Sci. USA,* 71(10):3956-3960), have demonstrated that the antigen of fast electrophoretic mobility (F-antigen) is normal tissue ferritin.

Lipoprotein A (Lp (a))

First described in 1963 (Berg, 1963, *Acta Pathol Microbiol Scand,* 59:369-82) that Lp(a) is a modified LDL particle. Berg and his colleagues in Sweden later determined that individuals with high levels of Lp(a had significantly higher incidences of heart attacks than a population with low Lp(a). Studies that have detected Lp(a) in atherosclerotic lesions and vein grafts have provided the strongest evidence for a direct involvement of Lp(a) at the lesion site (Walton, K W, et al., 1981, *Atherosclerosis,* 20:323-46).

A seminal study (Rath et al., *Arteriosclerosis,* 1989, 9:579-592) shows that Lp(a) accumulates in the arterial wall, partly in the form of lipoprotein like particles, therefore contributing to plaque formation and coronary heart disease. Other researchers have verified the results (Metso, et al., 1990, *European Heart Journal,* 11 (Supplement E), 190-195). This observation has been strongly supported and over the years has expanded to include higher incidences of myocardial infarction, stroke, and retinal artery occlusion.

Lp(a) consists of a low-density lipoprotein (LDL)-like moiety and an unique glycoprotein, Apo lipoprotein A1 (Apo A1)), that is covalently attached to the apolipoproteinB-100 (ApoB-100) component of LDL by a single disulfide bond. Many studies have suggested a role for Lp(a) in the process of endothelial dysfunction. Indeed, Lp(a) has been shown to increase both the expression of adhesion molecules on endothelial cells (EC), as well as monocyte and leukocyte chemotactic activity in these cells.

Lp(a) is structurally similar to LDL both in protein and in lipid composition, but is distinguishable from LDL by the presence of the unique glycoprotein moiety called Apo lipoprotein A (apo(A). It has been determined that Lp(a) particles contain Apo (a) and Apo lipoprotein B-100 (apoB) in a 1:1 molar ratio (Albers, et al., 1996, *J Lipid Res,* 37:192-6). In the Lp(a) particle, Apo (a) is covalently linked to Apo (b) by a single disulfide bridge. The cysteine residues in each molecule that are involved in the disulfide linkage have been identified (Callow M J, et al., 1995, *J Biol Chem,* 270:23914-7).

Lp(a) is only present in humans, Old World Monkeys and the hedgehog (Lawn R M, et al., 1996, *Clin Genet,* 49:167-74). The level of Lp(a) is genetically determined, and when elevated, cannot be lowered by alterations in food intake or by most of the cholesterol lowering agents. (Kostner G M, et al., 1989, *Circulation,* 8:1313-9).

Diabetic patients have higher Lp(a) values than nondiabetic persons (Haffner S M, et al., 1992, 49:116-20). Lp(a) was shown to be associated inversely with risk of type II diabetes independent of other risk factors, including BMI, HbA1c, or triglycerides. (Samia Mora, et al., 2010, *Clinical Chemistry,* 56:8 1252-1260).

Not only can Lp(a) be deposited in the arterial wall, but one of the more enticing possibilities backed by experimental evidence is that Lp(a) interferes with the fibrinolysis of blood clots. The evidence for the latter idea comes from observations that Lp(a) is capable of competing with plasminogen for binding sites on fibrin. (Rahman M N, et al., 2002, *Biochemistry,* 41:1149-55). In so doing, Lp(a) conceivably could increase the survival time of a clot in a wound and contribute to the thickening of the affected artery. While attached to the extracellular matrix the clot remnants could attract macrophages, which are known to be a source of factors that signal arterial cells to grow and divide, in essence promoting the atherosclerotic process. Apart from these thoughts, Lp(a) might be considered a very effective donor of cholesterol to cells, perhaps exceeding LDL, and hence capable of hastening formation of foam cells at the lesion site.

Despite its recognition as a risk factor for vascular disease, the role of Lp(a) in atherogenesis remains poorly understood. It has been postulated that owing to its duality of structure, Lp(a) may provide a functional link between the processes of atherosclerosis and thrombosis. In this model, Lp(a) likely possesses both atherosclerotic (owing to its similarity to LDL) and prothrombotic properties (based on the homology between Apo (A) and plasminogen). Clearly, Apo (A) possesses unique properties that contribute to the process of atherogenesis that are independent of its similarity to plasminogen (Koschinsky, M L, et al., 2004, *Curr Opin Lipidol,* 15:167-74).

Lp(a) is associated with increased risk of cardiovascular diseases (CVD), including coronary heart disease (CHD) and atherosclerosis (Anuurad, E, et al., 2006, *Clin Lab Med.,* 26:751-772). Moreover, as with most genetic risk factors that initiate risk at birth, it is a stronger CVD risk factor in young patients (less than 60 years old), and in those with highly elevated levels of Lp(a), and in those with additional atherogenic risk factors, particularly elevated LDL cholesterol (Tsimikas, S., et al., 2005, *N Engl J Med.,* 353:46-57). Lp(a) is present in the arterial wall at the sites of atherosclerotic lesions and that it accumulates at these sites to an extent that is proportional to plasma Lp(a) levels. Lp(a) is preferentially retained in this milieu, likely by virtue of its ability to bind to a number of arterial wall components including fibrinogen/fibrin, fibronectin, and glycosaminoglycans (Koschinsky M L, et al., 2004, *Curr Opin Lipidol,* 15:167-74). The localization of Lp(a) within the arterial wall suggests a direct causative role for Lp(a) in the initiation and/or progression of atherosclerosis.

Lp(a) has been implicated in the regulation of plasminogen activator inhibitor-1 expression in endothelial cells and shown to inhibit endothelial cell surface fibrinolysis to attenuate plasminogen binding to platelets and to bind to plaque matrix components. Autopsy studies in humans have documented the presence of Lp(a) in aortic and coronary atherosclerotic plaques and an apparent localization with fibrinogen (Hoefler G, 1998, *Arteriosclerosis*, 8(4): 398-401).

Lp(a) levels are frequently elevated in patients receiving chronic hemodialysis treatment of end-stage renal disease (Quashing T, et al., 2001, *Am J Kid Dis*, 38, suppl 1, 514-9). It has been suggested that kidney have an important role in Lp(a) metabolism. In renal failure, there is a decrease in Lp(a) catabolism or increase in Lp(a) production by liver. In hemodialysis patients, Lp(a) has been shown to have the characteristics of an acute phase reactant (Maeda S, et al., 1989, *Atherosclerosis*, 78:145-50). Patients with Peripheral artery disease (PAD) showed significantly higher median serum concentrations of Lp(a) than controls (Dieplinger, et al. 2007, *Clinical Chemistry*, 53:7 1298-1305).

Lp(a) concentration and Apo B to ApoAI ratio in 55 South Asian subjects with ischemic stroke and 85 controls. The analysis of the data showed that both parameters were associated with ischemic stroke (Sharobeem, K. M, et al., 2007, *Int. J. Clin. Pract*, 61(11): 1824-1828).

Lp(a) levels in 100 patients with acute ischemic stroke and 100 healthy subjects were compared and noted that even a slight elevation in Lp(a) plasma concentration was strongly and independently associated with ischemic stroke in men, but not in women. (Rigal, M, et al., 2007, *J. Neurol. Sci.*, 252(1):39-44).

The role of Lp(a) in silent cerebral infarction (SCI) was investigated in patients with chronic renal failure who were maintained on hemodialysis. Lp(a) was found to be significantly associated with the presence of SCI (Fukunaga, N, et al., 2008, *Metabolism*, 57(10):1323-1327).

In a study of homocysteine and Lp(a) in ischemic stroke it was seen plasma Lp(a) concentration patients with ischemic stroke and controls and found that these two parameters are independently associated with ischemic stroke with a significant positive correlation between them (Dhamija, R. K, et al., 2009, *J. Neurol. Sci.*, 281(1-2):64-68). Increased Lp(a) levels in acute phases, such as after surgery, inflammation, pregnancy, myocardial infarction, psoriasis, gout and others have been reported. Lp(a) has been shown to be a potent chemo attractant for human peripheral monocytes. (Syrovets, et al., 1997, *Blood*, 90:2027-2036).

Hypothyroid patients have increased, while hyperthyroid patients have decreased plasma Lp(a) levels in comparison to euthyroid controls. Human growth hormone drastically increases Lp(a) by up to 120% (Laron Z, et al., 1997, *J Pediatr Endocr Met*, 10:143-149).

Patients with many forms of kidney disease exhibit striking elevations of plasma Lp(a) levels. In patients with end-stage renal disease (ESRD), Lp(a) and the Apo(a) phenotype are predictors for both the degree of preclinical atherosclerosis and atherosclerotic events. In ESRD and nephrotic syndrome elevations of Lp(a) are not only due to overproduction of Lp(a) by the liver but also to diminished excretion of Apo (a) fragments into the urine (Kostner and Kostner, 2002, *Curr Opin Lipidol*, 13:391-396).

There is a highly significant association between Lp (a) and the presence and progression of breast cancer, and the serum Lp (a) determination may provide an aid in patients with breast cancer for both diagnostic purposes and the follow-up of the disease (Kökôglu E, et al., 1994, *Cancer Biochem Biophys.*, 1994, 4(2):133-6.)

Recent studies have suggested a link between Lp(a) and oxidized phospholipids. Specifically, it has been shown that in human plasma, oxidized phospholipids are preferentially associated with Lp(a) compared to free LDL (Tsimikas S, et al., 2003, *J Am Coll Cardiol*, 41:360-70).

Most patients with the nephrotic syndrome have Lp(a) concentrations that are substantially elevated compared with controls of the same Apo(a) isoform. Because Lp(a) concentrations are substantially reduced when remission of the nephrotic syndrome is induced, it is likely that the nephrotic syndrome results directly in elevation of Lp(a) by an as yet unknown mechanism. The high levels of Lp(a) in the nephrotic syndrome could cause glomerular injury as well as increase the risk for atherosclerosis and thrombotic events associated with this disorder (Wanner. L, et al., 1993, *Ann Intern Med*, 119:263-269).

Lp(a) is commonly reported to be significantly increased in cancer patients as compared to healthy controls, irrespective of source and degree of malignancy of the tumor. Patients suffering from cancer of different locations and origin exhibit up to two fold elevated plasma Lp(a) concentrations. Patients with acute myelotic leukemia have very high Lp(a) levels (Wright, et al., 1989, *Int J Cancer*, 43:241-244).

At present, the one. albeit costly and invasive method of proven value is LDL apheresis (Armstrong V W, et al., 1989, *Eur. J. Clin. Invest.*, 19:235-40), resembling dialysis, to eliminate the cholesterol-containing particle low-density lipoprotein (LDL) from the bloodstream. Which should be reserved for individuals with extreme elevations of Lp(a). The procedure takes 2-4 hours and must be repeated every several weeks to keep the LDL levels from accumulation and causing cardiovascular disease. It is an expensive procedure, limiting its use to severe cases of hyperlipidemia. Unfortunately, there is no drug therapy that is currently available to specifically lower Lp(a) levels without affecting other lipoproteins.

APO A-1 and APO B

Although LDL cholesterol (LDL-C) is thought to be associated with an increased risk of coronary heart disease, other lipoproteins and their constituents, Apo lipoproteins, may play an important role in atherosclerosis.

Elevated levels of Apo lipoprotein (Apo) B, a constituent of atherogenic lipoproteins, and reduced levels of Apo A-I, a component of anti-atherogenic HDL, are associated with increased cardiac events. Apo B, Apo A-1 and the Apo B/Apo A-I ratio have been reported as better predictors of cardiovascular events than LDL-C and they even retain their predictive power in patients receiving lipid-modifying therapy. Measurement of these Apo lipoproteins could improve cardiovascular risk prediction. (Jungner, et al., *Journal of Internal Medicine*, 2004, 255:188-205).

Levels of Apo A-I are strongly correlated with those of HDL-C, and expression of Apo A-I may be largely responsible for determining the plasma level of HDL (XV International Symposium on Atherosclerosis, Jun. 14-18, 2009, Boston, Mass., USA). Apo A-I also acts as a cofactor for lecithin cholesterol acyl transferase (LCAT) [Phillips M C, et. al (1998; Atherosclerosis 137(Suppl): S 13-7), which is important in removing excess cholesterol from tissues and incorporating it into HDL for reverse transport to the liver. Furthermore, Apo A-1 is the ligand for the ATP-binding cassette (ABC) protein, ABCA1, and hence is involved in the docking procedure by which excess cholesterol in peripheral cells is externalized to HDL. (Oram J F, et al., 2000, *J Biol Chem*, 275 34508-11), for further reverse cholesterol transport either directly or indirectly via LDL back to the liver (Tailleux A, et al., 2002, *Atherosclerosis*, 164: 1-13).

The Prospective Epidemiological Study of Myocardial Infarction (PRIME) study examined the association between the incidence of CHD and several HDL related parameters, including HDL-C itself, Apo A-I, HDL A-I, and HDL A-I:A-

II (Luc G, et al., 2002, *Arterioscler Thromb Vasc Biol*, 22:1155-61). All four parameters were related to CHD risk; however, Apo A-I was the strongest predictor. In addition, the use of Apo A-1 for predicting CAD has been confirmed by other studies (Garfagnini A, et al., 1995, *Eur Heart J*, 16:465-70).

Apo Lipoprotein B

Apo lipoprotein B exists in two forms, Apo B-48 and Apo B-100. Apo B-48 is synthesized in the intestine, where it is complexes with dietary TG and free cholesterol absorbed from the gut lumen to form chylomicron particles. These are metabolized in the circulation and in the liver. Apo B-100 is synthesized in the liver and is present in LDL, IDL and VLDL particles. Only one Apo B molecule is present in each of these lipoprotein particles (Elovson J, et al., 1998, *J Lipid Res*, 29:1461-73). The total Apo B value indicates the total number of potentially atherogenic lipoproteins (Walldius G, et al., 2001, *Lancet*, 2001, 358:2026-33). Apo B is essential for the binding of LDL particles to the LDL receptor, allowing cells to internalize LDL and thus absorb cholesterol. An excess of Apo B-containing particles is a main trigger in the atherogenic process.

The concentration of plasma Apo B particles is highly correlated with the level of non-HDL cholesterol (non-HDL-C), defined as TC minus HDL-C (Ballantyne C M, et al., 2001, *Am J Cardiol*, 88:265-9). As HDL is known to be protective against cardiovascular risk, non-HDL-C reflects the fraction of blood cholesterol that is not contained in atheroprotective lipoproteins. Therefore, non-HDL-C has been recognized by the National Cholesterol Education Program Adult Treatment Panel III (NCEP ATP III) guidelines as a target for lipid-lowering therapy (Circulation, 2002, 106: 3143-421). Non-HDL-C has been found to predict nonfatal myocardial infarction (MI) and angina pectoris. However, Apo B has been found to be a better predictor of risk than non-HDL-C (Sniderman A D, et al., 2003, *Lancet*, 361:777-80). Using Apo B and Apo A-I, expressed as the Apo B/Apo A-1 ratio, seems to be a very effective way of characterizing cardiovascular risk in any patient irrespective of their lipoprotein abnormality.

Patients with diabetes or the metabolic syndrome can have normal LDL-C levels but possess aspects of the atherogenic lipid profile (Sniderman A D, et al., 1001, *Ann Intern Med*, 135:447-59), and these individuals often have a high ratio of Apo B/Apo A-I, which is a strong indicator of cardiovascular risk (Walldius G, et al, 2002, *Diabetes*, 51(Suppl.):A20).

Parathyroid Hormone (PTH)

Chronic Kidney Diseases (CKD) is a significant and growing health problem characterized by the progressive loss of kidney function and the many ensuing complications. As a result of the loss of excretory, regulatory, and endocrine function of the kidney, patients with CKD experience multiple medical complications such as electrolyte abnormalities, anemia, secondary hyperparathyroidism (SHPT), and renal osteodystrophy. In addition, these patients commonly have other serious medical complications such as soft tissue and vascular calcification, cardiovascular disease, infection, and malnutrition. (Horl W H, 2004, Nephrol Dial Transplant, 19 suppl 5, V2-V8.) As a result, patients with CKD are at risk for increased morbidity and mortality. Cardiovascular mortality is 15 times higher in patients on dialysis than in the general population. (Sarnak, M J, 2000, *Am J Kidney Dis*, 35(suppl 1):S117-S131).

CKD is defined as either kidney damage or glomerular filtration rate (GFR)<60 mL/min/1.73 m2) for ≥3 months; kidney damage is defined as pathologic abnormalities or markers of damage, including abnormalities in blood or urine tests or imaging studies (National guidelines, 2002, *Am J Kidney Dis*, 39, (suppl 1): S1-S266).

SHPT (secondary hypothyroidism) occurs most commonly in CKD as a result of altered mineral metabolism characterized by hyperphosphatemia, vitamin D deficiency, and/or hypocalcaemia. These mineral abnormalities start to become evident in the early stages of CKD once the glomerular filtration rate (GFR) is below 60 mL/min/1.73 m2 (stage 3 CKD) and continue to progress as renal function declines. SHPT may also result from non-renal causes of vitamin D deficiency such as low sun exposure, decreased dietary intake, malabsorption, and advanced age (Tomasello, S, 2008, *Diabetes Spectrum*, 21(1):19). These patients with SHPT may experience numbness, tingling, cramps, seizures, from the resultant hypocalcaemia and hypophosphatemia, which usually results in PTH production, to restore homeostasis of these minerals.

Parathyroid hormone (PTH) is a polypeptide containing 84 amino acids that is secreted by the parathyroid glands after cleavage from pre-pro parathyroid hormone (115 amino acids) to pro parathyroid hormone (90 amino acids) to the mature hormone. The major target end organs for parathyroid hormone (PTH) action are the kidneys, skeletal system, and intestine.

The primary response to parathyroid hormone (PTH) by the kidney is to increase renal calcium resorption and phosphate excretion. In the kidney, parathyroid hormone (PTH) blocks reabsorption of phosphate in the proximal tubule while promoting calcium reabsorption.

An important function of parathyroid hormone (PTH) is conversion of 25-hydroxyvitamin D to its most active metabolite, 1,25-dihydroxyvitamin D3, by activation of the enzyme 1-hydroxylase in the proximal tubules of the kidney (Haussler, M R., 1998, *J Bone Min Res*, 13:325-349).

Inhibition of parathyroid hormone (PTH) release occurs primarily by direct effect of calcium at the level of the parathyroid gland. Although not well elucidated, 1,25-(OH) dihydroxy Vitamin D3 appears to exert a mild inhibitory effect on the parathyroid gland as well. Declining kidney function leads to a deficiency of activated vitamin D and an increase in phosphorus excretion. Both of these changes stimulate an increase in PTH synthesis and secretion.

Vitamin D3 plays a vital role in regulating PTH synthesis and release. By stimulating the parathyroid VDR, it down regulates the production of PTH. Vitamin D3 also decreases PTH indirectly by stimulating VDRs in the gut, thereby increasing calcium absorption and serum calcium (Brown A J, 1999, *Am J Physiol*, 277:157-175; Tomasello, S, 2008, *Diabetes Spectrum*, 21:1:19).

As kidney function declines, there is a decrease of renal 1α-hydroxylase activity that is responsible for the final hydroxylation reaction in calcitriol synthesis. In worsening CKD, the kidney becomes less able to perform 1α-hydroxylation and, consequently, active vitamin D3 levels become deficient and increases PTH concentrations (Malluche, H H, 2002, *Kidney Int*, 62:367-374).

The severity of secondary hyperparathyroidism in chronic renal insufficiency is GFR-dependent, race dependent, and associated with cardiovascular disease (De Boer I H, et al., 2002, *J Am Soc Nephrol*, 13:2762-2769). Parathyroid hormone (PTH) concentrations begin to increase in patients in stage 2 and become elevated in many patients in stage 3, as well as in most patients in stages 4 and 5 who are not receiving treatment. Histologic changes are observed in bone biopsies even among stage 3 and 4 patients with modest PTH elevation. In patients on dialysis, the SHPT and bone disease worsen and become more difficult to treat as the duration of dialysis increases.

Elevated Phosphate level is common in patients with CKD due to their impaired ability to excrete phosphorus renally. Phosphorus retention and the resultant increase of serum phosphorus concentrations directly suppress the production of calcitriol. Furthermore, the shrinkage in renal mass results in reduced activation of vitamin D to calcitriol. Calcium absorption from the gastrointestinal (GI) tract is reduced, resulting in hypocalcaemia. These derangements are interrelated and can either individually or collectively stimulate the synthesis and/or secretion of PTH by the parathyroid gland. The continuous increased production of PTH subsequently leads to hyperplasia of the parathyroid gland. Eventually, the gland may become autonomous in secreting PTH and less likely to respond to therapy.

Phosphorus Metabolism

As the glomerular filtration rate (GFR) declines to <60 ml/min/1.73 m2, phosphorus excretion becomes altered in the nephron. Although half of the nephrons are not working to excrete phosphorus, the remaining nephrons compensate by hyper-excreting the daily phosphorus load to maintain normal serum phosphorus concentrations. Compensation can generally continue until the GFR declines to <25-40 ml/min/ 1.73 m2. With progressive CKD, when the remaining nephrons can no longer sufficiently excrete the phosphorus load, and hyperphosphatemia results.

Calcium, a divalent cation, and phosphorus, a monovalent anion, have a high binding affinity for each another. In the serum, as the concentration of one or both ions increases, there is an increased risk for an ionic bonds to form, creating an insoluble complex. This process may lead to extra skeletal calcification and potentially calciphylaxis or cardiac disease (Ketteler, et al., *Pediatr Nephrol*, 2011, 26:7-18). Additionally, the precipitation may decrease serum calcium concentrations, further stimulating PTH secretion. In fact, PTH production and secretion may be stimulated by hypocalcaemia, hyperphosphatemia, and vitamin D deficiency (Friedman E A, 2005, *Kidney Int*, 65 (Suppl.): S1-S7).

Because PTH is chiefly responsible for preventing hypocalcaemia, it stimulates osteoclasts to lyse bone, releasing calcium into the serum. Under normal conditions, there is homeostasis involving osteoclast activity and osteoblast synthetic activity. SHPT produces an imbalance of these activities leading to enhanced bone breakdown that eventuates in renal osteodystrophy (Tomasello, S, 2008, *Diabetes Spectrum*, 21:1:19).

Calcification

In addition to bone mineral defects and disease, alterations in calcium, phosphorus, vitamin D, and PTH cause other deleterious consequences in patients with CKD. Extra skeletal calcification (primarily cardiovascular calcification) has been documented in patients with CKD (Goodman W G, 2000, *N Engl J Med*, 342:1478-1483) and is directly correlated to an increase in cardiovascular morbidity and mortality. Patients with CKD, especially with end-stage renal disease (ESRD), have an increased risk of cardiovascular morbidity and mortality Research has shown that the primary cause of death in patients with End stage renal disease (ESRD) is cardiovascular disease (U.S. Renal Data System: USRDS 2006 Annual Data Report NIDDK 2006). A study of patients on hemodialysis found that even when stratified for variables such as sex, race, and presence of diabetes, dialysis patients still had a cardiovascular mortality rate nearly 30 times greater than the general population (Block, G A, 2004, *J Am Soc Nephrol*, 15:2208-2218).

The balance of calcium, phosphorus, vitamin D, and Intact PTH (I-PTH) is complex and interrelated. Patients must adhere to dietary restrictions, dialysis therapies, and complicated medication regimens. These factors create barriers to achieving and maintaining control of SHPT. A study of nearly 200 chronic hemodialysis outpatients revealed that <10% of patients could be simultaneously maintained within the target ranges of the above parameters. (Tomasello, S, 2004, *Dialysis Transplant*, 33:236-242).

eGFR

Glomerular filtration rate (GFR which is also referred to as "e-GFR" or "eGFR") is considered by medical professionals to be the best measure of kidney function. Knowing someone's GFR helps the medical professional figure out the stage of kidney disease. Doctors will use this information to plan their patient's treatment.

The proportional variation in the GFR is larger in populations with the disease (by a factor of approximately 10, from 6 to 60 ml per minute per 1.73 mls/min/1.73 $m^2$) than in populations without the disease (by a factor of approximately 3, from 60 to 180 ml per minute per 1.73 mls/min/1.73 $m^2$). As a result, larger proportion of the variation in serum creatinine levels among patients with the disease is due to a variation in the GFR, not to a variation in the other determinants as compared with healthy people.

The GFR assesses the excretory function of the kidneys and is considered the gold standard used to evaluate renal function. The National Kidney Foundation's guidelines for chronic kidney disease, a GFR exceeding 90 mL/min/1.73 $m^2$ is considered normal; GFR of 60 to 89 is mildly decreased; a GFR of 30 to 59 is moderately decreased and may signify "renal insufficiency"; a GFR of 15 to 29 mL/min/1.73 m2 is considered severely decreased; and a GFR of less than 15 is considered kidney failure. Decreased kidney function is associated with many complications, such as hypertension, anemia, malnutrition, bone disease, and a decreased quality of life (National Kidney Foundation, 2000, *Am J Kidney Dis*, 2:39, (suppl 1): S1-266).

Prostate Specific Antigen (PSA)

Prostate cancer is the most commonly diagnosed cancer in men and a leading cause of cancer death in the United States and Europe (Boyle P, et al., 2005, *Ann Oncol*, 16:481-488).

Prostate-specific antigen (PSA) is a protein produced by the cells of the prostate gland. The PSA test measures the level of PSA in the blood. It is normal for men to have low levels of PSA in their blood; however, prostate cancer or benign (not cancerous) conditions can increase PSA levels. As men age, both benign prostate conditions and prostate cancer become more frequent. The most common benign prostate conditions are prostatitis (inflammation of the prostate) and benign prostatic hyperplasia (BPH) (enlargement of the prostate). There is no evidence that prostatitis or BPH cause cancer, but it is possible for a man to have one or both of these conditions and to develop prostate cancer as well. A PSA level of 4.0 ng/mL is considered an appropriate cutoff for selecting men for prostate biopsy (Catalona W J, 1994, J Urol; 152: 2037-42). A recent report from the Prostate Cancer Prevention Trial showed that prostate cancer occurs in men with low PSA levels (Thompson I M, et al., 2004, *N Engl J Med*, 350:2239-46), suggesting that there is no "normal" PSA but rather a continuum of risk of prostate cancer based on an individual's PSA level (Thompson I M, 2005, *JAMA*, 294:66-70).

Vitamin D receptor expression is inversely associated with prostate cancer progression; VDR levels in tumor tissue may influence prostate cancer prognosis (Nutrition and Health: Vitamin D Edited by: M. F. Holick, 2010, PP 797; Springer Science-Business Media, LLC).

Many epidemiological studies, indicate that vitamin D deficiency increases the risk of prostate cancer and that higher levels of vitamin D are associated with better prognosis and improved outcomes (Young, et al., 2011, *Advances in Preventive Medicine*: Volume, Article ID 281863). The outcome of clinical trials using vitamin D, calcitriol or various vitamin D analogs in men with prostate cancer have thus far been disappointing.

Liver Enzymes (AST, ALP, ALP and Bilirubin)

Abnormalities in liver function tests are elevated levels of biochemical tests, including aspartate aminotransferase (AST) or serum glutamic-oxaloacetic transaminase [SGOT]), alanine aminotransferase (ALT) or serum glutamate pyruvate transaminase [SGPT]), alkaline phosphatase, bilirubin, and albumin Cellular injury in the liver causes release of AST and ALT. ALT is a more specific indication of liver disease, whereas AST elevations may be secondary to damage of other organs (heart, kidney, brain, intestine, placenta).

The ALT is found in the cytosol of liver, whereas two AST isoenzymes are located in the cytosol and mitochondria, respectively. Both enzymes are released into the blood in increasing amounts when the liver cell membrane is damaged. Necrosis of liver cells is not required for the release of the aminotransferase. In fact, there is poor correlation between the degree of liver-cell damage and the level of the aminotransferase. The ALT is found in low concentrations in tissues other than liver, so it is frequently considered specific for hepatocellular injury. However, this specificity is not absolute because serum ALT elevations can occur in non-hepatic conditions such as myopathic diseases. Liver cell necrosis is indicated by highly elevated ALT levels (Tung, B Y, 1999, *Clin Liver Dis*, 3:585-601).

The AST also is abundantly expressed in several non hepatic tissues including heart, skeletal muscle, and blood. Nonetheless, both the ratio and absolute elevation of the AST and ALT can provide important information regarding the extent and etiology of liver disease.

While no single biochemical liver function test is sufficiently specific to allow a definite diagnosis in patients with liver disease, we have been impressed by the consistency with which the serum glutamic oxaloacetic transaminase (SGOT) activity exceeds the serum glutamic pyruvic transaminase (SGPT) activity in patients with alcoholic liver disease.

Nonalcoholic fatty liver disease (NAFLD) refers to a wide spectrum of liver disease ranging from simple fatty liver (steatosis), to nonalcoholic steatoheppatitis (NASH), to cirrhosis (irreversible, advanced scarring of the liver). All of the stages of NAFLD have in common the accumulation of fat (fatty infiltration) in the liver cells (hepatocytes). In NASH, the fat accumulation is associated with varying degrees of inflammation (hepatitis) and scarring (fibrosis) of the liver.

It was shown (Cohen et al., 1979, *Digestive Diseases and Sciences*, 24(11) that SGOT/SGPT ratio is significantly elevated in patients with alcoholic hepatitis and cirrhosis (2.85+−0.2) compared with patients with post necrotic cirrhosis (1.74+ or −0.2), chronic hepatitis (1.3+ or −0.17), obstructive jaundice (0.81+ or −0.06) and viral hepatitis (0.74+ or −0.07). An SGOT/SGPT ratio greater than 2 is highly suggestive of alcoholic hepatitis and cirrhosis. It occurs in 70% of these patients compared with 26% of patients with post necrotic cirrhosis, 8% with chronic hepatitis, 4% with viral hepatitis and none with obstructive jaundice. (Sorbi, et al., 1999, *Am J Gastroenterol*, 94:1018-1022).

The AST to ALT ratio has been reported to be a useful parameter supporting the diagnosis of alcoholic hepatitis (Finlayson, et al., 1993, *Bailliere's Clin Gastroenterol*, 7:627-640; 40: Harrison, D J, et al., *Bailliere's Clin Gastroenterol*, 1993, 7:641-62).

An AST level more than twice the ALT level has been reported in as many as 83% of patients hospitalized for alcoholic hepatitis (Pinto, H C, et al., 1996, *Dig Dis Sci*, 1996, 41:172-9; Bird G L A, et al., 1993, *Bailliere's Clin Gastroenterol*, 1997, 663-82).

The AST to ALT ratio appears to be a useful index for distinguishing nonalcoholic steatoheppatitis (NASH) from alcoholic liver disease. Subset analysis of patients with NASH revealed mean AST to ALT ratios of 0.7, 0.9, and 1.4 for subjects with no fibrosis, mild fibrosis, or cirrhosis, respectively (Sorbii. D, et. al., 1999, *The American Journal of Gastroenterology*, 94(4)).

Alkaline Phosphatase

Alkaline phosphatase (ALP) is associated with cellular membranes, and elevated levels may be caused by injury to the liver, bone, kidneys, intestines, placenta, or leukocytes. In the liver, the enzyme is located in the bile canaliculi. Biliary obstruction induces increased synthesis of alkaline phosphatase and spillage into the circulation. Elevations in serum ALP levels originate predominantly from two sources, liver and bone. It is also present in kidneys, small bowel and placenta. Levels vary with age. Rapidly growing adolescents can have serum ALP levels that are twice those of healthy adults as a result of the leakage of bone. Also, serum ALP levels normally increase gradually between the ages of 40 and 65 years, particularly in women. Women in the third trimester of pregnancy have elevated serum level ALP because of an influx of placental ALP into their blood. In persons with blood type O or B, serum ALP levels may increase after the ingestion of a fatty meal; because of an influx of intestinal ALP there are also reports of a benign familial elevation in serum ALP levels because of increased levels of intestinal ALP (Wolf P L, 1978, *Arch. Pathol. Lab. Med*, 102:497-501).

Bilirubin

The human body produces about 4 mg per kg of bilirubin per day from the metabolism of heme. Approximately 80 percent of the heme moiety comes from catabolism of red blood cells, with the remaining 20 percent resulting from ineffective erythropoiesis and breakdown of muscle myoglobin and cytochromes. Bilirubin is transported from the plasma to the liver for conjugation and excretion.

Hyperbilirubinemia may signify hepatobiliary disease or hemolysis. Mild degrees of indirect hyperbilirubinemia may be found in as many as 10% of asymptomatic patients with Gilbert's syndrome (Lidofsky, S D, Jaundice, In: Feldman M, et al., Sleisenger and Fordtran's Gastrointestinal and Liver Disease, 8th ed. Philadelphia, Pa.: Saunders Elsevier, 2006).

Prior to age 30, hepatitis causes 75% of hyperbilirubinemia. After age 60, extra hepatic obstruction causes 50% of hyperbilirubinemia (e.g., gallstones or pancreatic cancer).

Intra-hepatic disorders can lead to unconjugated or conjugated hyperbilirubinemia. The conjugated (direct) bilirubin level is often elevated by alcohol, infectious hepatitis, drug reactions, and autoimmune disorders. Post hepatic disorders also can cause conjugated hyperbilirubinemia. Gallstone formation is the most common and benign post hepatic process that causes jaundice; however, the differential diagnosis also includes serious conditions such as biliary tract infection, pancreatitis, and malignancies (S. P. Roche, et al., 2004, *Am Fam Physician*, 2004, 69:299-304). Biliary obstruction is a condition where blood levels of conjugated bilirubin increase.

Symptoms of hemolytic anemia are similar to other forms of anemia (fatigue and shortness of breath), but in addition, the breakdown of red cells leads to jaundice and increases the risk of particular long-term complications, such as gallstones and pulmonary hypertension.

Hemolytic jaundice can lead increased production of bilirubin. In this case bilirubin is conjugated and excreted normally, but the conjugation mechanism is overwhelmed, and an abnormally large amount of unconjugated bilirubin is found in the blood.

Gilbert syndrome is a common, benign, hereditary disorder that affects approximately 5 percent of the U.S. population. (Schreiber R. A., et al., 2001, *Pediatr Rev,* 22:219-26). Typically, the disease results in a mild decrease in the activity of the enzyme glucuronosyltransferase, causing an increase in the indirect fraction of serum bilirubin. Gilbert syndrome is typically an incidental finding on routine liver function tests, when the bilirubin level is slightly increased and all other liver function values are within normal limits. Jaundice and further elevation of the bilirubin level may occur during periods of stress, fasting, or illness.

Crigler-Najjar Syndrome or CNS is a rare disorder affecting the metabolism of bilirubin, a chemical formed from the breakdown of blood. The disorder results in an inherited form of non-hemolytic jaundice, which results in high levels of unconjugated bilirubin and often leads to brain damage in infants. This syndrome is divided into type I and type II, with the latter sometimes referred to as Arias syndrome. These two types, along with Gilbert's syndrome, Dubin-Johnson syndrome, and Rotor syndrome, make up the five known hereditary defects in bilirubin metabolism. Unlike Gilbert's syndrome, only a few hundred cases of CNS are known (Jansen P L, et al., 1999, *European Journal of Pediatrics,* 158, Suppl 2, S89-S94, 0154).

Dubin-Johnson syndrome is an autosomal recessive disorder that causes an increase of conjugated bilirubin in the serum without elevation of liver enzymes (ALT, AST). This condition is associated with a defect in the ability of hepatocytes to secrete conjugated bilirubin into the bile, and is similar to Rotor syndrome. It is usually asymptomatic but may be diagnosed in early infancy based on laboratory tests.

(Rotor syndrome, also called Rotor type hyperbilirubinemia, is a rare, relatively benign autosomal recessive bilirubin disorder of unknown origin. It is a distinct disorder; yet similar to Dubin-Johnson syndrome both diseases cause an increase in conjugated bilirubin (Wolkoff, A W, et al., 1976, *The American Journal of Medicine,* 60(2):173-179).

Thyroid Diseases

According to the World Health Organization (WHO), thyroid diseases have the second-highest prevalence among all endocrine disorders, right behind diabetes mellitus. Over 665 million people suffer from endemic goiter or other thyroid diseases worldwide; 1.5 billion people are at risk for developing an iodine-deficient condition. Statistical data show that the annual increment in the number of thyroid disease cases is 5%. Hypothyroidism is a common endocrine disorder resulting from deficiency of thyroid hormone. Worldwide, iodine deficiency remains the foremost cause of hypothyroidism. In the United States and other areas of adequate iodine intake, autoimmune thyroid disease (Hashimoto disease) is the most common cause of hypothyroidism; worldwide, iodine deficiency remains the foremost cause. Among all methods available to treat diseases of the thyroid gland (thyroid), a preference is given to hormone replacement therapy (HRT), treatment with antithyroid drugs, surgical intervention (thyroidectomy), and radioactive iodine therapy. An estimated 20 million Americans have some form of thyroid disease according to the American Thyroid association. One in eight women will develop a thyroid disorder during her lifetime. Levothyroxine, a synthetic form of thyroid hormone, is the 4th highest selling drug in the U.S. 13 of the top 50 selling drugs are either directly or indirectly related to hypothyroidism.

All these treatment standards characteristically have a considerable number of contraindications and shortcomings. In particular, hormone replacement therapy requires lifelong administration of thyroid hormone preparations and, as a result, the patient's own thyroid eventually stops functioning at all thus making the patient a "lifelong client" of pharmaceutical companies. Besides, administration of thyroid hormone preparations has a number of contraindications, and multiple adverse effects, including tachycardia, cardiac arrhythmia, allergic reactions, excitation, insomnia, etc., accompany this treatment.

The aim of antithyroid therapy practiced today is partial or complete suppression of the patient's own thyroid function after which the patient is switched to hormone replacement therapy. Adverse effects of thyrostatic therapy include inhibition of hematopoiesis, nausea, vomiting, liver function impairment, allergic reactions, etc.

Surgical intervention is often accompanied by complications responsible for a near-10% disability rate. Other significant disadvantages of thyroid ablation (or removal of a part of the thyroid) include lifelong administration of hormones and a high risk of damage to the parathyroid glands during surgery. Medicine today is unable to offer patients with thyroid diseases any alternatives, and prefers to ignore the disadvantages of current treatment regimens and standards.

Thyroid Regulation

The thyroid is a butterfly shaped organ located just below the Adam's apple in the neck. Made up of small sacs, this gland is filled with an iodine-rich protein called thyroglobulin along with the thyroid hormones thyroxine (T4) and small amounts of triiodothyronine (T3).

The primary function of these two hormones is to regulate metabolism by controlling the rate at which the body converts oxygen and calories to energy. In fact, the metabolic rate of every cell in the body is regulated by thyroid hormones, primarily T3. (Videla L A, Fernandez V, Tapia G, Varela P. Thyroid hormone calorigenesis and mitochondrial redox signaling: up regulation of gene expression. Front Biosci. 2007 Jan. 1; 12:1220-8).

In healthy individuals the gland is imperceptible to the touch. A visibly enlarged thyroid gland is referred to as a goiter. Historically, goiter was most frequently caused by a lack of dietary iodine. However, in countries where salt is iodized, goiter of iodine deficiency is rare.

The production of T4 and T3 in the thyroid gland is regulated by the hypothalamus and pituitary gland. To ensure stable levels of thyroid hormones, the hypothalamus monitors circulating thyroid hormone levels and responds to low levels by releasing thyrotropin-releasing hormone (TRH). This TRH then stimulates the pituitary to release thyroid-stimulating hormone (TSH). (Segerson T P, et. al, Science. 1987 Oct. 2; 238(4823): 78-80; Dyess E M, et. al, Endocrinology. 1988 November; 123(5): 2291-7).

When thyroid hormone levels increase, production of TSH decreases, which in turn slows the release of new hormone from the thyroid gland. Cold temperatures can also increase TRH levels. This is thought to be an intrinsic mechanism that helps keep us warm in cold weather.

Elevated levels of cortisol, as seen during stress and in conditions such as Cushing's syndrome, lowers TRH, TSH and thyroid hormone levels as well. (Roelfsema F, et. al, Eur J Endocrinol. 2009 November; 161(5): 695-703.

The thyroid gland needs iodine and the amino acid L-tyrosine to make T4 and T3. A diet deficient in iodine can limit how much T4 the thyroid gland can produce and lead to hypothyroidism. (Angermayr L, et. al, Cochrane Database Syst Rev. 2004; (2): CD003819).

T3 is the biologically active form of thyroid hormone. The majority of T3 is produced in the peripheral tissues by conversion of T4 to T3 by a selenium-dependent enzyme.

Various factors including nutrient deficiencies, drugs, and chemical toxicity may interfere with conversion of T4 to T3. (Kelly G S. Altern Med Rev. 2000 August; 5(4): 306-33).

Another related enzyme converts T4 to an inactive form of T3 called reverse T3 (rT3). Reverse T3 does not have thyroid hormone activity; instead it blocks the thyroid hormone receptors in the cell hindering action of regular T3. (Köhrle J. Acta Med Austriaca. 1996; 23(1-2): 17-30).

Ninety-nine percent of circulating thyroid hormones are bound to carrier proteins, rendering them metabolically inactive. The remaining "free" thyroid hormone, the majority of which is T3, binds to and activates thyroid hormone receptors, exerting biological activity. (Nussey S, et. al, Endocrinology: An Integrated Approach. Oxford: BIOS Scientific Publishers, 2001). Very small changes in the amount of carrier proteins will affect the percentage of unbound hormones. Oral contraceptives, pregnancy, and conventional female hormone replacement therapy may increase thyroid carrier protein levels and, thereby, lower the amount of free thyroid hormone available. (Arafah B M., Increased need for thyroxine in women with hypothyroidism during estrogen therapy. N Engl J. Med. 2001 Jun. 7; 344(23): 1743-9).

The thyroid gland is the biggest gland in the neck. The sole function of the thyroid is to make thyroid hormone. Thyroid hormones regulate our body's metabolism and influence virtually every organ system in the body. They tell organs how fast or slow they should work. Thyroid hormones also regulate the body's consumption of oxygen and production of heat. Thyroid problems, such as an overactive or under active thyroid, can severely affect metabolism (Franklyn, et al., 2005, *Journal of Endocrinology*, 187:1-15).

Hyperthyroidism

Too much thyroid hormone from an overactive thyroid gland is called hyperthyroidism, because it speeds up the body's metabolism. This hormone imbalance occurs in about 1 percent of all women, who get hyperthyroidism more often than men. One of the most common forms of hyperthyroidism is known as Graves' disease. Because the thyroid gland is producing too much hormone in hyperthyroidism, the body develops an increased metabolic state, with many body systems developing abnormal function (Wondisford, *Clinical Management of Thyroid Diseases*, ISBN: 978-1-4160-4745-2, Copyright © 2009 by Saunders. Philadelphia).

Hypothyroidism

Too little thyroid hormone from an under active thyroid gland is called hypothyroidism. In hypothyroidism, the body's metabolism is slowed. Several causes for this condition exist, most of which affect the thyroid gland directly, impairing its ability to make enough hormone. More rarely, there may be a pituitary gland tumor, which blocks the pituitary from producing TSH. As a consequence, the thyroid fails to produce a sufficient supply of hormones needed for good health. Whether the problem is caused by the thyroid conditions or y the pituitary gland, the result is that the thyroid is under producing hormones, causing many physical and mental processes to become sluggish. The body consumes less oxygen and produces less body heat.

Hypothyroidism is a condition in which the thyroid gland does not make enough thyroid hormones, characterized by a reduction in metabolic rate. The main symptoms of hypothyroidism are fatigue, weakness, increased sensitivity to cold, constipation, unexplained weight gain, dry skin, hair loss or coarse dry hair, muscle cramps and depression. However, most symptoms take years to develop. The slower the metabolism gets, the more obvious the signs and symptoms will become. If hypothyroidism goes untreated, the signs and symptoms could become severe, such as a swollen thyroid gland (goiter), slow thought processes, or dementia. (Hypothyroidism. The American Thyroid Association). Subclinical hypothyroidism, an often under-diagnosed thyroid disorder, manifests as elevated TSH, normal T4 and normal T3 levels. Individuals with subclinical hypothyroidism are at greater risk for developing overt hypothyroidism. (Garduno-Garcia et al. Eur J Endocrinol. 2010 August; 163(2): 273-8.

It has been estimated that about 20% of women over the age of 60 suffer from subclinical hypothyroidism. (Wilson G R, et. al, Am Fam Physician. 2005 Oct. 15; 72(8): 1517-24.

There is evidence that the standard blood TSH test reference range may cause many cases of hypothyroidism to be missed. Most physicians accept a reference range for TSH between 0.45 and 4.5 µIU/mL to indicate normal thyroid function. In reality, though, a TSH reading of more than 2.0 may indicate lower-than-optimal thyroid hormone levels. Various TSH levels that fall within normal range are associated with adverse health outcomes.

TSH greater than 2.0 leads to increased 20-year risk of hypothyroidism and increased risk of thyroid autoimmune disease. TSH between 2.0 and 4.0: hypercholesterolemia and cholesterol levels decline in response to T4 therapy TSH greater than 4.0: greater risk of heart disease. ((Tunbridge W M, et. al, Clin Endocrinol (Oxf). 1977 December; 7(6): 481-93).

Consequences of Hypothyroidism

Gastrointestinal problems. Hypothyroidism is a common cause of constipation. Constipation in hypothyroidism may result from diminished motility of the intestines. In some cases, this can lead to intestinal obstruction or abnormal enlargement of the colon.[36] Hypothyroidism is also associated with decreased motility in the esophagus, which causes difficulty swallowing, heartburn, indigestion, nausea, or vomiting. Abdominal discomfort, flatulence, and bloating occur in those with small intestinal bacterial growth secondary to poor digestion. Depression and psychiatric disorders. Panic disorders, depression, and changes in cognition are frequently associated with thyroid disorders. Hypothyroidism is often misdiagnosed as depression. (Hennessey J V, et. al, J Fam Pract. 2007 August; 56(8 Suppl Hot Topics): S31-9.

Cognitive decline. Patients with low thyroid function can suffer from slowed thinking, delayed processing of information, difficulty recalling names, etc. Patients with subclinical hypothyroidism show signs of decreased working memory, and decreased speed of sensory and cognitive processing. An evaluation of thyroid hormones along with TSH may help avoid misdiagnosis as being depressed. (Kritz-Silverstein D, et. al, J Nutr Health Aging. 2009 April; 13(4): 317-21.

Hypothyroidism and subclinical hypothyroidism are associated with increased levels of blood cholesterol, increased blood pressure, and increased risk of cardiovascular disease. Even those with subclinical hypothyroidism were almost 3.4 times as likely to develop cardiovascular disease than those with healthy thyroid function. Hypertension is relatively common among patients with hypothyroidism. (Duntas L H, et. al, Semin Thromb Hemost. 2011 February; 37(1): 27-34.

The risk of heart disease increases proportionally with increasing TSH, even in subclinical hypothyroidism. Hypothyroidism that is caused by autoimmune reactions is associated with stiffening of the blood vessels. Thyroid hormone replacement may slow the progression of coronary heart disease by inhibiting the progression of plaques. (Perk M, et. al, Can J Cardiol. 1997 March; 13(3): 273-6).

Overt and subclinical hypothyroidism are both associated with increased levels of low-grade inflammation, as indicated by elevated C-reactive protein (CRP). (Christ-Crain M, et. al, Atherosclerosis. 2003 February; 166(2): 379-86).

Metabolic Syndrome. In a study of more than 1500 subjects, researchers found that those with metabolic syndrome had statistically significantly higher TSH levels (meaning lower thyroid hormone output) than healthy control subjects. Subclinical hypothyroidism was also correlated with elevated triglyceride levels and increased blood pressure. Slight increases in TSH may put people at higher risk for metabolic syndrome. (Lai Y, Wet. al, Endocr J. Epub 2010 Nov. 30).

Reproductive system problems. In women, hypothyroidism is associated with menstrual irregularities and infertility. Proper treatment can restore a normal menstrual cycle and improve fertility. (Poppe K, et. al, Clin Endocrinol (Oxf). 2007 March; 66(3): 309-21.

Fatigue and weakness. The well-known and common symptoms of hypothyroidism, such as chilliness, weight gain, paresthesia (tingling or crawling sensation in the skin) and cramps are often absent in elderly patients compared with younger patients, and fatigue and weakness are common in hypothyroid patients. Studies show that 90% of people with hypothyroidism are producing antibodies to thyroid tissue. This causes the immune system to attack and destroy the thyroid, which over time causes a decline in thyroid hormone levels. (Doucet J, et. al, J Am Geriatr Soc. 1994 September; 42(9): 984-6).

This autoimmune form of hypothyroidism is called Hashimoto's disease. It is a century since Dr. Hakaru Hashimoto (1881-1934) described the thyroid condition that still bears his name. In that time, considerable efforts have been made to understand the pathogenesis of this common disease and, since 1956; Hashimoto thyroiditis has become the archetype of autoimmune destructive disorders and autoantibody production. Autoimmune thyroid diseases (AITD) are the commonest autoimmune endocrine diseases. Hashimoto's thyroiditis is the most common cause of low thyroid function in the United States. The body's immune system mistakenly attacks the thyroid tissue impairing the ability to make hormones. Hypothyroidism caused by Hashimoto's disease is treated with thyroid hormone replacement agents.

Hashimoto's disease usually causes hypothyroidism, but may also trigger hyperthyroid symptoms. (Lorini R, et. al, Pediatr Endocrinol Rev. 2003 December; 1 Suppl 2:205-11; discussion 211).

Hyperthyroidism is usually caused by Graves' disease, in which antibodies are produced that bind to TSH receptors in the thyroid gland, stimulating excess thyroid hormone production. The distinction between Hashimoto's thyroiditis and Graves' disease may not be as important as once thought. Hashimoto's and Graves' disease are different expressions of a basically similar autoimmune process, and the clinical appearance reflects the spectrum of the immune response in a particular patient. The two diseases can overlap causing both thyroid gland stimulation and destruction simultaneously or in sequence. (McLachlan S M, et. al, Endocrinology. 2007 December; 148(12): 5724-33).

Some clinicians consider the two conditions different presentations of the same disease. About 4% of patients with Graves' disease displayed some symptoms of Hashimoto's thyroiditis during childhood. (Wasniewska M, et. al, Horm Res Paediatr. 2010; 73(6): 473-6).

Pregnant women are especially at risk for hypothyroidism. During pregnancy, the thyroid gland produces more thyroid hormone than when a woman is not pregnant, and the gland may increase in size slightly. Uncontrolled thyroid dysfunction during pregnancy can lead to preterm birth, mental retardation, and hemorrhage in the postpartum period. It is important to work closely with a physician to monitor thyroid function during pregnancy. (Costeira M J, wet. al, Thyroid. 2010 September; 20(9): 995-1001).

Tests to diagnose and monitor hypothyroidism include: Thyroid Stimulating Hormone (TSH), Total T4, Total T3, Free T4 (fT4), Free T3 (fT3), Reverse T3 (rT3), Thyroid peroxidase antibody (Tope), Thyroglobulin antibody (TgAb) (Huber A, et. al, Endocr Rev. 2008; 29:697-725), and according to one study Auto immune thyroid disease (AITD) are the commonest autoimmune diseases in the USA; (Jacobson D L, et. al, Clin Immunol Immunopathol. 1997; 84:223-243).

Hashimoto's is the most common autoimmune disorder in the U.S., affecting between 7-8% of the population. While not all people with Hashimoto's have hypothyroid symptoms, thyroid antibodies have been found to be a marker for future thyroid disease. There are no effective treatments for autoimmune disease. They use steroids and other medications to suppress the immune system in certain conditions with more potentially damaging effects, such as multiple sclerosis, rheumatoid arthritis and Crohn's disease.

So the standard of care for a Hashimoto's patient is to simply wait until the immune system has destroyed enough thyroid tissue to classify them as hypothyroid, and then give them thyroid hormone replacement. If they start to exhibit other symptoms commonly associated with their condition, like depression or insulin resistance, they get additional drugs for those problems. The obvious shortcoming of this approach is that it doesn't address the underlying cause of the problem, which is the immune system attacking the thyroid gland.

Hashimoto's thyroiditis is an autoimmune disease characterized by hypothyroidism and asymmetric thyroid growth. Positive serologic testing of antithyroid peroxidase (anti-TPO) antibody and/or anti-thyroglobulin (anti-TG) antibody supports the clinical diagnosis. Hashimoto encephalopathy is a rare steroid-responsive disorder associated with Hashimoto thyroiditis, resulting in a variety of clinical manifestations ranging from behavioral and cognitive changes, myoclonus, seizures, pyramidal tract dysfunction, involuntary movements, and cerebellar signs to psychosis and coma, with relapsing and progressive course (Watemberg N, et. al, J Child Neurol 2006; 21:1-5; Alink J, et. al, Acta Paediatr 2008; 97:451-3).

Hashimoto encephalopathy should be considered in any patient presenting with an acute or sub acute unexplained encephalopathy, or in patients with diffuse cognitive decline followed by a progressive or relapsing-remitting course. Measurement of antithyroid antibodies is essential to making the diagnosis and should be undertaken in any such patient, even when standard thyroid function test findings are normal.

One of the biggest challenges facing those with hypothyroidism is that the standard of care for thyroid disorders in both conventional and alternative medicine is hopelessly inadequate.

The goal of patients with thyroid disorders and the practitioners who treat them is to find that single substance that will reverse the course of the disease. For doctors, this is either synthetic or bio-identical thyroid hormone. For the alternative types, this is iodine.

Unfortunately, in the vast majority of cases neither approach is effective. Patients may get relief for a short period of time, but inevitably symptoms return or the disease progresses.

Autoimmune thyroid dysfunctions remain a common cause of both hyperthyroidism and hypothyroidism in pregnant women. Graves disease accounts for more than 85% of all cases of hyperthyroid, whereas Hashimoto thyroiditis is the most common cause of hypothyroidism.

Graves disease is an autoimmune disease characterized by hyperthyroidism due to circulating autoantibodies. Thyroid-stimulating immunoglobulin's (TSIs) bind to and activate thyrotropin receptors, causing the thyroid gland to grow and the thyroid follicles to increase synthesis of thyroid hormone. Graves disease, along with Hashimoto thyroiditis, is classified as an autoimmune thyroid disorder.

In some patients, Graves disease represents a part of more extensive autoimmune processes leading to dysfunction of multiple organs (e.g., Polyglandular autoimmune syndromes). Graves disease is associated with pernicious anemia, vitiligo, diabetes mellitus type 1, autoimmune adrenal insufficiency, systemic sclerosis, myasthenia gravis, Sjögren syndrome, rheumatoid arthritis, and systemic lupus erythematous. (Stassi, et al., 2002, *Nature Reviews Immunology*, 2:196).

Thyroid malfunction can lead to Hashimoto's disease, also known as chronic lymphocytic thyroiditis, where the immune system attacks the thyroid gland. The resulting inflammation often leads to an under active thyroid gland (hypothyroidism) (Wondisford, *Clinica Management of Thyroid Diseases*, ISBN: 978-1-4160-4745-2, Copyright © 2009 by Saunders. Philadelphia). Thyroid hormone (TH) is critical in heart maturation during development appears to have a reparative role in adult life (Mourouzis. I, et al., 2011, *Journal of Thyroid Research*, Volume 2011, Article ID 958626).

Changes in cardiac parameters encountered in hyperthyroidism result from the activity of thyroid hormone on certain molecular pathways in the heart and vasculature. The main mode of action is a direct effect on the transcription of specific and nonspecific cardiac genes. The second is a nongenomic action on plasma membranes, mitochondria, and the sarcoplasmic reticulum (Davis P J, et al., 1996, *Thyroid*, 6:497-504).

Diabetes and thyroid disease are both endocrine, or hormone, problems. When thyroid disease occurs in diabetes patients, it can make blood glucose control more difficult. Almost one third of people with type 1 diabetes, have been found to have thyroid disease. This is because type 1 diabetes and the most common thyroid disorders are autoimmune diseases, which are diseases in which the immune system attacks a gland or organ of the body. People with an autoimmune disease are more likely than the general population to develop other autoimmune diseases, such as Addison disease, pernicious anemia, rheumatoid arthritis, or lupus.

Thyroid disorders are also common in type II diabetes because both of these illnesses tend to occur more frequently as people age (Wu. P., 2000, *Clinical Diabetes*, Vol. 18, No. 1).

Patients with ESRD have multiple alterations of thyroid hormone metabolism in the absence of concurrent thyroid disease. ESRD patients may have an increased frequency of goiter, thyroid nodules, thyroid carcinoma, and hypothyroidism (E. M. Kaptein, 1996, *Endocrine Reviews*, 17(1):45-63).

Anemia and Blood Count Disorders

Anemia, commonly defined as a hemoglobin level of <12 g/dL, occurs in over 30% of cancer patients at any point in time, and its incidence increases with treatment and progressive disease. (Littlewood. T. 2001: J Semin Oncol. 2001, Suppl 8, 49-53). A high prevalence of anemia was identified in this group of type 2 diabetic patients previously shown to have a high prevalence of the metabolic syndrome. (Ezenwaka, C. E., et al. 2008: Cardiovascular Diabetology 7:25) It has been demonstrated that patients with chronic anemia had a high cardiac output and a low systemic vascular resistance [Anand I. S, et al. 1993, Br Heart J, 70:357-362). In the long term, this may result in maladaptive left ventricular hypertrophy (LVH), which is a known risk factor for adverse cardiovascular outcome and all-cause mortality. (Sarnak M J, et al. 2001, J Am Coll Cardiol 2001, 38:955-962).

Anemia as a risk factor for cardiovascular disease and all-cause mortality in diabetes: Furthermore, anemia has been shown to be a risk factor for adverse cardiovascular outcomes in non-diabetic and diabetic patients and with chronic kidney disease. Rampersad M, 2004, Anemia in diabetes. Acta Diabetol 41, Suppl 1, S13-S17).

Chemotherapy directly targets cancer cells, it also affects our blood cells in the process—red blood cells, white blood cells, monocytes neutrophils and platelets. The treatment in addition leads to Anemia and low levels of Hemoglobin. These cells are manufactured in the bone marrow. During chemotherapy, bone marrow activity may be decreased, resulting in lowered blood cell counts within the body. White blood cells (WBC) generally drop to their lowest count about 7 to 14 days following a chemotherapy treatment. Thus there may need to delay chemo treatment or reduce your chemotherapy dose until your white blood cell count increases and the possibility of infection is reduced. In addition many prescription drugs can cause Neutropenia and lower platelet counts and cause lowered WBC levels There is evidence demonstrating significant relationships between concurrent measurements of hemoglobin level and fatigue severity in cancer patients. (Lind M, 2003: Br J Cancer 86:1243-1249).

Anemia is a common symptom and complication in patients with solid malignant tumors. (Means R T., et. al 1992, Blood 80: 1639-1647). In these patients anemia is multifactorial and may occur as either a direct effect of the cancer (blood loss, bone marrow infiltration or nutritional deficiencies), low WBC values and platelet count as a result of the cancer treatment itself, or due to chemical factors produced by the cancer (Mercadante S, et al. 2000: Cancer Treat Rev 26:303-311, 2000). Anemia can lead to a wide array of symptoms that could negatively affect patients' physical status and functional capacity and subsequently impair their quality of life (QOL). Notable among these symptoms are fatigue, dyspnea, palpitations and other cardiovascular complications, cognitive dysfunction, depression, nausea, sexual/reproductive dysfunction and impaired immune function (Ludwig H, et al. Semin Oncol 28: 7-14, 2001).

The incidence of tumor related anemia and its clinical value has been investigated in various human malignancies including breast cancer and gynecological cancer (Barrett-Lee P, et al., Oncologist 2005 10: 743-757). The treatment of tumor-related or chemotherapy-induced anemia with supplemental iron therapy or erythropoietin growth factor has been increasing in an attempt to improve the quality of life of patients with cancer (Rodgers G M, 2006, Oncology 20: 12-15).

A low pretreatment hemoglobin level has been shown to negatively influence outcome in the treatment of tumors of the cervix, bladder and head and neck by radiotherapy (Marchal C, et al., 2005, Cancer Radiother 9: 87-95; Kummel S, et al. 2006: Anticancer Res 26: 1707-1713).

Breast cancer is one of the most common carcinomas worldwide it also represents one of the most common indications for chemotherapy. (Jemal A, et al. (2005: 2005. CA Cancer J Clin 55: 10-30). The study findings suggest that reduced hemoglovin levels with resulting myelodysplacia and poorer tumor oxygenation could be implicated in the complex mechanisms of chemotherapy resistance in breast cancer (Boehm D. U, et al. 2007, Anti cancer research 27: 1223-1226).

Myelodysplasia (MDS)

Myelodysplastic syndromes (MDS) (Phillips et al., 2005, Ann. Rev Med; 56: 1-16) represent a collection of stem cell disorders characterized by impaired hematopoiesis resulting in low peripheral blood counts. MDS are associated with decreased production and abnormal function of cells, platelet decreases and patients may have symptoms that appear to be out of proportion to the level of cytopenia. Increased intracellular activity of matrix metalloproteinase in neutrophils may be associated with delayed healing of infection without neutropenia in Myelodysplastic syndromes. Zeidman A, et al. 2004, Ann. Hematol. 84:383-88).

The majority of patients with MDS are present with symptoms related to anemia. However, bleeding and infection are the most common causes of death. The median age of diagnosis is 72 and the median survival is 2.5 years.

MDS is thought to be clonal and are characterized by low blood counts and a risk of progression to acute myeloid leukemia (AML). The incidence rate of MDS in the United States for 2001 to 2003 was 3.3/100,000, and the overall three-year survival was 45% (Rollison D E, et al., 2008, Blood 112:45-52). The incidence increases with age, and the median age at diagnosis is 70-75 years. Men have a significantly higher incidence rate than women (4.5 versus 2.7 per 100,000 per year).

The majority of patients with MDS have macrocytic anemia with or without additional cytopenias present at the time of diagnosis. The differential diagnosis includes other causes of macrocytic anemia, such as vitamin B 12 and folate deficiencies, alcohol consumption, and thyroid disorders. The initial laboratory workup includes blood cell counts, serum ferritin levels, total iron binding capacity, serum iron levels, reticulocyte counts, and levels of vitamin B 12, red blood cell (RBC) folate, and thyroid stimulating hormone. Persistent unexplained cytopenias warrant additional investigation via bone marrow aspiration and biopsy, including cytogenetic testing and iron stains. Because MDS comprises a varied group of disorders with impaired hematopoiesis and variable prognosis, there is no routine method of care for all patients with MDS.

The drug therapy available today to treat MDS are Lenalidomide, azacitidine, and decitabine are all FDA-approved agents to treat MDS; however, the only potential cure for MDS remains stem cell transplantation which is expensive and has many side effects and there is need for a safe drug with minimum side effects.

Red Cell Distribution Width (RDW)

Red blood cells are made in the bone marrow. The red blood cell distribution width (RDW) is a measure of the variation of red blood cell (RBC) volume that is reported as part of a standard complete blood count. Usually red blood cells are a standard size of about 6-8 µm. Certain disorders, however, cause a significant variation in cell size. Higher RDW values indicate greater variation in size. Normal reference range in human red blood cells is 11.5-14.6%.

More recently, however, population studies have identified RDW as a predictor of all-cause (Cavusoglu E, et. al, Int J Cardiol 2010; 14:141-6. and cardiac mortality. (Lippi G, et. al, Clin Chem Lab Med 2009; 47:353-357).

RDW has also been noted to be associated with worsened renal function, (Lippi G, et. al, Scand J Clin Lab Invest 2008; 68:745) evidence of systemic inflammation, (Lippi G, et. al, Arch Pathol Lab Med 2009; 133:628-32) and poor outcomes in a variety of disorders, including stroke (Ani C, et. al, J Neurol Sci 2009; 277:103-8), pulmonary hypertension, (Hampole C V, et. al, Am J Cardiol 2009; 104:868-72) and cardiac failure. (Al-Najjar Y, et. al, Eur J Heart Fail 2009; 11:1155-62).

RDW has an affect on aging as seen in the study where shorter telomere lengths were seen associated with increased (RDW), (Julia Kozlitina, et. al, PLOS ONE, December 2012, Volume 7, e51046).

An Italian group (Fici et. al, J Cardiovasc Pharmacol, 2013; 62:388-393) evaluated the effects of Nebivolol and Metoprolol on the RDW in new essential hypertensive patients. After baseline assessment, 72 patients were randomly allocated to 5 mg/d of Nebivolol (n=37, 20 men) or 100 mg/day of Metoprolol (n=35, 18 men) and treated for 6 months. The changes in RDW were minimal in Nebivolol it changed from 15.8 to 15 and in Metoprolol group from 15.6 to 15.45.

High level of circulating red cell distribution width (RDW) may reflect ongoing inflammation and no known therapy exists to correct this condition caused by this bone marrow condition.

Rheumatoid Arthritis

In company with tuberculosis, trachoma, and a few other diseases, the rheumatic diseases are among the oldest known afflictions of mankind. Importantly, in the latter group rheumatoid arthritis (RA) ranks as perhaps the earliest to be clearly described and documented by physicians.

Rheumatoid arthritis (RA) is an autoimmune disorder that poses a significant public health burden because of its prevalence, direct and indirect costs, the debilitating nature of the disease, and the fact that there is no cure. It is a long-term disease that causes pain, stiffness, swelling, and limited motion and function of many joints, leading to substantial loss of functional mobility due to pain and joint destruction. The exact cause of RA is unknown, but genetic, hormonal, and environmental factors are believed to be involved. (DiPiro J. T, et al. Pharmacotherapy: A Pathophysiologic Approach. 7th Ed. New York: McGraw-Hill Medical; 2008: section 12).

Although the incidence and prevalence of RA in populations have varied over time and noted fluctuations exist between geographic locations, a 2010 study by the American College of Rheumatology (ACR) found that an estimated 1.5 million Americans were affected by RA in 2005, with an overall incidence rate of 40.9 per 100,000 population. About 75% of those affected are women, and although RA most often appears in patients between age 40 and 60 years, its onset can occur at any age. (American College of Rheumatology. Rheumatoid arthritis fact sheet. Published August 2012.) With an aging population, we can expect continued growth in the prevalence of RA.

Estimates of the direct and indirect costs of RA vary and are partly dependent on the severity of the disease. Research evidence suggests the adjusted average annual total medical expenditure for RA in 2008 was approximately $13,000 per patient, including an average pharmacy expenditure of $5825. While these figures are significantly higher than what would be recorded in a non-RA control group, the majority of patients with RA at that time were being treated with conventional (non biologic) disease-modifying anti-rheumatic drugs (DMARDs). The use of a biologic DMARD can more than double pharmacy costs; the annual cost of therapy for those patients using tumor necrosis factor (TNF) antagonists in 2008 ranged from roughly $10,000 to $14,000 annually, 5 at which time the estimated total direct medical expenditures for RA were $73.4 billion. Indirect costs of the disease include lost productivity due to work-related disability, increased morbidity, and shortened survival. Between 25% and 50% of all patients with RA are unable to work within 20 years of being first diagnosed. (Mikuls T. Arthritis Rheum. 2010; 62(6); 1565-1567).

RA is considered to be a chronic progressive systemic condition that affects mainly diarthrodial joints. The most common, but by no means universal, mode of onset involves symmetrical pain and swelling in small joints of hands and feet, and its inception can and does vary widely among individuals. RA may begin with marked systemic symptoms including fatigue, fever, and weight loss, and slowly over weeks to months present the more classic symptoms of joint pain and swelling. Some common extra-articular manifestations of RA include parenchymal lung disease, secondary Sjögren's syndrome, cutaneous vasculitis, and pericarditis. (Turesson C., Ann Rheum Dis. 2003; 62: 722-727).

The primary therapeutic strategy is to detect the relevant synovial and other pathogenic processes early in their development, and to treat quickly and aggressively to prevent long-term joint damage. A full metabolic panel and complete blood count with differential and inflammatory biomarkers (erythrocyte sedimentation rate [ESR]/C-reactive protein) are often done, and they often are elevated in patients with RA. Two antibodies, rheumatoid factor (RF) and anti cyclic citrullinated peptide (anti-CCP) also appear elevated and accompany the diagnostic protocol; however RF, and to a lesser extent anti-CCP, are sometimes seen in other disease states or even in healthy individuals, and thus these may not serve as completely specific markers for RA in each and every case. (Van Venrooij W J, Ann N Y Acad Sci. 2008; 1143:268-285; Lee A N, Clin Lab Sci. 2008; 21:15-18: Renaudineau Y, Autoimmunity. 2005; 38:11-16).

RA pathogenesis also includes a significant an important autoimmune component of populations of T cells which recognize self-tissue escape clonal deletion in the thymus and thereafter are available to react with self-peptides in the RA joint. Auto reactive T cells are known to persist in normal individuals, and under the appropriate stimulus such auto reactive cells can initiate anti self-immune responses. (Kreuwel H T, et. al, Curr Opin Immunol. 2001; 13:639-643.) Further, pathogen peptides that have a similar sequence and/or structure to host peptides may be expressed in the synovia of some RA patients where they are recognized by auto reactive T cells. (Prakken B J, et. al, Curr Dir Autoimmun. 2001; 3:51-63).

Malfunctioning B cells also can produce antibodies directed against host peptides. For example RF, an antibody directed against the Fc portion of immunoglobulin G (IgG) molecules, is present in approximately two thirds of patients with RA. (Lee A N, et. al, Clin Lab Sci. 2008; 21:15-18).

Although the presence of RF is used for diagnostic purposes, 10% of healthy individuals and many patients with other autoimmune disorders, including Sjögren's syndrome, systemic lupus erythematous (SLE), and mixed connective tissue disease, also express RF. In addition, approximately 70% of patients with disease due to chronic hepatitis C virus are RF positive. (Newkirk M M. J. Rheumatol. 2002; 29:2034-2040; Nowak U, et. al, Clin Exp Immunol. 2007; 147: 324-329).

The diagnostic protocol for RA has included laboratory testing for RF for more than 50 years, but the presence of RF as a marker for RA in patients is considered unreliable due to its presence in the general population and in other autoimmune and infectious diseases. Decline in RF levels may be useful, however, as an indicator of a given patient's response to treatment when various disease modifying anti rheumatic drugs and other biologics, such as Infliximab or Rituximab, are administered.

Autoantibodies to citrullinated proteins provide a useful and quite specific diagnostic indicator for RA. The anti-CCP antibody is present in approximately 80% of RA patients and is quite specific for the disorder. (Van Venrooij W J, et. al, Anti-CCP antibody, a marker for the early detection of rheumatoid arthritis. Ann N Y Acad Sci. 2008; 1143:268-285.); Moreover, this autoantibody is detected in less then 1% of healthy individuals; it can even appear before RA is clinically evident and detectable.

The treatment of RA has evolved dramatically over the past few decades. The main goal of treatment is to control pain and inflammation, and ultimately slow the progression of joint destruction, on the basis of a stepped-care approach. Patients are initially treated with rest, exercise, physical and occupational therapy, and non-steroidal anti-inflammatory drugs. This step is followed by more aggressive treatment; American College of Rheumatology (ACR) recommends the use of conventional DMARDs and/or biologic DMARDs (biologics) depending on the stage/progression of the disease, efficacy of the current treatment, and presence of other comorbid conditions, among other factors. (Saag K G, et al; Arthritis Rheum. 2008; 59(6): 762-784). Therapeutic agents in current use for treatment of patients with RA, Auranofin, azathioprine, gold sodium Thiomalate, hydroxychloroquine, Leflunomide, and methotrexate. Biologics used are the anti-TNFs Adalimumab, Anakinra, Certolizumab, Etanercept, Golimumab, and Infliximab, and the non-TNFs Abatacept, Rituximab, and Tocilizumab.

Therapeutic agents in current use for treatment of patients with RA including those targeting TNFα or its receptor, lack universal efficacy, indicating significant heterogeneity in the detailed pathogenic processes among those patients.

Malaria

Malaria remains one of the most prevalent and deadly infectious diseases across Africa, Asia, and the Americas. The World Health Organization (WHO) estimates 154-289 million malaria cases in 2010, with 660,000 associated deaths (WHO, World Malaria Report 2012) The mortality is twice as high when including cases of malaria that are undiagnosed or untreated (Murray, C. J.; et. al, Lancet 2012, 379, 413). Eighty percent of the estimated cases occur in sub-Saharan Africa and 86% of deaths occur in children less than 5 years of age.

Several species of *Plasmodium* cause malaria in humans: *Plasmodium falciparum, Plasmodium vivax, Plasmodium ovale, Plasmodium malariae* and the simian *Plasmodium knowlesi*. The most lethal species is *P. falciparum*, found predominantly in Africa (Gething, P. W., and et. al, Malar. J. 2011, 10, 378). If left untreated, *P. falciparum* causes organ failures (severe malaria) and accumulate s in the brain capillaries (cerebral malaria), leading to coma and eventually death.

The parasite has a complex life cycle and in order to eradicate the disease, every stage should be considered for treatment:

a. Liver stage. Once the mosquito inoculates the parasites (sporozoites) into the blood stream, the parasites invade the liver within 30 min and start replicating there. Drugs that target the liver stages are important to prevent the disease from developing (prophylactic treatment)

b. Blood stage. After approximately 5-10 days, the liver cells burst and merozoites invade the red blood cells where they rapidly proliferate, causing the symptomatic high fevers and the pathology. In their intraerythrocytic phase, the merozoites go through various forms (rings, trophozoites, and schizonts to form an average of 20 daughter merozoites that are released into the bloodstream and infect new red blood cells. Drugs that target the blood stages are important to control the symptom s of the disease and associated mortality.

c. Transmission stage. After several cycles of asexual reproduction, some parasites further differentiate into male and female gametocytes, which contain only a half set of chromosomes.

d. Mosquito stage. When ingested by mosquitoes, the male and female gametocytes fuse in the midgut to form a zygote that further develops into new sporozoites ready for the next human host. Thus, in humans, the parasite replicates rapidly and asexually introducing replication errors and a small subset of genetic mutations; while in the mosquito, the sexual fusion of the gametocytes introduces large genetic variations, and increases the Darwinian fitness of the parasite prior to its invasion of another human Drugs that target the transmission and mosquito stages are important to prevent the infection of other humans, and would benefit an eradication agenda.

Artemisinin based combination therapies (ACTs) are the current standard of care for uncomplicated is the only drug approved to eliminate hypnozoites. As for prophylactic treatment, Atovaquone, Proguanil Malarone, (GlaxoSmith Kline) is usually preferred because it is well tolerated, but is expensive. (Dondorp, A. M, et. al, (Nat. Rev. Microbiol. 2010, 8, 272). have documented the resistance against the many existing antimalarials, and especially troubling is the emerging resistance to artemisinins.

The challenge is that drug resistance is not the only feature. New, innovative drugs should also
(I) be fast acting,
(ii) be safe for children and pregnant women, and
(iii) ideally be amenable to a single-dose administration.
An example of how difficult it is to combine all these features is seen in mefloquine. It is the only registered drug effective in a single dose however, drug resistance is problematic. Similarly, the only marketed antimalarial drug combination effective as a single dose is Sulfadoxine pyrimethamine, but it also suffers from drug resistance. (Sibley, C. H., et. al. Trends Parasitol. 2001, 17, 582.

There is an urgent need for developing new anti-malarial drugs. The new drugs can target the blood stage of the disease to alleviate the symptoms, the liver stage to prevent relapses, and the transmission stage to protect other humans. They need to be safe at low and high doses and not develop resistance.

Viall, et. al. (Molecular and Biochemical Parasitology, 5 (1982) 189-198), demonstrated that low doses of 25-hydroxy vitamin D3, 1-hydroxy Vitamin D-3 and 1,25dihydroxy Vitamin D-3 and higher levels of vitamin D-2 and D-3 are inhibitory to growth of *P. falciparum* in culture. The thresholds for inhibition varied by a factor 100 from 1-hydroxy Vitamin D ($2.5 \times 10^{-6}$) to $5 \times 10^{-6}$ M) to vitamin D-3 ($10^{-4}$ to $2.5 \sim 10^{-4}$ M and except for D-2 were always very narrow.

Since Metadichol is an inverse agonist of Vitamin D it was tested and found to have in vitro activity against Malaria with an IC 50 of 500 nm. (FIG. 2).

MRSA (Methicillin Resistant *Staphylococcus aureus*)

*Staphylococcus aureus* is a Gram positive, coagulase positive coccus in the family Staphylococcaceae. Methicillin-resistant *S. aureus* strains are resistant to methicillin and essentially all other beta-lactam antibiotics. Methicillin-resistant *Staphylococcus aureus* (MRSA) is a formidable bacterial pathogen responsible for a variety of infections commonly seen in patients of all ages (Chambers H F, et al., 2001, *Emerg Infect Dis;* 7:178-82; Lowy F. D., et al., *N Engl J Med,* 1998, 339:520-32; Frank A L, et al., *Clin Infect Dis,* 1999; 29: 935-6).

MRSA has spread worldwide and are now the most commonly identified antibiotic-resistant bacteria in hospitals in Europe, the Americas, North Africa, and the Middle- and Far-East. Approximately 478,000 hospitalizations in the U.S. in 2005 were associated with *S. aureus* infections and 58% of those (278,000) were caused by MRSA. (Klein E, et al., 2007, *Staphylococcus aureus*, United States, 1999-2005, *Emerg Infect Dis,* 13:1840-1846); Kock R, *Euro Surveill.,* 2010, 15(41)).

According to several studies, (David M Z, et al., 2010, *Clin Microbiol Rev,* 23:616-687) approximately 50% of people in the general population are carriers of *S. aureus*. However, CDC estimates that only about 1.5% of the population are carriers of MRSA. While many people harboring *S. aureus* are asymptomatic, they may pass these bacteria to others directly or contaminate food, clothing, towels, and other surfaces. Carriage of MRSA increases risk for serious infections that are difficult and more expensive to treat. Increasingly MRSA infections are acquired outside of healthcare settings, an effective MRSA control program will need to address prevention of infections arising in the community as well methods to control infections in hospitals. With the evolution of CA-MRSA strains and animal-associated MRSA strains, infections acquired outside of healthcare institutions, in the community, were caused by a more diverse array of strains of MRSA.

Acquisition of this organism is typically associated with particular settings (health care institutions, such as hospitals and long-term care facilities) and patient groups (patients with prolonged hospitalization, past antimicrobial use, indwelling catheters, decubitis ulcers, postoperative surgical wounds, and use of intravenous drugs or treatment with enteral feedings or dialysis) (Graffunder E M, et al., 2002, *J Antimicrob Chemother,* 49:999-1005).

Infections due to MRSA present a considerable dilemma to clinicians, since therapeutic options are limited and suboptimal dosing contributes to heightened mortality and increased length of hospital stay (Lodise T P. et al., 2003, *Clin Infect Dis,* 36:1418-23). Although alteration of Methicillin-resistant *Staphylococcus aureus* (MRSA) is a common bacterial pathogen responsible for a variety of infections in both children and adults, treatment of infections caused by this organism is problematic due to its resistance to many drugs. Recent reports of community-associated MRSA (CA-MRSA) infections in patients with no known risk factors have serious public health implications. Therapeutic options for these infections are limited; therefore, the potential exists for high morbidity and mortality In people, *S. aureus* is an opportunist. MRSA can cause the same types of infections as other isolates of *S. aureus*. This organism can be involved in a wide variety of skin and soft tissue infections including impetigo, folliculitis, furunculosis, cellulitis, and abscesses and wound infections. (Boucher H, et al., *Clin Infect Dis.,* 2010, 51, Suppl 2, S183-97). MRSA can also cause invasive infections such as pneumonia, endocarditis, septic arthritis, osteomyelitis, meningitis and septicemia. (United States Food and Drug Administration, Center for Food Safety and Applied Nutrition. Food borne pathogenic microorganisms and natural toxins handbook.

FDA; 1992. *Staphylococcus aureus*. In healthy people, the community-associated strain USA300 (CMRSA10) has been linked to cases of necrotizing pneumonia after influenza virus infections. Strains of *S. aureus* that carry the exotoxin TSST-1 can cause toxic shock syndrome, a life-threatening disease characterized by a sudden onset of high fever, rash, desquamation, hypotension and multiple organ failure (Fitzgerald J R, et al., 2001, *Proc Natl Acad Sci USA*, 98(15): 8821-6). Skin infections caused by *S. aureus* are generally believed to follow colonization of the skin or nares of the host. MRSA infections commonly occur where there is a break in the skin (for example, a cut or wound), especially in areas covered by hair (for example, the beard area, back of the neck, armpit, groin, legs, or buttocks). MRSA may look like a bump on the skin that may be red, swollen, warm to the touch, painful, filled with pus, or draining. The pus or drainage contains the infectious bacteria that can be spread to others. Several cases of impetigo, bullous impetigo, and scalded skin syndrome have been described, adding a new clinical presentation to community-acquired MRSA infection. (Liassine N, et al. 2004, *J. Clin Microbiol*, 42: 825-28).

EXAMPLES

Example 1

In various embodiments, the invention provides Metadichol® a Nano formulation of Policosanol described in U.S. patent application Ser. No. 12/691,706. Metadichol® liquid formulation used in studies as disclosed in U.S. patent application Ser. No. 12/691,706.

| COMPONENT | Percentage |
| --- | --- |
| Vitamin E TPGS | 4 |
| Policosanol | 1 |
| Sugar ester | 0.95 |
| Potassium sorbate | 0.12 |
| Sodium benzoate | 0.2 |
| Citric acid anhydrous | 0.1 |
| Water | 93.63 |

Composition of Metadichol® Gel

| Ingredient | Percentage |
| --- | --- |
| Water | 93 |
| Sucrose ester | 1 |
| Policosanol | 1 |
| Vitamin E TPGS | 3.5 |
| Preservatives citric acid | 0.5 |
| Carbopol Polymer | 1 |

The gel in this example was made by rapid stirring and mixing at 30-35° C., 0.5%-1% of the liquid Nano particle described earlier (U.S. patent application Ser. No. 12/691,706) with 1% to 3% by weight of Carbopol as described in Lubrizol Corporation Pharmaceutical Bulletin 22 Edition: May 31, 2011) and resulted in a clear gel containing 0.1-3% of active Nano particle ingredient ready for topical use.

The 1% policosanol formulation (liquid or in gel) described above was used to evaluate the effectiveness and tolerability and evaluating key biomarkers Clinical studies on patients, Metadichol® liquid formulation @10 mg per ml.

Example 1.1

Female 61 years old type 2 diabetic and insulin dependent with elevated levels of uric acid was treated with 20 mg of Metadichol®. At 4 weeks the uric acid had returned to normal levels.

Uric Acid (mg/dl)

| Baseline (mg/dl) | Week 4 | Week 52 |
| --- | --- | --- |
| 13 | 4.9 | 3.4 |

Example 1.2

Uric Acid (mg/dl)

Female 60 years old; Diabetic, Type 2 insulin dependent with mildly elevated Uric acid levels treated with 20 mg Metadichol® per day for 24 weeks.

| Baseline | Week 24 |
| --- | --- |
| 8.1 | 3.9 |

Example 1.3

Potassium (mmol/l)

Patient male 66 years old hypertensive patient with elevated potassium levels treated with Metadichol® @40 mg for 4 weeks.

| Baseline | Week 4 |
| --- | --- |
| 5.7 | 4.1 |

Example 1.4

Male 68 years old, hypertensive diagnosed with kidney damage. Beginning stages of kidney disease. Metadichol @10 mg per day only, was not on any other medication

| | Baseline | Week 1 | Week 2 | Week 6 | Week 12 |
| --- | --- | --- | --- | --- | --- |
| Potassium (mmol/l) | 6 | 5.2 | 4.3 | 4.8 | 4.2 |
| Phosphorus (mg/dl) | 5.2 | 5.2 | 3.3 | 3.3 | 3.6 |
| Bun (mg/dl) | 67 | | | 47 | 45 |
| Creatinine (mg/dl) | 4.6 | 2.99 | 3.1 | 3.1 | 3.3 |

Example 1.5

Patient male 63 years on kidney dialysis 3 days a week for 7 years waiting for a donor kidney and suffering from Diabetes and Hypertension and elevated levels of PTH, Alkaline Phosphate, Ferritin. elevated Phosphate levels and CA-P product levels, BUN ratios and Creatinine and Hemoglobin levels. Patient on kidney dialysis 3 days a week for the last 7 years waiting for a donor kidney.

Ferritin (ng/ml)

| Baseline | Week 18 | Week 32 |
|---|---|---|
| 532 | 492 | 325 |

Potassium (mmol/l)

| Baseline | Week 10 | Week 24 | Week 30 | Week 48 |
|---|---|---|---|---|
| 5.7 | 5.9 | 5.9 | 5.1 | 4.3 |

Alkaline Phosphatase (IU/L)

| Baseline | Week 18 | Week 30 | Week 38 | Week 44 |
|---|---|---|---|---|
| 148 | 111 | 85 | 74 | 65 |

Phosphorus Levels (mg/dl)

| Baseline | Week 6 | Week 14 | Week 24 | Week 30 | Week 32 | Week 48 |
|---|---|---|---|---|---|---|
| 6.8 | 5.6 | 6.3 | 4.8 | 4.9 | 4.9 | 4.0 |

PTH Levels (pg/ml)

| Baseline | Week 6 | Week 10 | Week 14 | Week 18 | Week 24 | Week 32 | Week 38 | Week 40 | Week 46 |
|---|---|---|---|---|---|---|---|---|---|
| 1033 | 873 | 1022 | 672 | 342 | 212 | 261 | 165 | 125 | 85 |

CA*P Product Levels. Normal Level Below 55 for Dialysis Patients and for Normal Patients 25-40.

| Baseline | Week 6 | Week 10 | Week 18 | Week 24 | Week 32 | Week 48 |
|---|---|---|---|---|---|---|
| 61.20 | 50.96 | 51.04 | 51.92 | 38.30 | 44.6 | 40.4 |

Blood Urea Nitrogen (mg/dl)

| Baseline | Week 6 | Week 10 | Week 18 | Week 32 | Week 48 |
|---|---|---|---|---|---|
| 50 | 45 | 40 | 33 | 33 | 21 |

Creatinine (mg/dl)

| Baseline | Week 10 | Week 18 | Week 25 | Week 30 | Week 32 | Week 48 |
|---|---|---|---|---|---|---|
| 10.4 | 9.98 | 8.9 | 8.7 | 8.7 | 8.7 | 1.1 |

Hemoglobin Levels (mg/dl)

| Baseline | Week 14 | Week 32 | Week 38 | Week 44 | Week 48 |
|---|---|---|---|---|---|
| 12.1 | 10.1 | 11 | 11.5 | 11.7 | 14.4 |

Example 1.6

Female 61 years insulin dependent diabetic treated with 20 mg of Metadichol® per day for 52 weeks.

Lp(a) (mg/dl)

| Baseline | Week 4 | Week 24 | Week 52 |
|---|---|---|---|
| 13 | 10.4 | 8.3 | 5.0 |

Example 1.7

Male 61 years old insulin dependent diabetic with elevated Lp(a) levels treated with 20 mg Metadichol® for 24 weeks Lp(a) (mg/dl)

| Baseline | Week 4 | Week 24 |
|---|---|---|
| 14 | 1.9 | 1.2 |

Example 1.8

Female 55 years old insulin dependent type 2 diabetic treated with 40 mg per day Metadichol® for 24 weeks.

Lp(a) (mg/dl)

| Baseline | Week 24 |
|---|---|
| 27 | 10.1 |

Example 1.9

Male 42 years old insulin dependent type 2 diabetic with elevated Lp(a) levels treated with Metadichol® 20 mg per day for 4 weeks.

Lp(a) (mg/dl)

| Baseline | Week 4 |
|---|---|
| 10.9 | 3.89 |

Example 2.0

Both Patients were type 2 diabetic and insulin dependent. Treated with Metadichol® @20 mg for 24 weeks.

Apo A Protein Levels (mg/dl)

| Patient | Baseline | Week 24 |
|---|---|---|
| Female 60 | 72 | 141 |
| Female 55 | 102 | 155 |

Example 2.1

Both Patients were type 2 diabetic and insulin dependent. Treated with Metadichol® @20 mg for 24 weeks.

ApoB: Apo A Ratio

| Patient | Baseline ratio | Week 24 |
|---|---|---|
| Male 60 years old | 1.1 | 0.79 |
| Female 55 years old | 1.53 | 0.83 |
| Female 60 years old | 0.8 | 0.4 |
| Male 52 years old | 0.74 | 0.4 |

Example 2.2 eGFR Levels (ml/min/1.73 M$^2$)

Female 55 years old insulin dependent type 2 diabetic.

| Baseline | Week 24 |
|---|---|
| 61 | 99 |

Example 2.3 eGFR Levels (ml/min/1.73 M$^2$)

Male 67 early stages of kidney disease was treated with Metadichol® 40 mg per day for 24 weeks. Normal for non African American male is above 60.

| Baseline | Week 24 |
|---|---|
| 47 | 67 |

Example 2.4 eGFR Levels (ml/min/1.73 M$^2$)

Male 68 years old type 2 non insulin diabetic treated with Metadichol® 40 mg for 60 weeks.

| Baseline | Week 60 |
|---|---|
| 70 | 135 |

Example 2.5 eGFR Levels (ml/min/1.73 M$^2$)

62 year old female type 2 non insulin dependent treated with Metadichol® @20 mg per day for 60 weeks.

| Baseline | Week 60 |
|---|---|
| 61 | 104 |

Example 2.6 eGFR Levels (ml/min/1.73 M$^2$)

Female 70, type 2 non insulin dependent diabetic treated with Metadichol® 40 mg for 39 weeks.

| Baseline | Week 39 |
|---|---|
| 42 | 87 |

Example 2.7

Patient Male 58 years old suffering from uncontrolled Hypertension for last 15 years unable to control with drugs That only made it worse and led to chronic Hepatitis with a elevated SGOT/SGPT ratios was treated with Metadichol® for 12 weeks at 20 mg per day.
Liver Enzymes SGOT/SGPT Ratio

| Baseline | Week 4 | Week 12 |
|---|---|---|
| 1.35 | 1.21 | 0.72 |

Example 2.8

Patient Male 49 years old, alcoholic, Diabetic, Hypertensive, Obese and hyperlipidemic and diagnosed as suffering from post necrotic Cirrhosis with a elevated SGOP/SGPT ratio treated with Metadichol® @20 mg per day for 60 weeks.
Liver Enzymes SGOT/SGPT Ratio

| Baseline | Week 12 | Week 60 |
|---|---|---|
| 1.89 | 0.72 | 0.64 |

Example 2.9

Male-62 years old was on Statins for 12 years diagnosed with a moderately elevated SGOT/SGPT ratio treated with Metadichol® 20 mg for 48 weeks.
Liver Enzymes SGOT/SGPT Ratio

| Baseline | Week 24 | Week 48 |
|---|---|---|
| 1.3 | 1.20 | 0.78 |

Example 3.0

84 year old Male lung cancer patient after chemotherapy has elevated SGOT/SGPT ratio. Metadichol® treatment for 24 weeks at 40 mg per day.
Liver Enzymes SGOT/SGPT Ratio

| Baseline before Chemotherapy | Level after 5 days of Chemo | Metadichol ® ® treatment for 24 weeks |
|---|---|---|
| 1.07 | 1.67 | 0.77 |

Example 3.1

Female 35, diagnosed with Gilbert's syndrome elevated Bilirubin levels Metadichol® @20 mg per day.

Total Bilirubin (mg/dl)

| Baseline | Week 3 | Week 24 | Week 84 |
|---|---|---|---|
| 1.7 | 1.4 | 0.6 | 0.5 |

D. Bilirubin (mg/dl)

| Baseline | Week 3 | Week 24 | Week 84 |
|---|---|---|---|
| 0.4 | 0.4 | 0.2 | 0.1 |

Example 3.2

Hemoglobin Levels (mg/dl)

Male 59 years Type 2 Insulin dependent Diabetic, with symptoms of constant fatigue with low Hemoglobin treated with Metadichol® 40 mg for 32 weeks.

| Baseline | Week 12 | Week 32 |
|---|---|---|
| 13.3 | 14.2 | 16 |

Example 3.3

Hemoglobin Level (g/dl)

Male-59 years old Type 2 diabetic 6 years and chronically fatigued treated with Metadichol® 20 mg for 24 weeks

| Baseline | Week 3 | Week 6 | Week 24 |
|---|---|---|---|
| 13.2 | 13.9 | 14.3 | 15 |

Example 3.4

Hemoglobin Levels (mg/dl)

Male 83 Lung cancer patient undergoing chemotherapy Metadichol® @40 mg per day.

| Baseline before Chemo | Hemoglobin after 5 days chemotherapy | Metadichol ® ® treatment for 24 weeks |
|---|---|---|
| 14 | 10.7 | 14 |

Example 3.5

Hemoglobin Level (mg/dl)

Type 2 diabetic 6 years and chronically fatigued treated with Metadichol® 40 mg for 24 weeks.

| Baseline | Week 3 | Week 6 | Week 24 |
|---|---|---|---|
| 13.2 | 13.9 | 14.3 | 15 |

Example 3.6

Platelet Count

Female 64 type 2 diabetic with a low platelet count treated with Metadichol® 20 mg daily for 36 weeks.

| Baseline | Week 6 | Week 26 |
|---|---|---|
| 123000 | 145000 | 189000 |

Example 3.7

Blood Count Disorders

Patient 69 year old male diagnosed with Neutropenia and extremely low monocyte count was diagnosed as in the beginning stages of Leukemia. Treated with Metadichol® 40 mg per day while waiting for a matching donor for a bone marrow transplant.

| | Baseline | 4 Weeks | 6 Weeks | 12 Weeks |
|---|---|---|---|---|
| Abs. Neutrophil | 0.4 | 0.36 | 0.43 | 0.90 |
| Abs monocyte | 0.019 | 0.36 | 0.50 | 0.46 |

Example 3.8

MDS Patient 65 year-old female with history of breast carcinoma, now with diagnosed with Myelodysplacia (MDS). Diagnosed with breast cancer 10 years ago and treatment was surgery, followed by chemo and radiation. Recent bone marrow test showed hypo-cellular marrow for age with progressive hematopoiesis with trilineage dysplastic megakaryocytes and increase in myeloblasts (~10%), consistent with Myelodysplacia (MDS) with excess of blasts. Diagnosis was that bone marrow is not functioning and needed chemotherapy and bone marrow transplant. Treated with Metadichol® @10 mg per day. Patient also suffered from hypothyroidism.

| | Baseline | Week 1 | Week 3 | Week 4 |
|---|---|---|---|---|
| WBC | 3.2 | 4.1 | 4.8 | 5.4 |
| Abs. Neutrophil | 0.67 | 1.2 | 1.92 | 2.04 |
| Platelet Count | 106000 | 140000 | 176000 | 153000 |
| Absolute monocytes | 0.3 | 0.39 | 0.70 | 1.35 |

TSH Levels

| | Baseline | Week 40 | Week 52 |
|---|---|---|---|
| TSH (mIU/L) | 3.19 | 3.48 | 0.72 |

Ferritin Levels

|  | Baseline | Week 2 | Week 4 | Week 6 | Week 8 | Week 10 | Week 16 |
|---|---|---|---|---|---|---|---|
| Ferritin (ng/ml) | 2847 | 1111 | 858 | 1326 | 1054 | 848 | 40 |

Example 3.9

Hypothyroidism

Female 74 years old diagnosed with hypothyroidism treated with Metadichol® 20 mgs for 24 weeks.
TSH (mIU/L)

| Baseline | Week 4 | Week 12 | Week 16 | 24 | Week 32 |
|---|---|---|---|---|---|
| 21.8 | 19 | 10.66 | 9.02 | 9.03 | 7.5 |

Example 4.0

Male 83 Lung cancer patient with Hypothyroidism undergoing Chemotherapy treated with Metadichol® @40 mg per day.
TSH Levels (mIU/L)

| Baseline | Week 4 | Week 12 |
|---|---|---|
| 7.6 | 6.1 | 2.83 |

Example 4.1

Kidney Disease Patients

Male 62 Male 62 years, obese, hypertensive, type 2 diabetic and on peritoneal dialysis for 1 year with kidney diseases, with symptoms of constant fatigue with low Hemoglobin treated with Metadichol® 10 mg per day. Improvements are noted below.
iPTH (Intact Parathyroid Hormone)

|  | Baseline | Week 6 | Week 14 | week 24 |
|---|---|---|---|---|
| iPTH (pg/ml) | 489 | 340 | 495 | 76 |

RDW (Red Cell Distribution Width)

|  | Baseline | Week 2 | Week 4 | Week 6 | Week 10 | Week 14 | Week 18 | Week 24 |
|---|---|---|---|---|---|---|---|---|
| RDW (%) | 15.7 | 15.6 | 15.6 | 15 | 14.4 | 14.7 | 14.2 | 12.8 |
| post dialysis weight (kg) | 96.6 | 93.4 | 90.3 | 88.5 | 88.6 | 86.3 | 79.9 | 77.6 |

Ca X P Product Levels.

|  | Baseline | Week 2 | Week 6 | Week 24 |
|---|---|---|---|---|
| Ca X P product | 40.67 | 36.96 | 33.6 | 34 |

Other Improvements in Key Biomarkers

|  | Baseline | Week 4 | Week 10 | Week 24 |
|---|---|---|---|---|
| Creatinine (mg/dl) | 7.01 | 5.65 | 5.66 | 3.6 |
| Phosphorus (mg/dl) | 4.9 | 4.4 | 4 | 3.8 |
| Potassium (mmol/l) | 4.4 | 4 | 3.3 | 3.5 |
| Iron (UG/DL) | 38 | 63 | 114 | 116 |
| Hemoglobin (g/dl) | 10 | 11.9 | 12.3 | 14 |

Example 4.2

Male 70 years on peritoneal dialysis for the past 2 years with elevated iPTH, RDW Ferritin, creatinine levels treated with Metadichol @10 mg per day. Improvements are noted below

|  | Baseline | Week 4 | Week 6 | Week 8 | Week 10 | Week 14 | Week 20 |
|---|---|---|---|---|---|---|---|
| iPTH (pg/ml) | 510 | 457 | 386 | 702 | 513 | 736 | 249 |
| RDW (%) | 23.1 | 20.1 |  | 15.1 | 14.6 |  |  |
| Ca * P product | 38.22 | 40.94 | 35.1 | 37.8 | 34.8 | 44.8 | 34.1 |
| Creatinine (mg/dl) | 8.37 | 6.85 | 7.87 | 7.47 | 8.08 | 7.72 | 7.39 |
| Phosphorus (mg/dl) | 4.6 | 4.2 | 3.9 | 4.3 | 3.9 | 5.1 | 3.8 |
| Potassium (mmol/l) | 5.2 | 4.46 | 5 | 4 | 4.2 | 4.3 | 4 |
| Iron (ug/dl) | 49 | 62 | 94 | 93 | 100 | 81 | 93 |
| BUN (blood urea and nitrogen) (mg/dl) | 53 |  | 54 | 63 | 60 | 50 | 43 |

Example 4.3

Hashimoto Disease 38 year old male with episodes of syncope associated with seizure activity, beginning in 2000 (13 years ago when he was 26). Neurological tests were normal. He has been averaging 150-155 systolic and 105-110 diastolic for the last 12 years. Was on anti seizure medications for 14 years. but episodes of seizure continued. In addition he suffered from double vision, auras and episodes of dizziness. Most episodes occurred during night while sleeping. Patient diagnosed with Hashimoto encephalopathy a year ago. Had elevated Thyroid hormone (TSH), elevated T4 and undetectable Thyroglobulin (TgAB) and elevated Thyroglobulin antibodies and Thyroperoxidase antibodies (TPOab). Treated with Metadichol @10 mg per day. After 4 weeks patient's original symptoms of double vision, aura and double vision and dizziness disappeared. His seizures have abated and generally after a seizure post Metadichol® treatment recovers in 15 minutes as opposed to 2 days previously. The patent has been able to wean himself off all medications and is on Metadichol @10 mg per day. Patient reports he is very energetic and feels less stressed mentally about his condition. Key biomarker improvements are shown below.

Systolic and Diastolic Blood Pressure in mm of Mercury

|  | Baseline | Week 1 | Week 2 | Week 4 | Week 6 | Week 8 | Week 12 |
|---|---|---|---|---|---|---|---|
| Systolic | 151 | 156 | 132 | 129 | 120 | 120 | 110 |
| Diastolic | 104 | 111 | 98 | 93 | 92 | 88 | 71 |

Thyroglobulin Antibodies (TgAb) (IU/ml) and Thyroglobulin (Micro Gram/ml)

|  | Baseline | Week 6 | Week 8 | Week 12 | Week 14 | Week 22 | Week 28 | Week 32 | Week 36 |
|---|---|---|---|---|---|---|---|---|---|
| Thyroglobulin antibodies (IU/ml) | 1276 | 1111 | 865 | 1011 | 845 | 511 | 524 | 83 | 65 |
| Thyroglobulin (ug/ml) | <0.2 | <0.2 | <0.2 | <0.2 | <0.2 | <0.2 | <0.2 | 0.35 | 14 |

Thyroperoxidase Antibodies (TPOab)

| Baseline | Week 8 | Week 12 | Week 22 | Week 28 | Week 32 | Week 36 |
|---|---|---|---|---|---|---|
| 20.4 (pg/ml) | 24 | <0.4 | <0.4 | 20 | 6 | <0.4 |

TSH Levels (mIU/L)

|  | Baseline | Week 8 | Week 16 | Week 18 | Week 20 | Week 22 | Week 24 | Week 32 | Week 36 |
|---|---|---|---|---|---|---|---|---|---|
| TSH (mIU/ml) | 6 | 3.6 | 3.91 | 5.11 | 4.23 | 3.17 | 3.81 | 0.9 | 1.12 |

Free T4 Levels;

|  | Baseline | Week 14 | Week 18 | Week 22 | Week 28 |
|---|---|---|---|---|---|
| Free T4 (ng/ml) | 2.9 | 1.5 | 1.08 | 1.33 | 1.312 |

Example 4.4

Male 56 years old diagnosed with slightly elevated PSA levels treated with Metadichol® 20 mg per day
PSA (ng/ml)

| Baseline | Week 6 | Week 14 | Week 24 |
|---|---|---|---|
| 5.0 | 4.3 | 3.5 | 3.25 |

Example 4.5

Male 59 with moderately elevated PSA levels treated with Metadichol® @20 mg per day PSA (ng/ml)

| Baseline | Week 8 | Week 24 | Week 40 |
|---|---|---|---|
| 16.31 | 11.06 | 13.19 | 12.49 |

Example 4.6

Patient male diagnosed with Rheumatoid arthritis for the past 18 years, in both knees with elevated RA factor (rheumatoid factor) CRP (C-reactive protein) and elevated ESR (erythrocyte sedimentation rate). Treated with Metadichol® 10 mg per day and the improvements are shown below. Patient reports improved mobility of both knees.

|  | Baseline | Week 24 | Week 28 |
|---|---|---|---|
| RA factor (IU/ml) | 698 | 182 | 167 |
| hs-CRP (mg/dl) | 82 | 3.8 | 1.1 |
| ESR (mm/hr.) | 105 | 103 | 80 |

Clinical Studies on Patients Metadichol® Gel Formulation and Skin Diseases. 1% Metadichol Used Example 4.7

Figure 3:
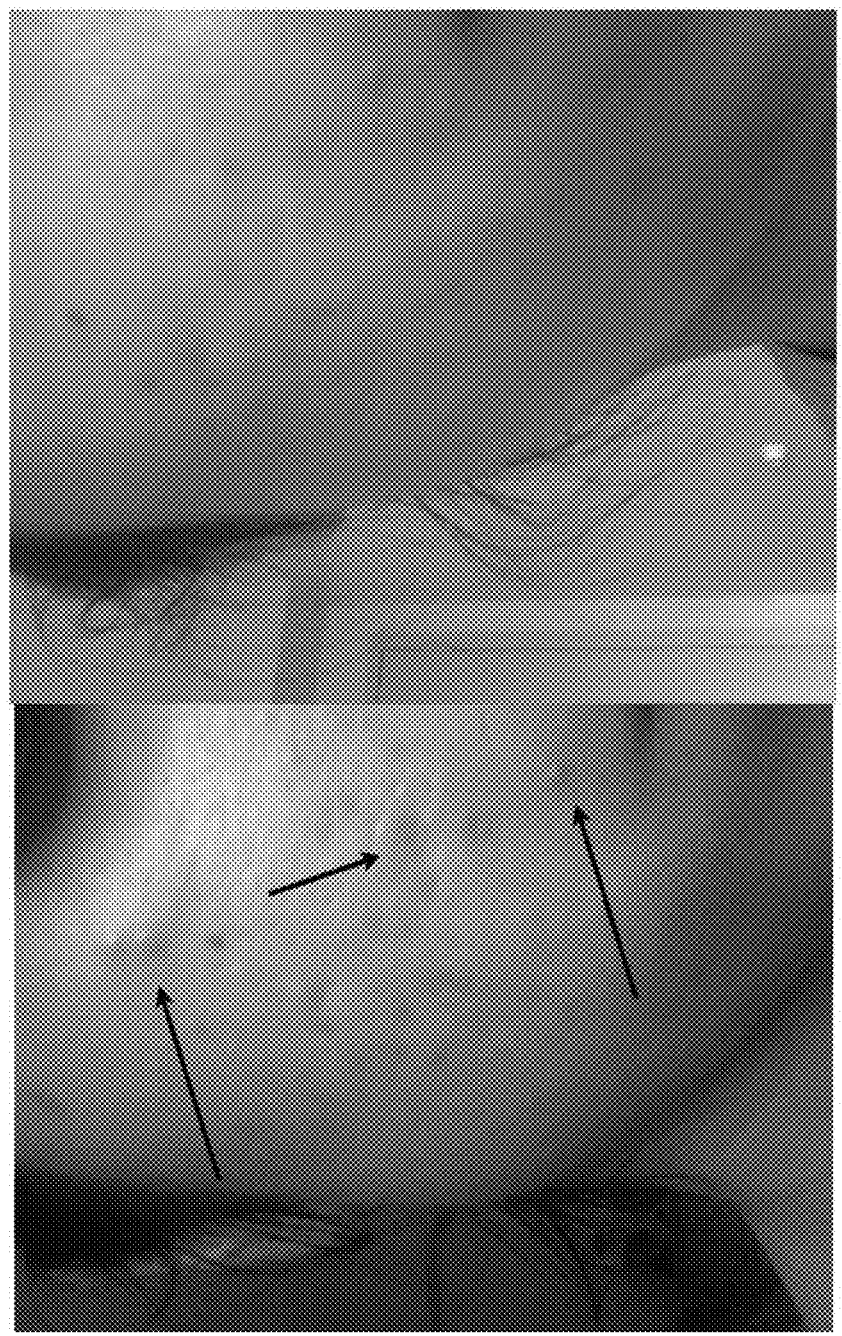
FIG. 3 shows results of treatment of gel treatment in an acne patient.

A 24 year old woman with frequent outbreaks of acne was treated with gel application twice a day for 8 weeks. FIG. 3 shows improvement in her acne condition.

Example 4.8

Figure 4:
FIG. 4 shows the results of treatment of an eczema patient with Metadichol gel. The eczema is on the patient's head. The number on the picture shows condition of skin on said day or week.

A 44 year old male with eczema of the forehead and hands was treated with gel for 6 weeks (FIG. 3 and FIG. 4). The results show complete disappearance of the infection on his forehead at 6 weeks and his hands in 4 weeks.

Example 4.9

Figure 5:
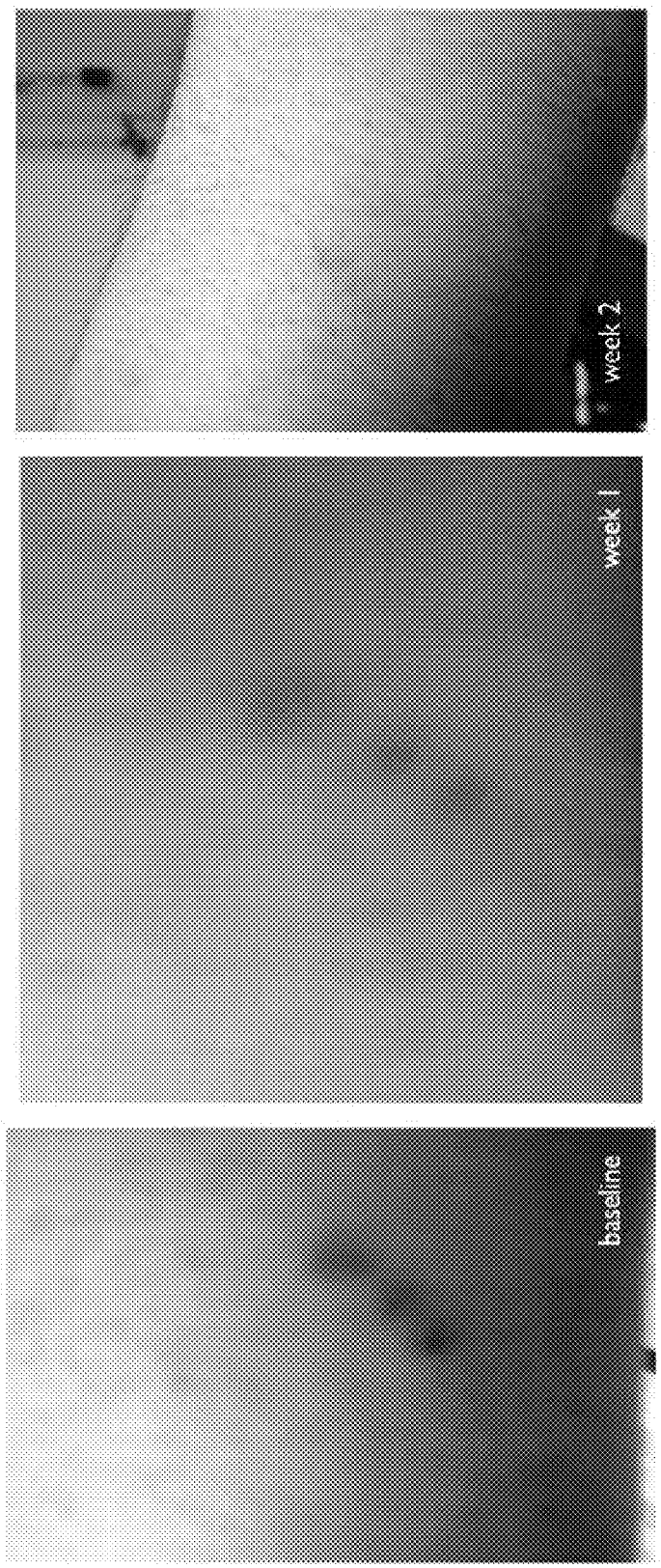
FIG. 5 shows the results of treatment of an eczema patient with Metadichol gel. The eczema is on the patient's arm. The number on the picture shows condition of skin on said day or week.
Figure 6:
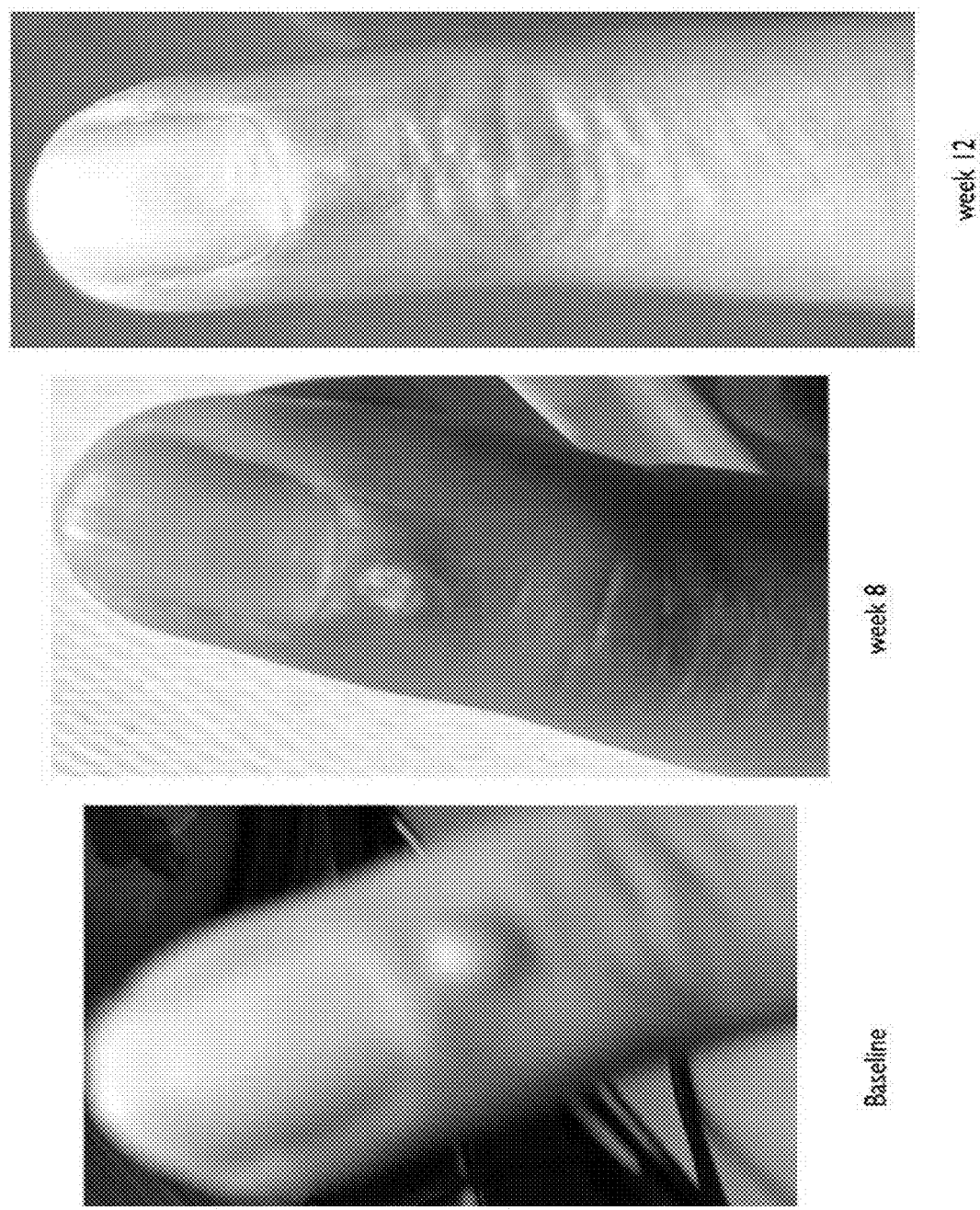
FIG. 6 shows results of Gel treatment of patient with ganglion

Patient Male 52 has this ganglion cyst (FIG. 5) for the past 5 years. Was unable to get rid of the cyst despite surgically removing it repeatedly. The cyst always recurred a few days after draining or removal. Use of Metadichol® gel for 4 weeks softened the cyst and was able to drain the cyst. The cyst has not grown back after stopping the gel usage.

Example 4.10

Female 58 years old with a sudden outbreak of a rash of unknown origin with serious itching associated with it (FIG.

6). Treated with Metadichol® gel application twice a day for 2 weeks and this led to the disappearance of most of the spots and itching abated in 10 days.

Example 4.11

Figure 7:
FIG. 7 shows results of treatment of gel on the leg of a patient with an outbreak of rash of unknown etiology.

A 11 year old male dog Shih-Tzu breed had lipoma (FIG. 7) that had become swollen and dark red and there appeared an exposed wound. Treatment with the gel with daily washing of the wound and application of the Metadichol® gel. News skin formation resulted and he is now able to walk and run normally. There was no hint of a previous injury at the site of treatment.

Example 4.12

Figure 8:
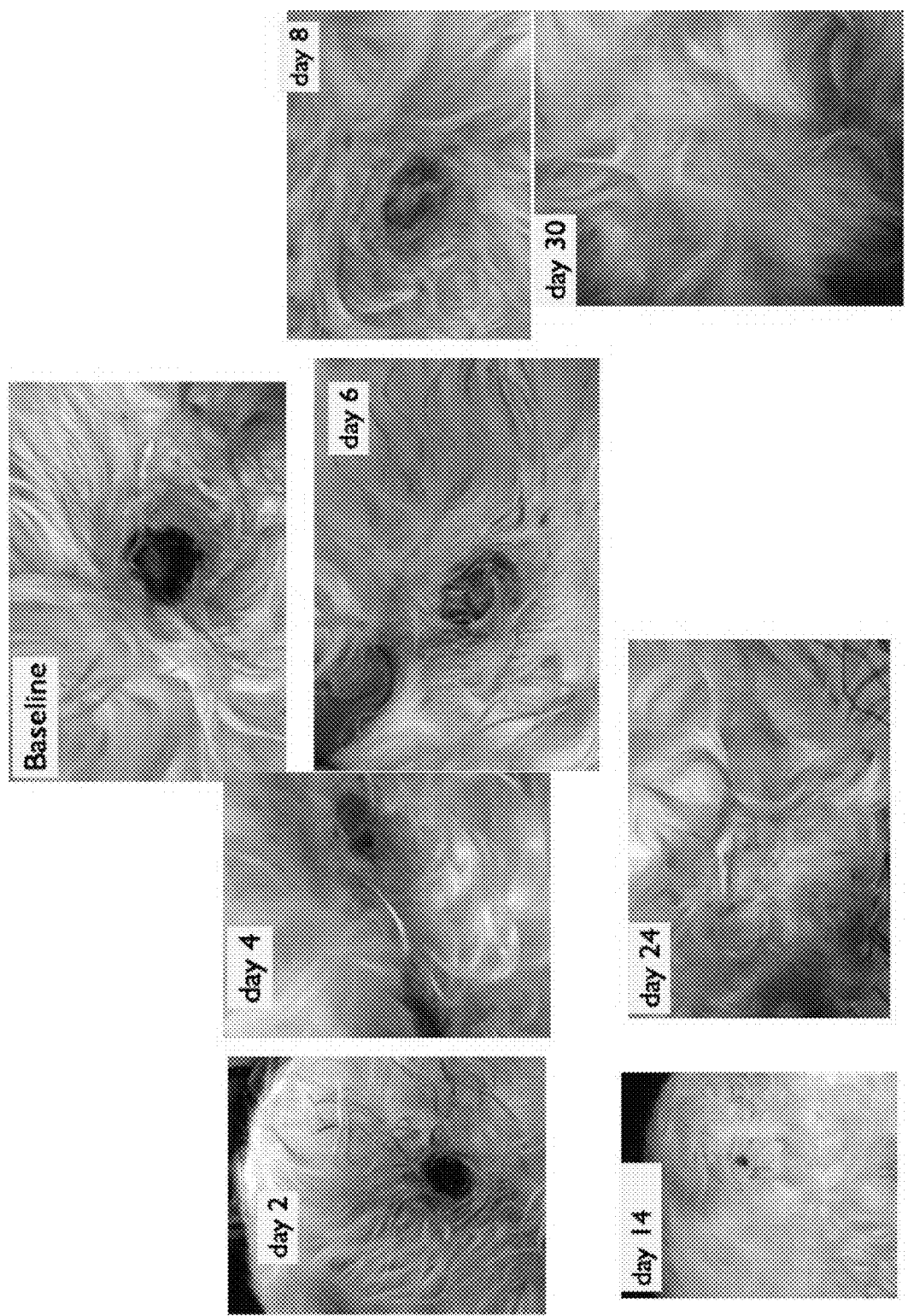
FIG. 8 shows treatment of gel on a dog with lipoma that developed into a open skin tumor infection.

Patient male 48 diagnosed on his finger with a CA-MRSA (community Associated methicillin-resistant *staphylococcus aureus*) infection (FIG. 8) Metadichol® gel application twice a day for 3 weeks stopped the infection and new skin grew and there is no sign of a earlier infection at that spot.

Example 4.13

Figure 9:
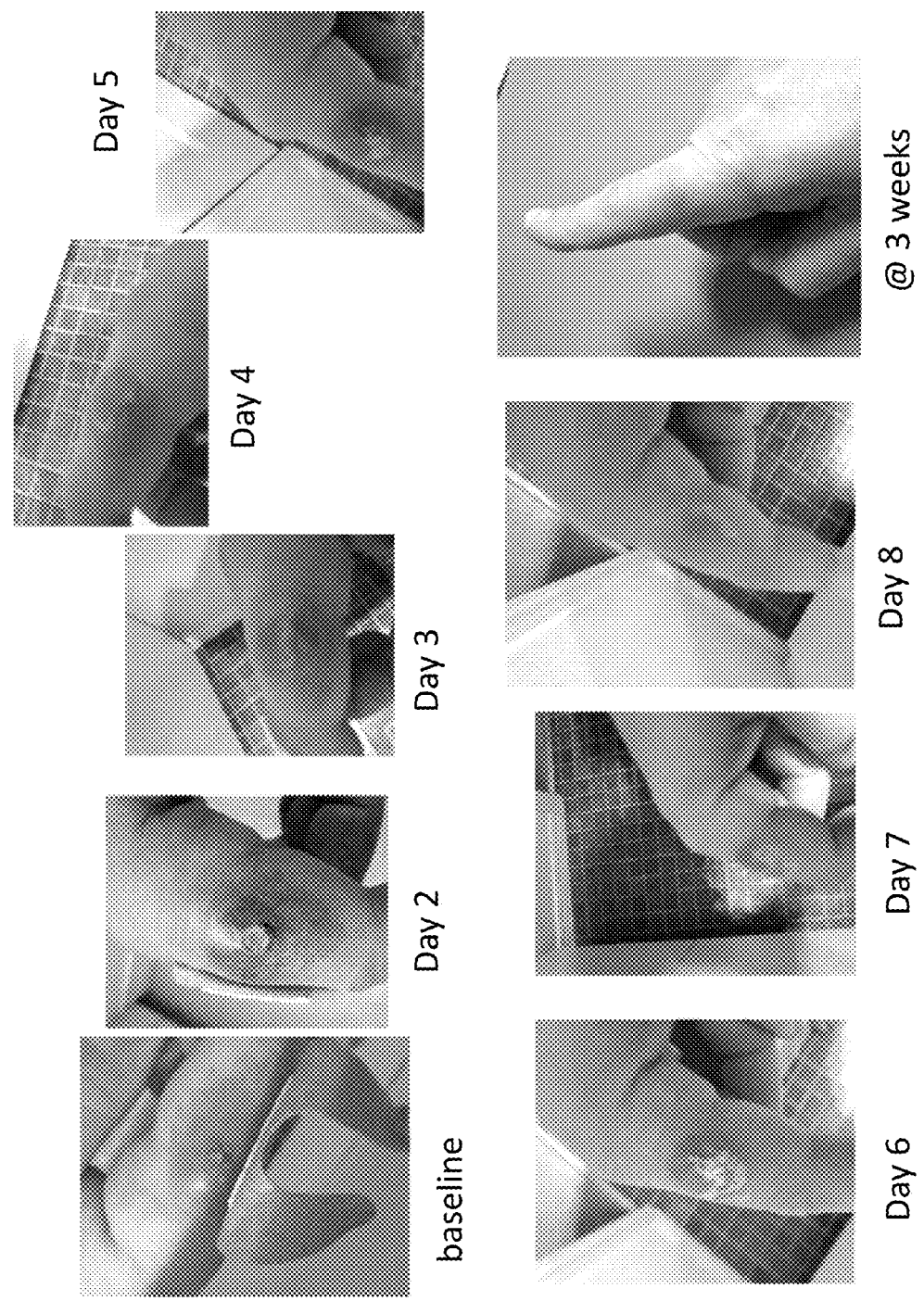
FIG. 9 shows treatment of a finger infection of a MRSA infected patient treated with Metadichol Gel.
Figure 10:
FIG. 10 shows skin treatment of a patient with gel under eye lids and face.

Female 58 years old applied gel under eyes and face and showed improved skin color and tone and removal fine lines and wrinkles (FIG. 9).

Example 5.0

Figure 11:
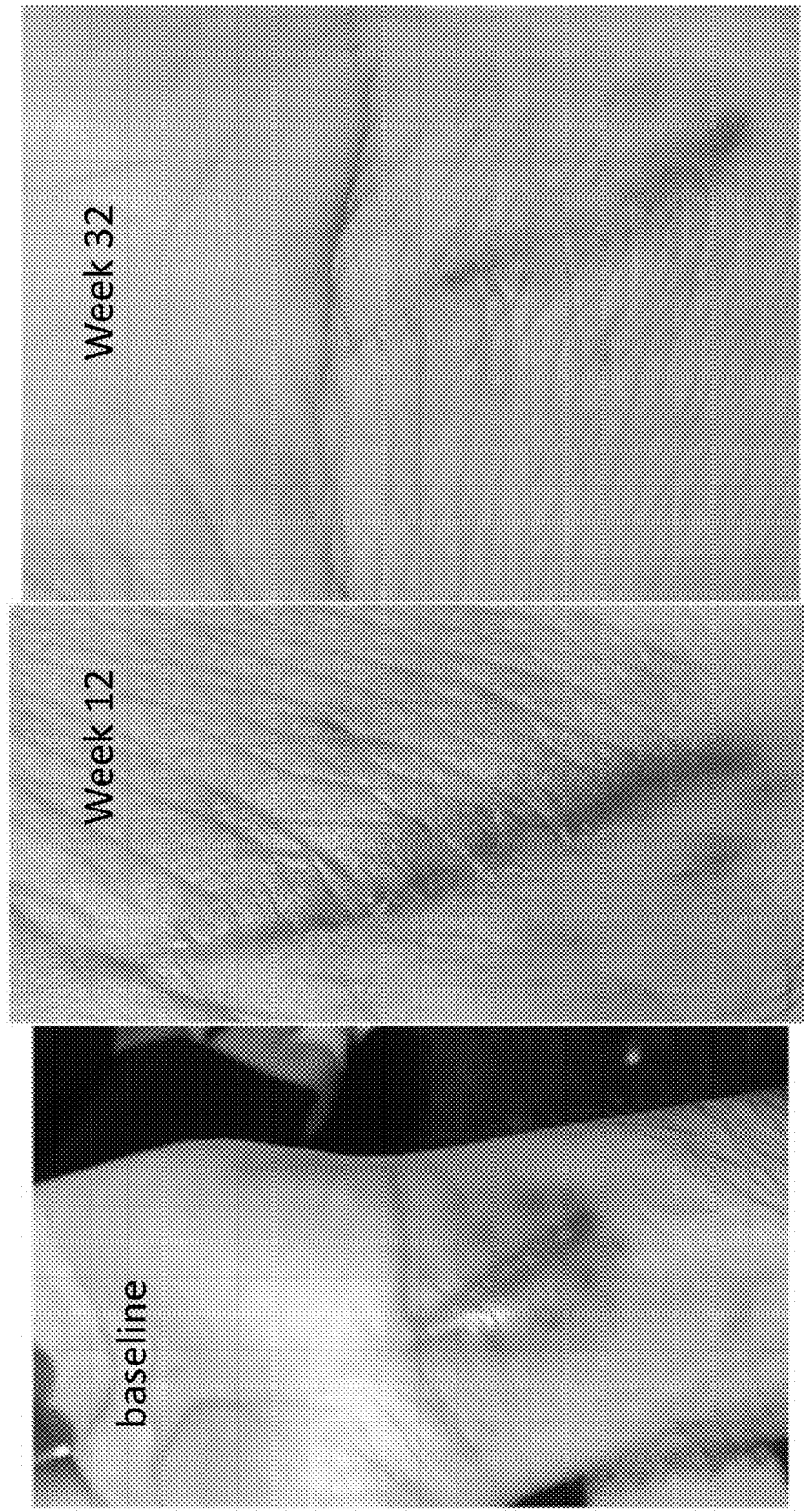
FIG. 11 shows Metadichol gel treatment of a patient with a deep wound on the hand.

Patient male 38 with a deep cut in hand that required 20 stitches treated with Metadichol® gel application twice a day for 32 weeks (FIG. 11).

Example 5.1

Figure 12:
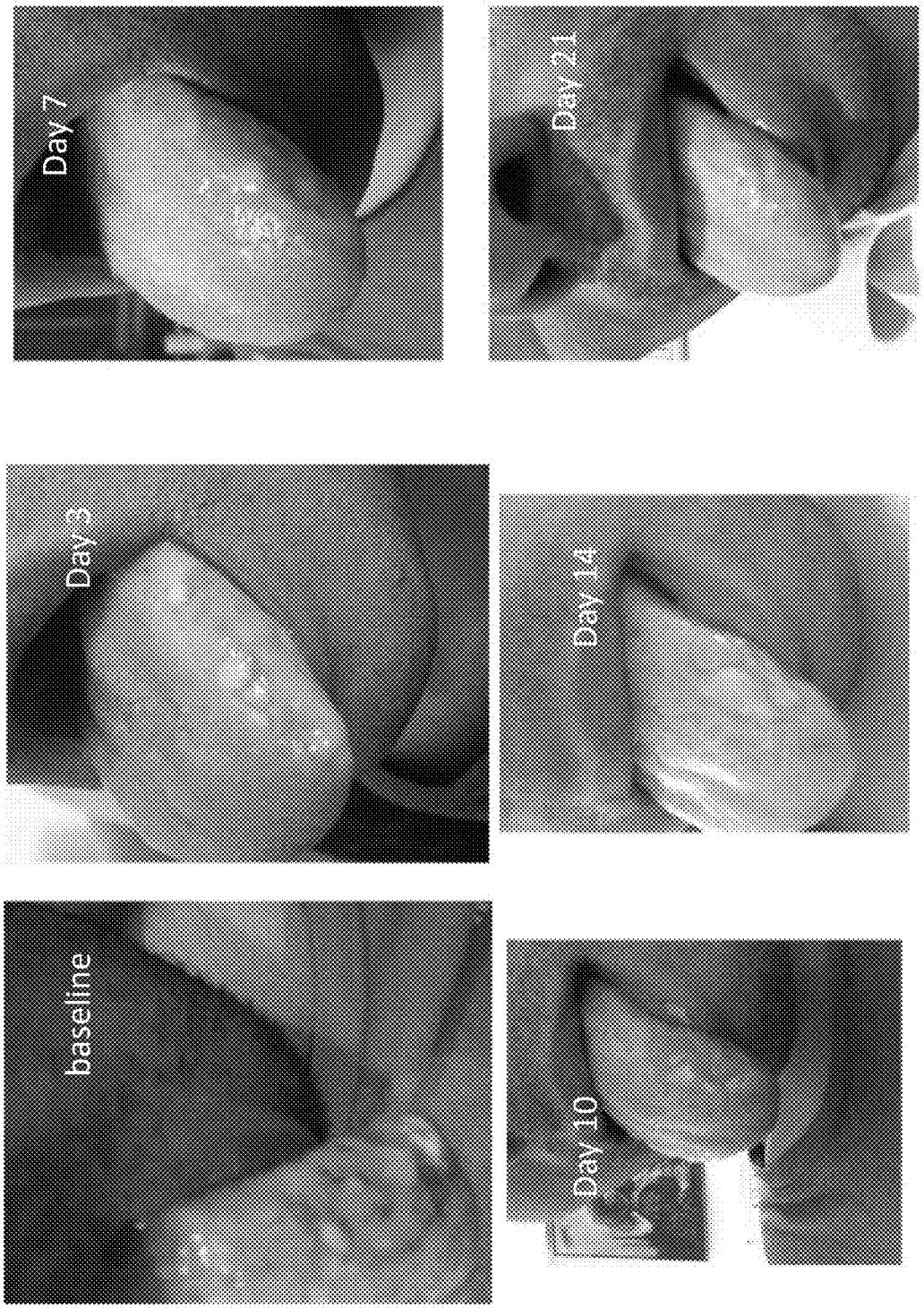
FIG. 12 shows Metadichol gel treatment of a patient suffering from a fungal infection of tongue.

Patient male 39 with a fungal infection of the tongue treated with Metadichol® gel by applying to effected areas of tongue twice a day. Tongue restored to normal healthy look (FIG. 12).

Example 5.2

Figure 13:
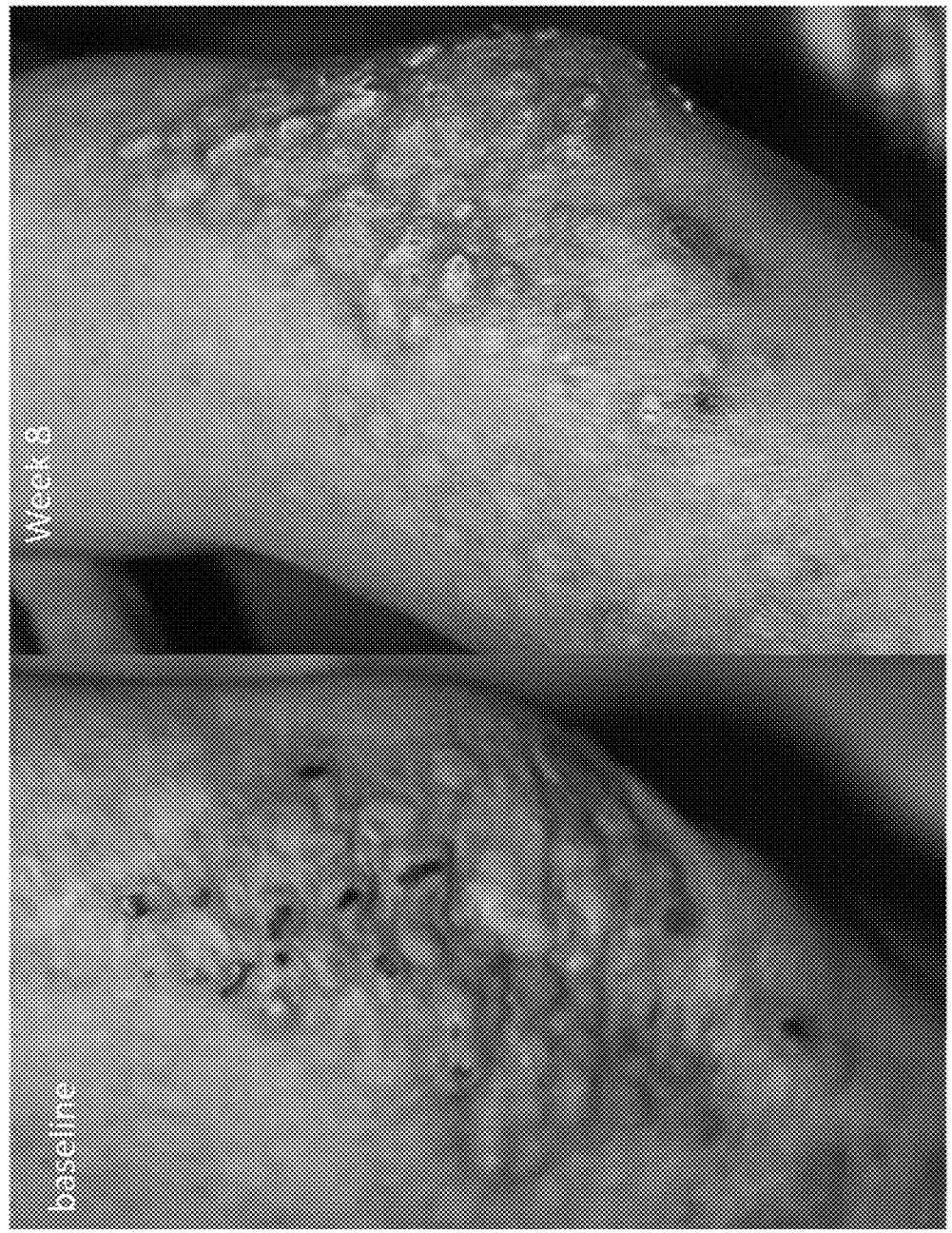
FIG. 13 shows Metadichol gel treatment of a patent with psoriasis.

Patient male 70 years old with psoriasis and itching treated with application of Metadichol® gel for 8 weeks. There was considerable improvement in the condition and patient itching stopped. (FIG. 13).

Example 5.3

Figure 14:
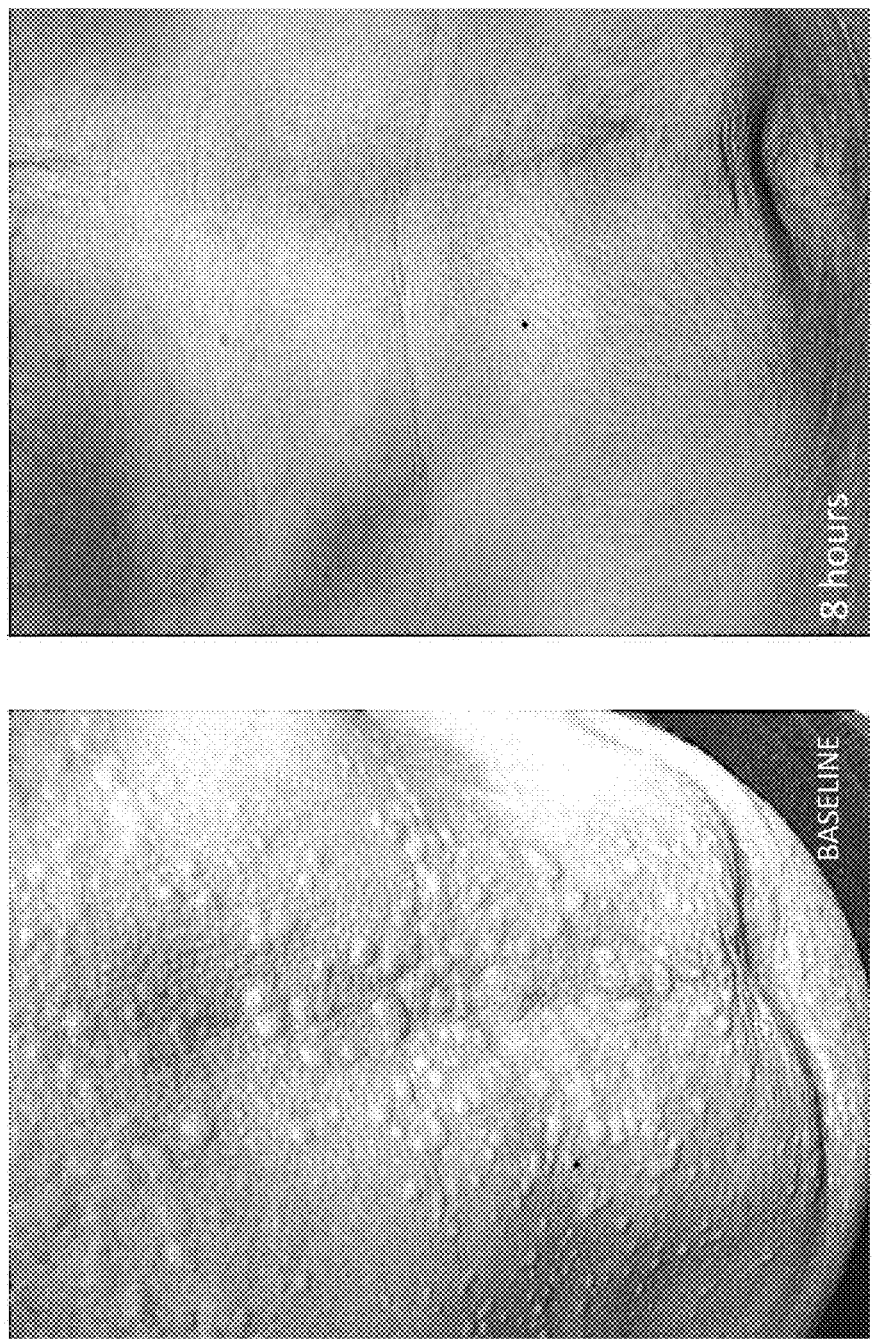
FIG. 14 shows Metadichol gel application of on a patient with a skin eruption.

Patient male 39, with sudden eruption of skin on stomach treated by applying Metadichol® gel over affected areas (FIG. 14).

Example 5.4

Figure 15:
FIG. 15 shows Metadichol gel application on a balding person and hair growth @4 months.

Patient male 55 with bald head applied twice a day Metadichol® gel for 16 weeks (FIG. 15).

Example 5.5

Patient Male 56 had on the internal skin layer of both ears a continuous overproduction of skin, a condition that had lasted for the last 30 years. Application of cortisone cream had a temporary success but with time the skin overproduction would return. After overnight application for a week of the Metadichol® Gel the skin returned to normal state without exfoliation.

Example 5.6

Female 56 years old suffering from plantar fasciitis for the previous six months and application of Metadichol® gel twice a day for one week led to complete remission of pain.

Example 5.7

Female 55 years old with symptoms: constant pain in the shoulder (even when resting), inability to lift left hand beyond shoulder height, difficulty reaching left hand behind the back Condition was Diagnosis (through x-rays and MRI) as tendinopathy in rotator cuff, superior labral tear, narrowing of c5-6 and c6-7 of the spine, bilateral cervical radiculopathy. Metadichol® gel application 5 days, 3 times a day. Led to sudden decrease in the pain level in the shoulder and rotator flexibility has increased. Neck—extent of turn improved.

Example 5.8

Patient Male 40 years old symptoms: acute pain in the lower part of left leg during any kind of sports activities and first ½ hour every morning. Diagnosed as Achilles tendinopathy.

Metadichol® gel application for 6 weeks, twice daily lead to a gradual decrease in pain and inflammation, complete recovery after 6 weeks with daily activities.

What is claimed is:

1. An aqueous gel composition having substantial water-barrier properties, said gel comprising:
   (a) a water-soluble polymer;
   (b) Metadichol nanoparticles in a therapeutically effective concentration; and
   (c) water,
   said gel being free of a film-forming polymer, occlusive fats or oils.

2. The composition of claim 1, wherein said water-soluble polymer is Carbopol.

3. A method of treating a skin disease in a subject, comprising: topically administering to said subject said gel of claim 1 in a therapeutically effective amount, wherein said skin disease is selected from a group consisting of inflammatory and hyper-proliferative dermatological illnesses, cutaneous manifestations of illnesses which are immunologic in origin like psoriasis, atopic dermatitis, contact dermatitis and other eczematous dermatitis's, seborrhoeic dermatitis, neurodermatitis, decubitus, lichen planus, pemphigus, bullate pemphigoid, epidermolysis bullosa, urticaria, angioedemas, vasculitides, erythema, cutaneous, eosinophilias, lupus erythematosuseczema, and MRSA, basal cell carcinoma, thereby descreasing the severity of the disease.

4. A method of treating a disease by improving a physiologic or metabolic parameter in a subject, said method comprising: administering to said subject a therapeutically effective amount of a pharmaceutical formulation comprising metadichol nanoparticles, said parameter being a member selected from increasing serum APO A1 protein levels in said subject, reducing lipoprotein (a) (Lp(a)) in said subject, increasing hemoglobin level in said subject, increasing platelet count in said subject, reducing the level of uric acid in said subject, regulating e GFR level in said subject, regulating a member selected from absolute neutrophils, absolute monocytes and white blood cell level in said subject; reducing elevated AST:ALT ratios in said subject, reducing ferritin level in said subject, reducing bilirubin level in said subject, regulating thyroid hormone (TSH) level in said subject, and lowering the level of a member selected from PTH, calcium, creatinine, alkaline phosphatase Bun levels and serum phosphorus levels in the subject, thereby regulating said parameter in said subject.

5. The method of claim 4 wherein said disease is kidney disease.

6. The method of claim 4 wherein said disease is a MRSA infection.

7. The method of claim 4 wherein said disease is a MDS.

8. The method of claim 4 wherein said disease is a hematological disease.

9. The method of claim 4 wherein said disease is prostate cancer.

10. The method of claim 3 wherein said disease is MRSA infection.

11. The method of claim 3 where the disease is Eczema.

12. The method of claim 3 wherein the subject is a human.

* * * * *